United States Patent
Ichikawa et al.

(10) Patent No.: US 8,685,617 B2
(45) Date of Patent: Apr. 1, 2014

(54) SALT, PHOTORESIST COMPOSITION AND PROCESS FOR PRODUCING PHOTORESIST PATTERN

(75) Inventors: Koji Ichikawa, Osaka (JP); Isao Yoshida, Osaka (JP); Yuki Suzuki, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 144 days.

(21) Appl. No.: 13/333,521

(22) Filed: Dec. 21, 2011

(65) Prior Publication Data

US 2012/0164579 A1     Jun. 28, 2012

(30) Foreign Application Priority Data

Dec. 24, 2010 (JP) ................. 2010-287364

(51) Int. Cl.
  *G03F 7/004* (2006.01)
  *G03F 7/028* (2006.01)
  *C07C 309/02* (2006.01)
  *C07C 309/04* (2006.01)
  *C07C 309/06* (2006.01)

(52) U.S. Cl.
  USPC ............ 430/270.1; 430/326; 562/30; 568/24; 568/28

(58) Field of Classification Search
  USPC ......... 430/270.1, 326, 921, 923, 925; 562/30; 568/22, 24, 27, 28, 34
  See application file for complete search history.

(56) References Cited

U.S. PATENT DOCUMENTS

| | | | |
|---|---|---|---|
| 2008/0086014 A1 | 4/2008 | Shigematsu et al. | |
| 2009/0208871 A1* | 8/2009 | Kawaue et al. | 430/285.1 |
| 2011/0076615 A1* | 3/2011 | Kawabata et al. | 430/270.1 |

* cited by examiner

*Primary Examiner* — Anca Eoff
(74) *Attorney, Agent, or Firm* — Birch, Stewart, Kolasch & Birch, LLP

(57) ABSTRACT

A salt represented by the formula (I):

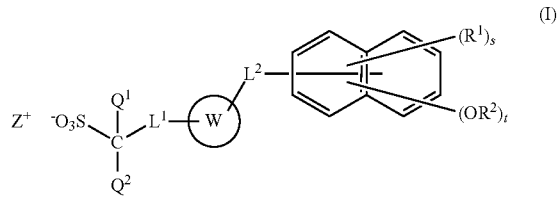

wherein $Q^1$, $Q^2$, $L^1$, $L^2$, ring W, s, t, $R^1$, $R^2$ and $Z^+$ are defined in the specification.

9 Claims, No Drawings

SALT, PHOTORESIST COMPOSITION AND PROCESS FOR PRODUCING PHOTORESIST PATTERN

This nonprovisional application claims priority under 35 U.S.C. §119(a) on Patent Application No. 2010-287364 filed in JAPAN on Dec. 24, 2010, the entire contents of which are hereby incorporated by reference.

FIELD OF THE INVENTION

The present invention relates to a salt, a photoresist composition and a process for producing a photoresist composition.

BACKGROUND OF THE INVENTION

US2008-086014(A1) mentions a photoresist composition comprising a salt represented by the following formula:

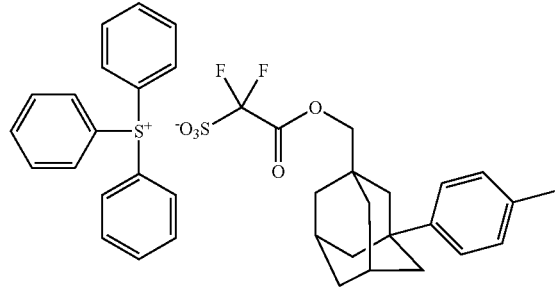

as an acid generator.

SUMMARY OF THE INVENTION

The present invention is to provide a salt for suitable for an acid generator and a photoresist composition comprising the same.

The present invention relates to the followings:
<1> A salt represented by the formula (I):

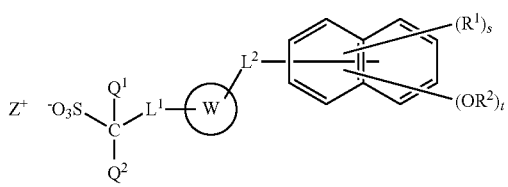

wherein $Q^1$ and $Q^2$ independently each represent a fluorine atom or a C1-C6 perfluoroalkyl group,
$L^1$ represents a C1-C17 divalent saturated hydrocarbon group in which one or more —$CH_2$— can be replaced by —O— or —CO—,
$L^2$ represents a C1-C6 divalent saturated hydrocarbon group in which one or more —$CH_2$— can be replaced by —O— or —CO—,
ring W represents a C3-C36 aliphatic ring in which one or more —$CH_2$— can be replaced by —O—, —S—, —CO— or —$SO_2$— and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group,
s represents an integer of 0 to 3,
t represents an integer of 0 to 2,
$R^1$ independently represents in each occurrence a C1-C18 alicyclic hydrocarbon group in which one or more —$CH_2$— can be replaced by —O— or —CO—,
$R^2$ independently represents in each occurrence a hydrogen atom, a C1-C6 alkyl group, a C3-C12 cycloalkyl group, a C2-C7 acyl group, a C2-C7 alkoxycarbonyl group, a C2-C7 alkoxyalkyl group or a glycidyl group, and
$Z^+$ represents an organic counter ion.
<2> The salt according to <1> wherein the formula (1) is represented by the formula:

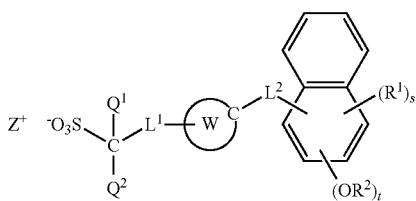

in which $Q^1$, $Q^2$, $L^1$, $L^2$, ring W, s, t, $R^1$, $R^2$, and $Z^+$ are defined as above.
<3> The salt according to <1> or <2>, wherein ring W is a ring represented by the formula (Ia1-1), (Ia1-2) or (Ia1-3):

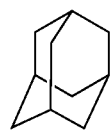
(Ia1-1)

(Ia1-2)

(Ia1-3)

wherein one or more —$CH_2$— in the above-mentioned formula can be replaced by —O—, —S—, —CO— or —$SO_2$— and one or more hydrogen atoms in the above-mentioned formula can be replaced by a hydroxyl group, a C1-C12 alkyl group, a C1-C12 alkoxy group, a C3-C12 alicyclic hydrocarbon group or a C6-C10 aromatic hydrocarbon group.
<4> The salt according to <1> or <2> wherein $L^1$ is *—CO—O—($CH_2$)$_u$—in which u represents an integer of 0 to 6 and * represents a binding position to —C($Q^1$) ($Q^2$)-.
<5> The salt according to any one of <1> to <4>, wherein $L^1$ is *—CO—O—($CH_2$)$_n$— in which v represents an integer of 0 to 4 and * represents a binding position to ring W.
<6> The salt according to any one of <1> to <5>, wherein $Z^+$ is an arylsulfonium cation.
<7> An acid generator comprising the salt according to any one of <1> to <6>.
<8> A photoresist composition comprising the acid generator according to <7> and a resin having an acid-labile group, being insoluble or poorly soluble in an aqueous alkali solution but becoming soluble in an aqueous alkali solution by the action of an acid.

<9> The photoresist composition according to <8>, which further comprises a basic compound.

<10> A process for producing a photoresist composition pattern comprising the following steps (1) to (5):

(1) a step of applying the photoresist composition according to <8> or <9> on a substrate, (2) a step of drying the composition on the substrate to form a composition film, (3) a step of exposing the composition film to radiation, (4) a step of baking the exposed film, and (5) a step of developing the baked resist film to thereby form a photoresist pattern.

DESCRIPTION OF PREFERRED EMBODIMENTS

In the present specification, the number attached to "C" means the carbon number of each group.

When a group can form linear and branched chain and/or cyclic structures, all structures are included and may simultaneously present in one group, unless otherwise specified. When one group of moiety takes a stereoisomeric form, all stereoisomeric forms are included. Each group can form monovalent, or di- or more-valent group depending on the bonded position and bonding form.

A hydrocarbon group includes an aliphatic hydrocarbon group and an aromatic group. The aliphatic hydrocarbon group includes a chain aliphatic hydrocarbon group, an alicyclic hydrocarbon group and a combination thereof. The aliphatic hydrocarbon group may be any of a liner and a branched chain aliphatic hydrocarbon groups. The chain aliphatic hydrocarbon group may include a carbon-carbon double bond, but a saturated chain aliphatic hydrocarbon group, i.e., alkyl group, is preferable.

Among chain aliphatic hydrocarbon groups, an alkyl group is a typical monovalent chain aliphatic hydrocarbon group.

Examples of an alkyl group include methyl, ethyl, propyl, butyl, pentyl, hexyl, heptyl, octyl, decyl, dodecyl, hexadecyl, pentadecyl, hexyldecyl, heptadecyl and octadecyl groups.

Examples of a divalent chain aliphatic hydrocarbon group include a group in which one hydrogen atom is removed from the above the monovalent chain aliphatic hydrocarbon group, i.e., alkanediyl group.

Examples of alkanediyl group include methylene, ethylene, propane-1,3-diyl, propane-1,2-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, pentadecane-1,17-diyl, ethane-1,1-diyl, propane-1,1-diyl, propane-2,2-diyl, 2-methylpropane-1,3-diyl, 2-methylpropane-1,2-diyl, pentane-1,4-diyl or 2-methylbutane-1,4-diyl groups The cyclic aliphatic hydrocarbon group may be any of a monocyclic or a polycyclic aliphatic hydrocarbon groups, which hereinafter may be referred to as "alicyclic hydrocarbon group" The cyclic aliphatic hydrocarbon group typically includes cycloalkyl groups.

Among a monovalent alicyclic hydrocarbon group, examples of monocyclic alicyclic hydrocarbon group typically include a group in which one hydrogen atom is removed from a cycloalkane represented by any one of formulae (KA-1) to (KA-7).

 (KA-1)

 (KA-2)

 (KA-3)

 (KA-4)

 (KA-5)

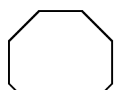 (KA-6)

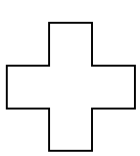 (KA-7)

Examples of polycyclic alicyclic hydrocarbon group typically include a group in which one hydrogen atom is removed from a cycloalkane represented by any one of formulae (KA-8) to (KA-22).

 (KA-8)

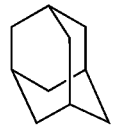 (KA-9)

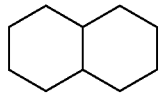 (KA-10)

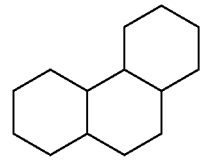 (KA-11)

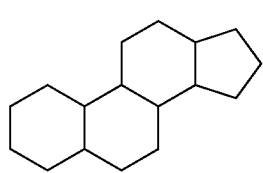 (KA-12)

(KA-13)
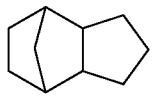

(KA-14)
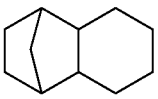

(KA-15)
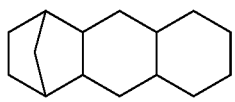

(KA-16)
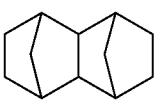

(KA-17)
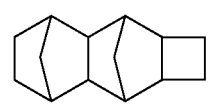

(KA-18)
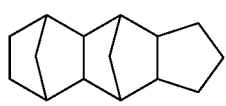

(KA-19)

(KA-20)

(KA-21)
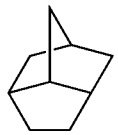

(KA-22)

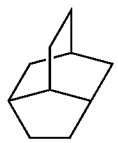

Examples of a divalent alicyclic hydrocarbon group include a group in which two hydrogen atoms are removed from the alicyclic hydrocarbon group.

Examples of the aromatic hydrocarbon group typically include an aryl group such as phenyl, naphthyl, anthryl, biphenyl, phenanthryl and fluorenyl groups.

The aliphatic hydrocarbon group and the aromatic hydrocarbon group may be substituted with a substituent.

Typical examples of the substituent of the aliphatic hydrocarbon group include a halogen atom, an alkoxy group, an acyl group, an aryl group, an aralkyl group and an aryloxy group.

Typical examples of the substituent of the aromatic hydrocarbon group include a halogen atom, an alkoxy group, an acyl group, an alkyl group and an aryloxy group.

Examples of the halogen atom include fluorine, chlorine, bromine and iodine atoms.

Examples of the alkoxyl group include methoxy, ethoxy, propoxy, butoxy, pentyloxy, hexyloxy, heptyloxy, octyloxy, decyloxy and dodecyloxy groups. The alkoxyl group may be any of a liner and a branched chain alkoxyl groups.

Examples of an alkylthio group include a group in which an oxygen atom has been replaced by a sulfur atom. Such group includes methylthio, ethylthio, propylthio, butylthio, pentylthio, hexylthio, heptylthio, octylthio, decylthio and dodecylthio groups.

Examples of the acyl group include a group bonding a carbonyl group to the alkyl group, such as, acetyl, propionyl, butyryl, valeryl, hexylcarbonyl, heptylcarbonyl, octylcarbonyl, decylcarbonyl and dodecylcarbonyl groups, and a group bonding a carbonyl group to the aryl group, such as, benzoyl group. The alkyl group in the acyl group may be any of a liner and a branched chain alkyl groups.

Examples of the acyloxy group include acetyloxy, propionyloxy, butyryloxy or isobutyryloxy group.

Examples of the aralkyl group include benzyl, phenethyl, phenylpropyl, naphthylmethyl and naphthylethyl groups.

Examples of the aryloxy group include a group bonding an oxygen atom to the above aryl group.

Saturated hydrocarbon group means a saturated group among aliphatic hydrocarbon groups, i.e., a saturated group among chain or cyclic aliphatic hydrocarbon groups as mentioned above. Saturated hydrocarbon group may have a substituent.

The term "(meth)acrylic monomer" means at least one monomer having a structure of "$CH_2$=CH—CO—" or "$CH_2$=C($CH_3$)—CO—", as well as "(meth)acrylate" and "(meth)acrylic acid" mean "at least one acrylate or methacrylate" and "at least one acrylic acid or methacrylic acid", respectively.

<Salt Represented by the Formula (I)>

The salt of the present invention is represented by the formula (I) (hereinafter, such salt is referred to as "SALT (I)"):

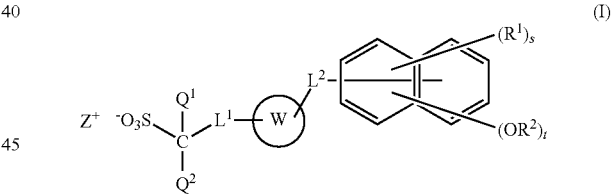

wherein $Q^1$ and $Q^2$ independently each represent a fluorine atom or a C1-C6 perfluoroalkyl group, $L^1$ represents a C1-C17 divalent saturated hydrocarbon group in which one or more —$CH_2$— can be replaced by —O— or —CO—, $L^2$ represents a C1-C6 divalent saturated hydrocarbon group in which one or more —$CH_2$— can be replaced by —O— or —CO—, ring W represents a C3-C36 aliphatic ring in which one or more —$CH_2$— can be replaced by —O—, —S—, —CO— or —$SO_2$— and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group, s represents an integer of 0 to 3, t represents an integer of 0 to 2, $R^1$ independently represents in each occurrence a C1-C18 alicyclic hydrocarbon group in which one or more —$CH_2$— can be replaced by —O— or —CO—, $R^2$ independently represents in each occurrence a hydrogen atom, a C1-C6 alkyl group, a C3-C12 cycloalkyl group, a C2-C7 acyl group, a C2-C7 alkoxycarbonyl group, a C2-C7 alkoxyalkyl group or a glycidyl group, and $Z^+$ represents an organic counter ion.

In the formula (I), the groups represented by $R^1$, $OR^2$, and $L^2$ may bind to any carbon of the naphthalene ring.

The salt of the formula (I) includes the salt of the formula:

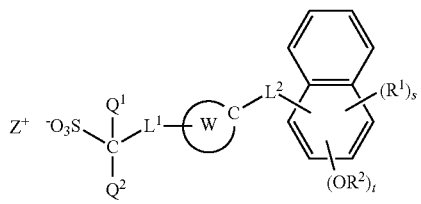

in which $Q^1$, $Q^2$, $L^1$, $L^2$, ring W, s, t, $R^1$, $R^2$, and $Z^+$ are defined as above.

Hereinafter, a moiety of SALT (I) which has a negative charge and from which the organic cation represented by $Z^+$ has been removed is sometimes referred to as "sulfonic acid anion"

Examples of perfluoroalkyl group include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group.

Examples of the divalent saturated hydrocarbon group include a linear or branched alkanediyl group and divalent monocyclic or polycyclic divalent alicyclic hydrocarbon group.

It is preferred that $Q^1$ and $Q^2$ independently each represent a fluorine atom or a trifluoromethyl group, and it is more preferred that $Q^1$ and $Q^2$ are fluorine atoms.

When $L^1$ represents a C1-C17 divalent saturated hydrocarbon group in which one or more —$CH_2$— are replaced by —O— or —CO—, examples thereof include the formulae (b1-1) to (b1-7) as follow.

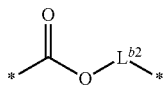 (b1-1)

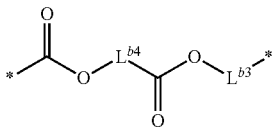 (b1-2)

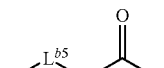 (b1-3)

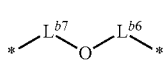 (b1-4)

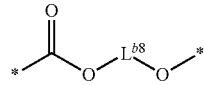 (b1-5)

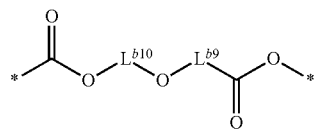 (b1-6)

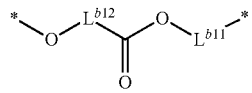 (b1-7)

In these formulae, $L^{b2}$ represents a single bond or a C1-C15 divalent saturated hydrocarbon group, $L^{b3}$ represents a single bond or a C1-C12 divalent saturated hydrocarbon group, $L^{b4}$ represents C1-C13 divalent saturated hydrocarbon group, with the proviso that total carbon number of $L^{b3}$ and $L^{b4}$ is 1 to 13, $L^{b5}$ represents a C1-C15 divalent saturated hydrocarbon group, $L^{b6}$ represents a single bond or a C1-C15 divalent saturated hydrocarbon group, $L^{b7}$ represents a C1-C15 divalent saturated hydrocarbon group, with the proviso that total carbon number of $L^{b6}$ and $L^{b7}$ is 1 to 16, $L^{b8}$ represents a C1-C14 divalent saturated hydrocarbon group, $L^{b9}$ represents a single bond or a C1-C11 divalent saturated hydrocarbon group, $L^{b10}$ represents a C1-C12 divalent saturated hydrocarbon group, with the proviso that total carbon number of $L^{b9}$ and $L^{b10}$ is 1 to 12, $L^{b11}$ represents a single bond or a C1-C13 divalent saturated hydrocarbon group, $L^{b12}$ represents a C1-C14 divalent saturated hydrocarbon group, with the proviso that total carbon number of $L^{b11}$ and $L^{b12}$ is 1 to 14 and * represents a binding position.

Herein the formulae (b1-1) to (b1-7) are expressed by the same manner as the formula (I) in terms of binding positions, the binding position at the left side of which binds to the carbon atom of —$C(Q^1)(Q^2)$—. Specific examples of the formulae (b1-1) to (b1-7) are expressed in the same manner as the formulae.

$L^1$ is preferably one of the groups represented by the formulae (b1-1), (b1-2), (b1-3) and (b1-4), more preferably one of the groups represented by the formulae (b1-1) and (b1-3), still more preferably a divalent group represented by the formula (b1-1), in particular preferably a divalent group represented by the formula (b1-1) in which $L^{b2}$ represents a single bond or a C1-C6 saturated hydrocarbon group, such as *—CO—O—$(CH_2)_u$— (wherein u represents an integer of 0 to 6, and * represents a binding position to —$C(Q^1)(Q^2)$-), most preferably a divalent group represented by the formula (b1-1) in which $L^{b2}$ represents a single bond or a methylene group, i.e. *—CO—O— and *—CO—O—$CH_2$—.

Examples of the divalent group represented by the formula (b1-1) include those shown bellow:

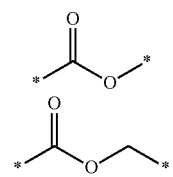

Examples of the divalent group represented by the formula (b1-2) include those shown bellow:

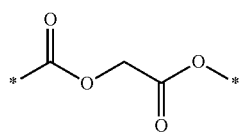
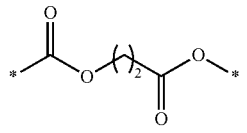
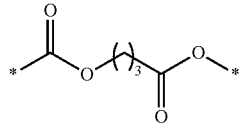
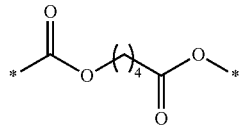
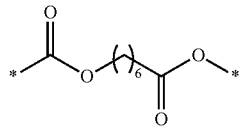
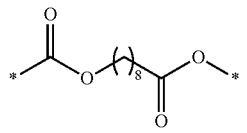
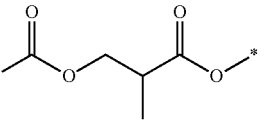
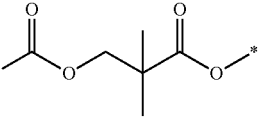
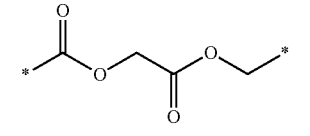
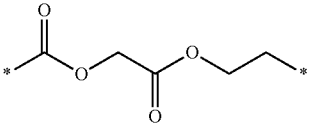
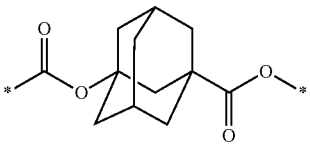
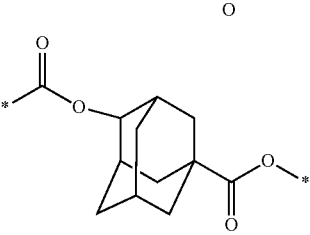
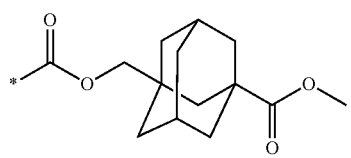
Examples of the divalent group represented by the formula (b1-3) include those shown bellow:
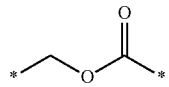
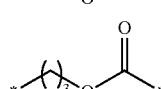
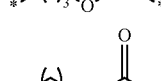
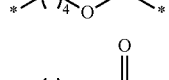
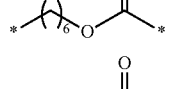
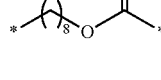
Examples of the divalent group represented by the formula (b1-4) include those shown bellow:
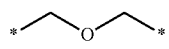
Examples of the divalent group represented by the formula (b1-5) include those shown bellow:
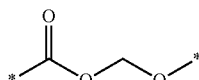
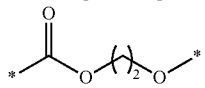
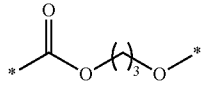
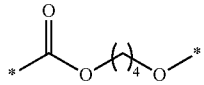
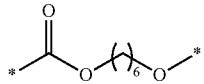
Examples of the divalent group represented by the formula (b1-6) include those shown bellow:

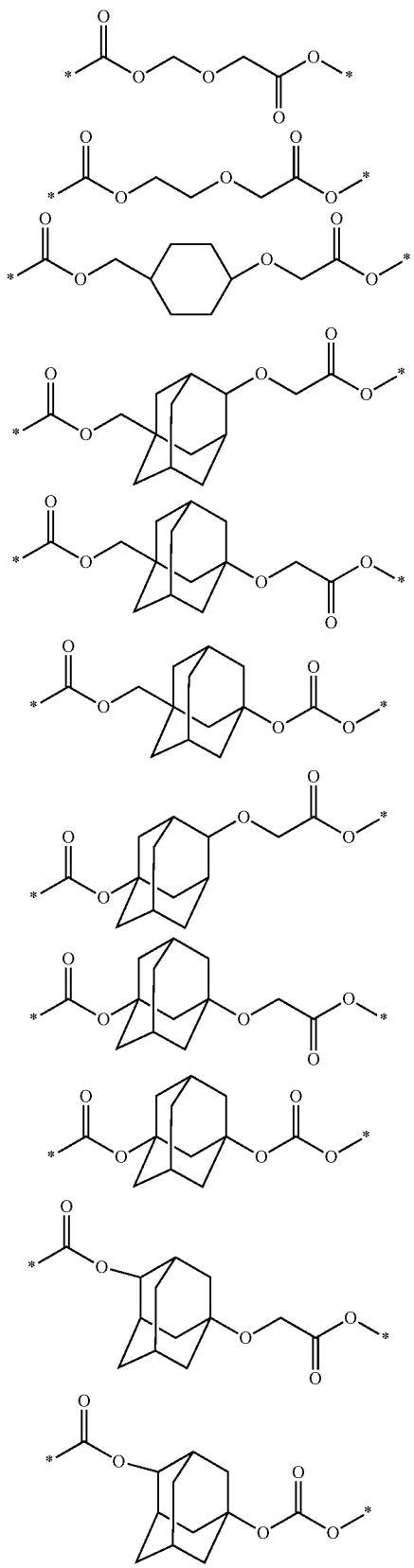

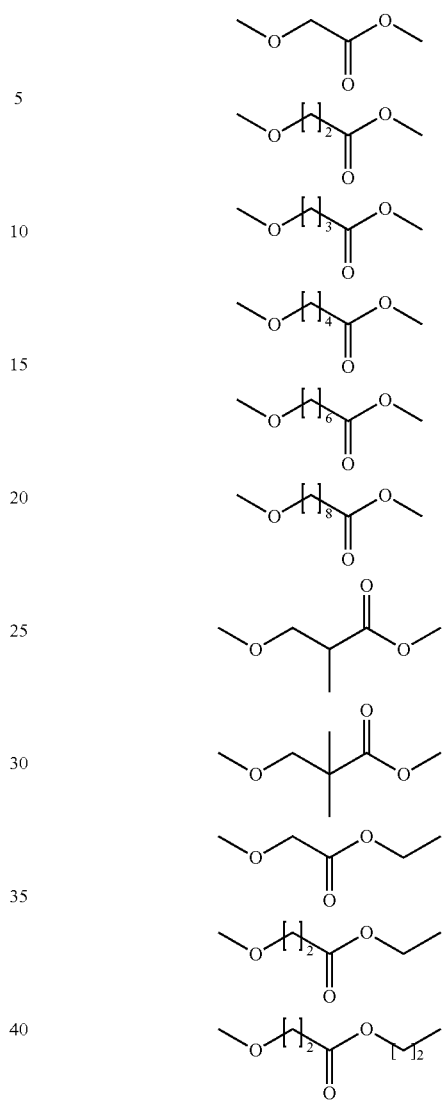

The saturated hydrocarbon group represented by $L^2$ in which one or more —$CH_2$— are replaced by —O— or —CO— include *—CO—O—, *—CO—O—$(CH_2)_v$— (wherein v represents an integer of 0 to 4), *—O—CO—, *—O—$CH_2$—CO—O—, *—O—CO—$CH_2$—O—, *—O—$CH_2$—CO—O—$CH_2$—, *—O—CO—$CH_2$—O—$CH_2$— and *—O—$CH_2$—$CH_2$—O—.

The group represented by $L^2$ is preferably a single bond or *—CO—O—$(CH_2)_v$— (wherein v represents an integer of 0 to 4).

The aliphatic ring represented by ring W include the following rings represented by the formulae (Ia1-1), (Ia1-2) and (Ia1-3):

(Ia1-1)

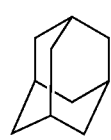

Examples of the divalent group represented by the formula (b1-7) include those shown bellow:

(Ia1-2)

(Ia1-3)

wherein one or more —CH$_2$— in the above-mentioned formulae can be replaced by —O—, —S—, —CO— or —SO$_2$— and one or more hydrogen atoms can be replaced by a hydroxyl group, a C1-C12 alkyl group, a C1-C12 alkoxy group, a C3-C12 alicyclic hydrocarbon group or a 06-C10 aromatic hydrocarbon group.

In the rings represented by the formulae (Ia1-1), (Ia1-2) and (Ia1-3), C3-C12 alicyclic hydrocarbon group in which one or more hydrogen atoms can be replaced include:

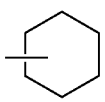

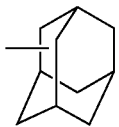

In the rings represented by the formulae (Ia1-1), (Ia1-2) and (Ia1-3), C6-C10 aromatic hydrocarbon group in which one or more hydrogen atoms can be replaced include phenyl group or naphtyl group.

The alicyclic hydrocarbon group represented by R$^1$ is preferably an alkyl group, an alicyclic hydrocarbon group or a group consisting of the alkyl group and the alicyclic hydrocarbon group. Examples of the alicyclic hydrocarbon group preferably include the groups shown as follow:

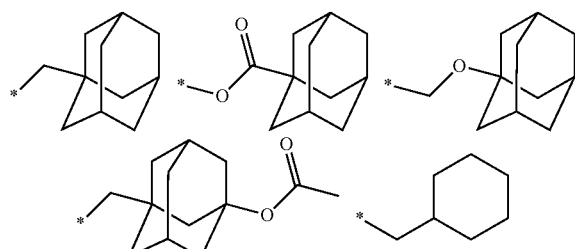

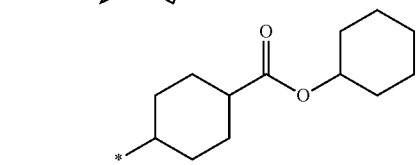

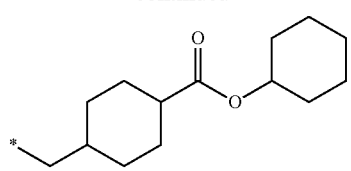

When a methylene group of the alicyclic hydrocarbon group represented by R$^1$ has been replaced by —O— or —CO—, the number of the replaced methylene group is up to two. In this case, the alicyclic hydrocarbon group represented by R$^1$ includes those shown as follow:

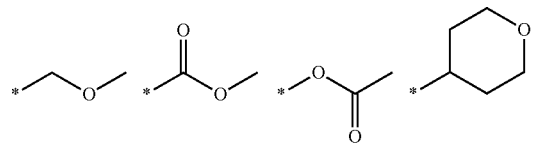

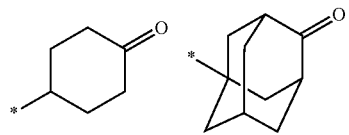

Examples of the alkoxy group in R$^2$ include methoxycarbonyl or t-butoxycarbonyl.

Examples of the alkoxyalkyl group in R$^2$ include a methoxymethyl group or an ethoxyethyl group.

Sulfonate anion of the SALT (I) include the group shown as follow:

(Ia1-1-1)

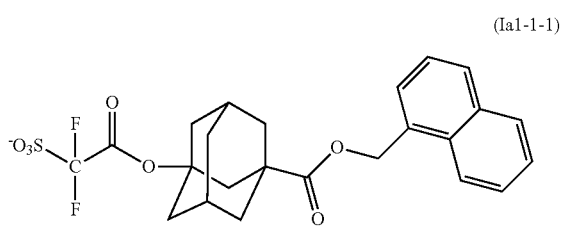

(Ia1-1-2)

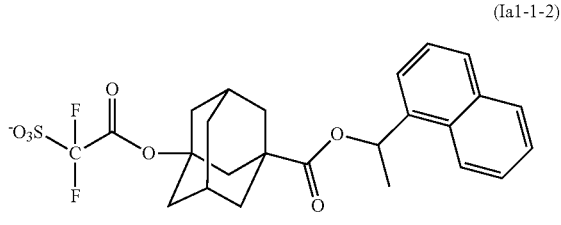

(Ia1-1-3)

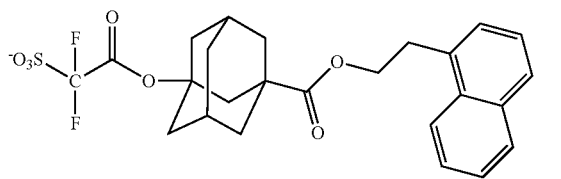

(Ia1-1-4)
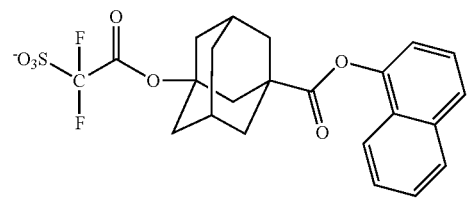
(Ia1-1-5)
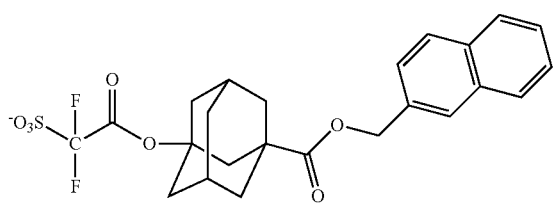
(Ia1-1-6)
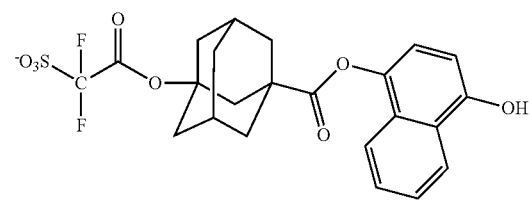
(Ia1-1-7)
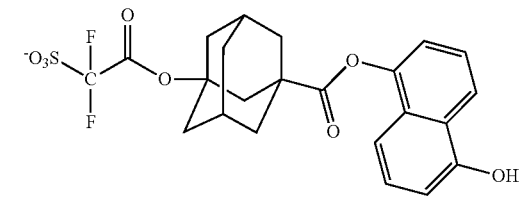
(Ia1-1-8)
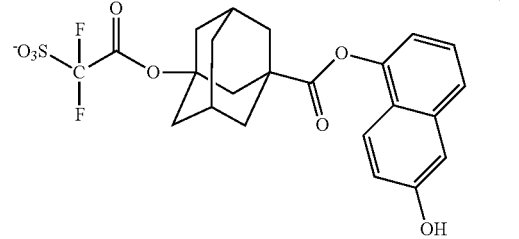
(Ia1-1-9)
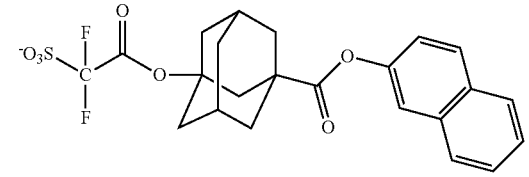
(Ia1-1-10)
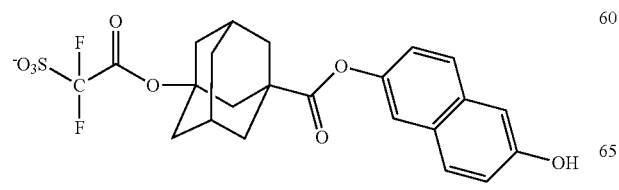
(Ia1-1-11)
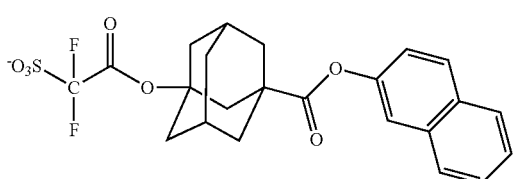
(Ia1-1-12)
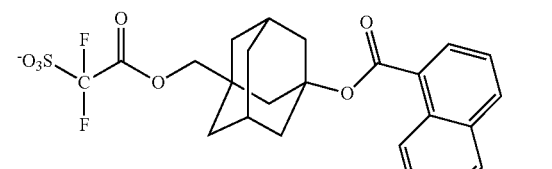
(Ia1-1-13)
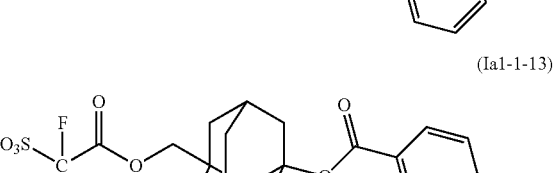
(Ia1-1-14)
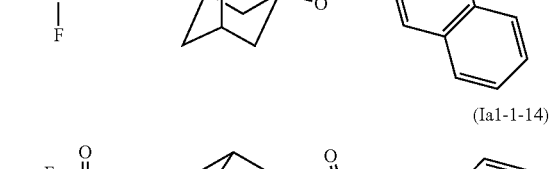
(Ia1-1-15)
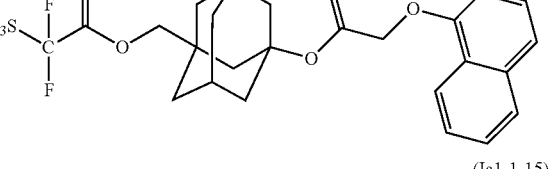
(Ia1-1-16)
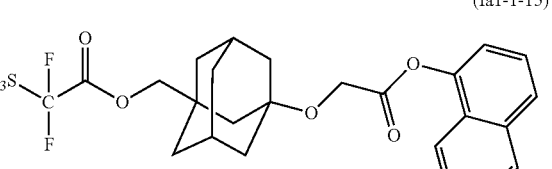
(Ia1-1-17)
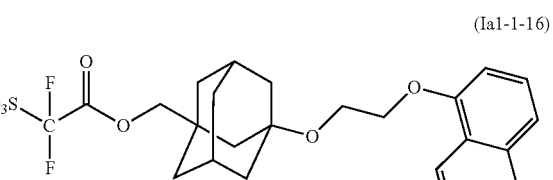

(Ia1-1-18)
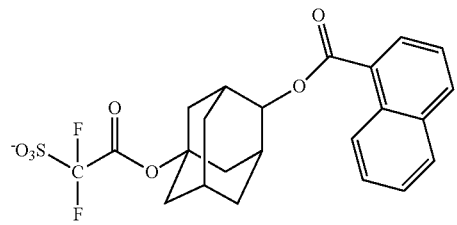

(Ia1-1-19)
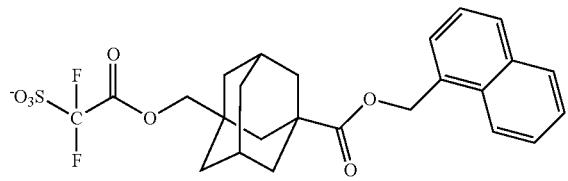

(Ia1-1-20)
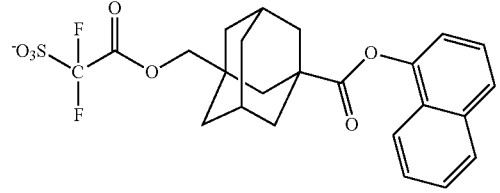

(Ia1-1-21)
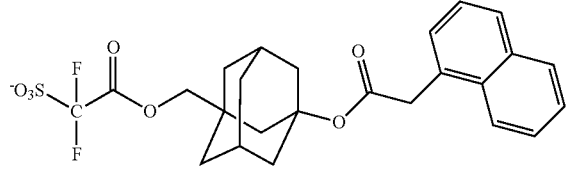

(Ia1-1-22)
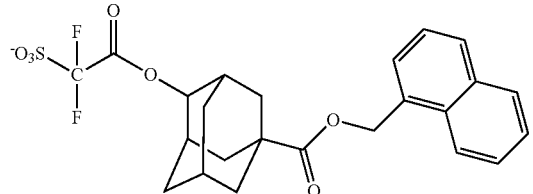

(Ia1-1-23)
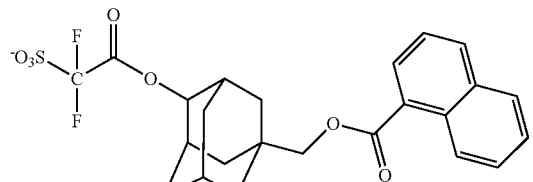

(Ia1-1-24)
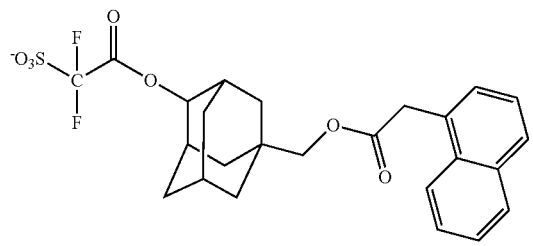

(Ia1-2-1)
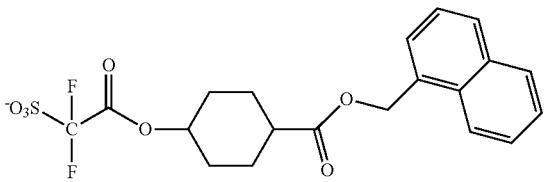

(Ia1-3-1)
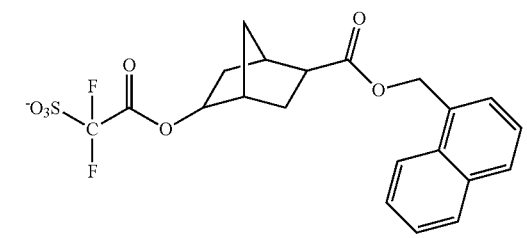

Examples of the organic counter ion represented by $Z^+$ include an onium cation such as a sulfonium cation, an iodonium cation, an ammonium cation, a benzothiazolium cation and a phosphonium cation. As the organic counter ion, sulfonium cation and an iodonium cation are preferable, and an arylsulfonium cation is more preferable. "Arylsulfonium cation" means a cation having at least one aryl group.

Preferable examples of the organic counter ion represented by $Z^+$ include the organic cations represented by the formulae (b2-1), (b2-2), (b2-3) and (b2-4) (hereinafter, the cations represented by the formulae (b2-1), the cations represented by the formulae (b2-2), the cations represented by the formulae (b2-3) and the cations represented by the formulae (b2-4) are sometimes respectively referred to as "cation (b2-1)", "cation (b2-2)", "cation (b2-3)" or "cation (b2-4)"):

(b2-1)

(b2-2)
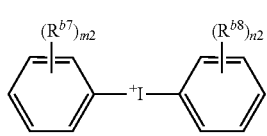

(b2-3)
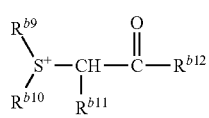

(b2-4)
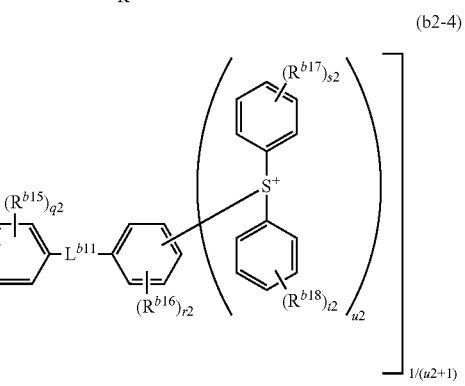

wherein $R^{b4}$, $R^{b5}$ and $R^{b6}$ independently represent a C1-C30 alkyl group one or more hydrogen groups of which may be replaced by a hydroxyl group, a C1-C12 alkoxy group or a C6-C18 aromatic hydrocarbon group, a C3-C18 saturated alicyclic hydrocarbon group one or more hydrogen groups of which may be replaced by a halogen atom, a C2-C4 acyl group or a glycidyloxy group, C6-C18 aromatic hydrocarbon group one or more hydrogen groups of which may be replaced by a halogen atom, a hydroxyl group, a C1-C18 aliphatic hydrocarbon group, a C3-C18 saturated cyclic hydrocarbon group or a C1-C12 alkoxy group, and $R^{b6}$, $R^{b4}$ and $R^{b5}$, $R^{b4}$ and $R^{b6}$ or $R^{b5}$ and $R^{b6}$ can be bonded each other to form a ring containing $S^+$, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ independently represent a C1-C18 alkyl group or a C3-C18 saturated cyclic hydrocarbon group, or $R^{b9}$ and $R^{b10}$ are bonded to form a C2-C11 (preferably C2-C6) ring structure together with the adjacent $S^+$, and one or more —$CH_2$— in the ring may be replaced by —CO—, —O— or —S—, and $R^{b11}$ represents a hydrogen atom, a C1-C18 alkyl group, or a C3-C18 alicyclic hydrocarbon group or a C6-C18 aromatic hydrocarbon group, $R^{b12}$ represents a C1-C12 alkyl group, a C3-C18 alicyclic hydrocarbon group or a C6-C18 aromatic hydrocarbon group one or more hydrogen atoms of which may be replaced by a C1-C12 alkyl group, a C1-C12 alkoxy group, a C3-C18 saturated cyclic hydrocarbon group or a C2-C12 alkylcarbonyloxy group, or $R^{b11}$ and $R^{b12}$ are bonded each other to form a C1-C10 (preferably C1-C5) ring structure together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 aliphatic hydrocarbon group or a C1-C12 alkoxy group, $L^{b11}$ on represents —S— or —O— and o2, p2, s2 and t2 each independently represents an integer of 0 to 5, q2 and r2 each independently represents an integer of 0 to 4, and u2 represents 0 or 1.

The alkyl group represented by $R^{b9}$, $R^{b10}$ or $R^{b11}$ has preferably 1 to 12 carbon atoms. The alicyclic hydrocarbon group represented by $R^{b9}$, $R^{b10}$ or $R^{b11}$ has preferably 4 to 12 carbon atoms.

Preferable examples of the C1-C30 alkyl group represented by $R^{b4}$, $R^{b5}$ or $R^{b6}$ include a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and more preferable examples thereof include a methyl group, an ethyl group, a propyl group and a butyl group.

Preferable examples of the alicyclic hydrocarbon group represented by $R^{b4}$, $R^{b5}$ or $R^{b6}$ include a cyclopentyl group, a cyclohexyl group, a cycloheptyl group, a 2-alkyladamantan-2-yl group, a 1-(adamantan-1-yl)alkane-1-yl group and an isobornyl group, and more preferable examples thereof include a cyclopentyl group and a cyclohexyl group.

Preferable examples of the aromatic group represented by $R^{b4}$, $R^{b5}$ or $R^{b6}$ include a phenyl group, a 4-methylphenyl group, a 4-ethylphenyl group, a 4-tert-butylphenyl group, a 4-cyclohexylphenyl group, a 4-methoxyphenyl group, a biphenyl group a naphthyl group and an anthryl group, and a phenyl group is more preferable.

Examples of the C1-C12 alkoxy group to be contained in $R^{b4}$, $R^{b5}$ and $R^{b6}$ include a methoxy group, an ethoxy group, a propoxy group, a butoxy group, a pentyloxy group, a hexyloxy group, a heptyloxy group, an octyloxy group, a decyloxy group and a dodecyloxy group.

Examples of the halogen atom to be contained in $R^{b4}$, $R^{b5}$ and $R^{b6}$ include a fluorine atom, a chlorine atom, a bromine atom and an iodine atom.

Examples of the C2-C4 acyl group to be contained in $R^{b4}$, $R^{b5}$ and $R^{b6}$ include an acetyl group, a propyonyl group and a butyryl group.

The ring structure containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to S. The ring preferably has 3 to 18 carbon atoms, and more preferably has 4 to 13 carbon atoms.

Preferable examples of the alkyl group represented by $R^{b9}$, $R^{b10}$, $R^{b11}$ or $R^{b12}$ include a methyl group, an ethyl group, a propyl group, an isopropyl group, a butyl group, a sec-butyl group, a tert-butyl group, a pentyl group, a hexyl group, an octyl group and a 2-ethylhexyl group.

Preferable examples of the alicyclic hydrocarbon group represented by $R^{b9}$, $R^{b10}$, $R^{b11}$ or $R^{b12}$ include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkane-1-yl group and an isobornyl group.

Preferable examples of the aromatic group represented by $R^{b11}$ or $R^{b12}$ include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group.

Examples of the alkyl group represented by $R^{b12}$ in which a hydrogen atom has been replaced by an aromatic hydrocarbon group include a benzyl group.

Examples of the C2-C11 divalent group formed by bonding $R^{b9}$ and $R^{b10}$ include a trimethylene group, a tetramethylene group and a pentamethylene group. Examples of the ring structure formed together with the adjacent $S^+$ and the divalent group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 ring formed by bonding $R^{b11}$ and $R^{b12}$ include a methylene group, an ethylene group, a trimethylene group, a tetramethylene group and a pentamethylene group and examples of the ring group include oxocycloheptane ring, oxocyclohexane ring, oxonorbornane ring or oxoadamantane ring.

The organic counter ion represented by the formulae (b2-1), (b2-2), (b2-3) and (b2-4) specifically include a cation mentioned in JP-A-2010-204646.

Among the above-mentioned cations, preferred is the cation represented by the formula (b2-1), and more preferred is the cation represented by the formula (b2-1-1) (hereinafter, such cation is sometimes referred to as "cation (b2-1-1)"), still more preferably a triphenylsulfonium cation, i.e., the group of the formula (b2-1-1) in which v2, w2 and x2 are respectively 0, and a trytolysulfonium cation, i.e., the group of the formula (b2-1-1) in which v2, w2 and x2 are respectively 1 and $R^{b19}$, $R^{b20}$ and $R^{b21}$ are respectively a methyl group.

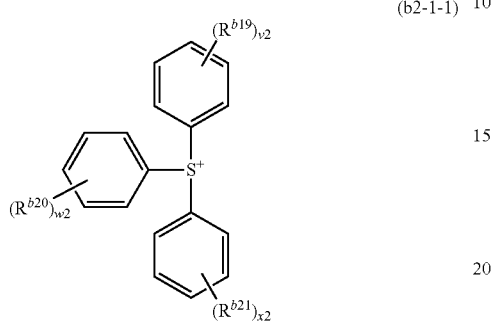

(b2-1-1)

wherein $R^{b19}$, $R^{b20}$ and $R^{b21}$ are independently in each occurrence a halogen atom (preferably a fluorine atom); a hydroxyl group; a C1-C18 alkyl group one or more hydrogen atoms of which may be replaced by a hydroxy atom, a C1-C12 alkoxy group or C6-C18 aromatic hydrocarbon group; a C3-C18 alicyclic hydrocarbon group one or more hydrogen atoms of which may be replaced by a halogen atom, a C2-C4 acyl group or glycidyloxy group; or a C1-C12 alkoxy group;

and $R^{b19}$ and $R^{b20}$, $R^{b21}$ on and $R^{b21}$ or $R^{b20}$ and $R^{b21}$ can be bonded each other to form a single bond, —O— or a C1-C4 aliphatic divalent hydrocarbon group which forms a sulfur containing ring together with S$^+$ and v2, w2 and x2 independently each represent an integer of 0 to 5.

In the formula (b2-1-1), the alkyl group has preferably 1 to 12 carbon atoms, and the saturated cyclic hydrocarbon group has preferably 4 to 18 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5.

It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1-1) include the following.

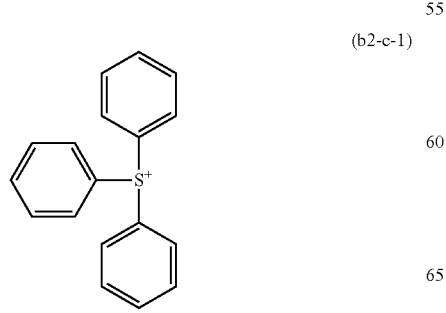

(b2-c-1)

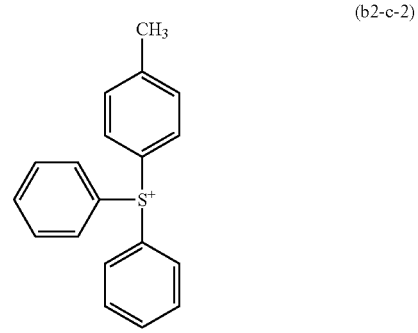

(b2-c-2)

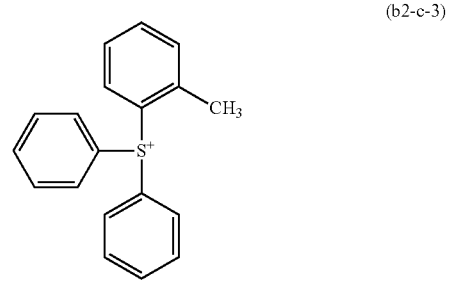

(b2-c-3)

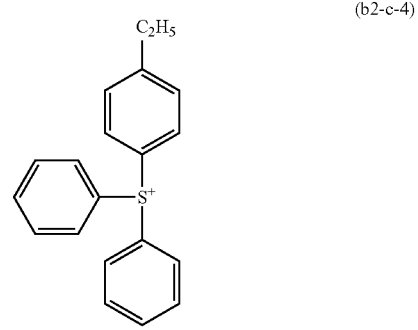

(b2-c-4)

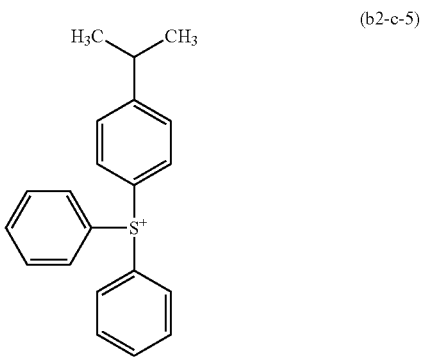

(b2-c-5)

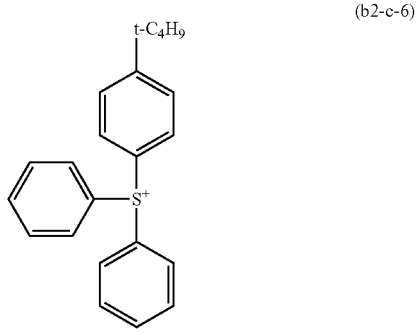

(b2-c-6)

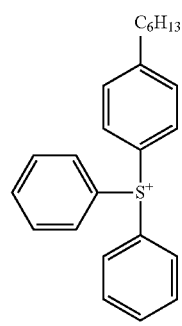
(b2-c-7)
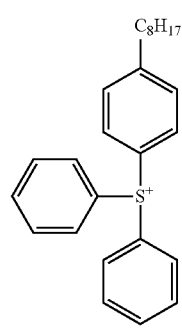
(b2-c-8)
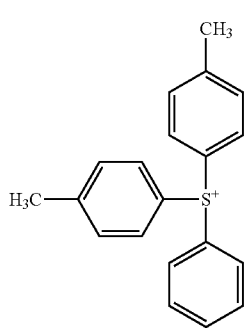
(b2-c-9)
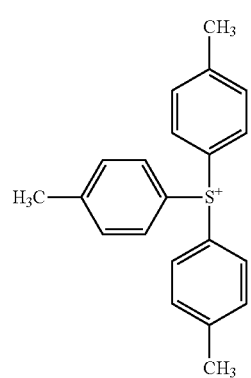
(b2-c-10)
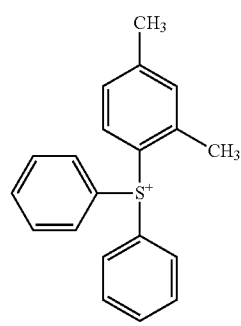
(b2-c-11)
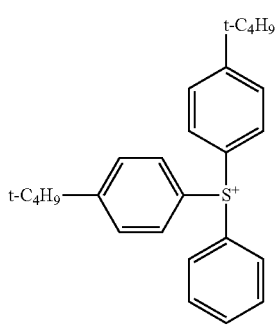
(b2-c-12)
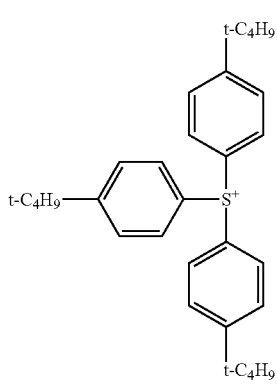
(b2-c-13)
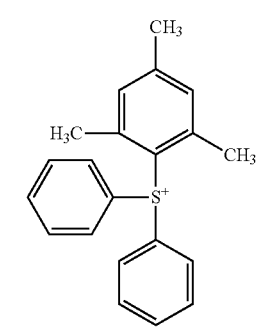
(b2-c-14)

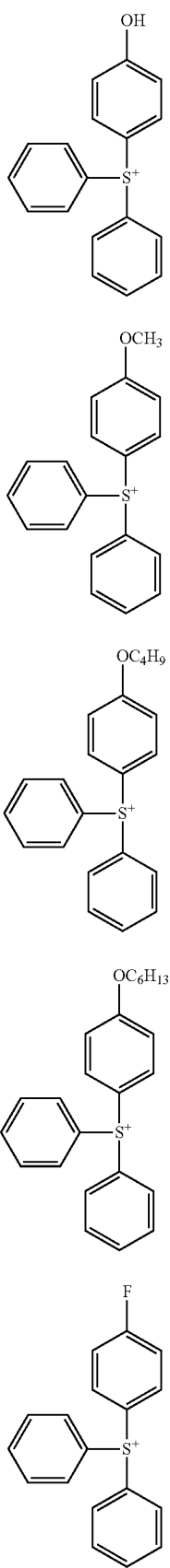
(b2-c-15)
(b2-c-16)
(b2-c-17)
(b2-c-18)
(b2-c-18)
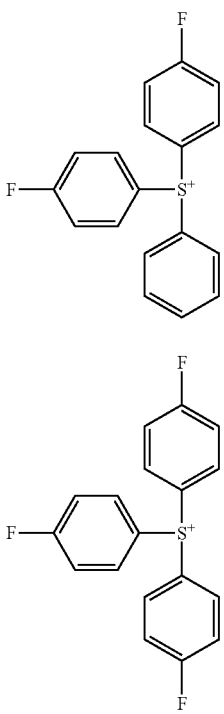
(b2-c-19)
(b2-c-20)
Examples of the cation represented by the formula (b2-1-1) which has the ring containing a sulfur atom include the followings.
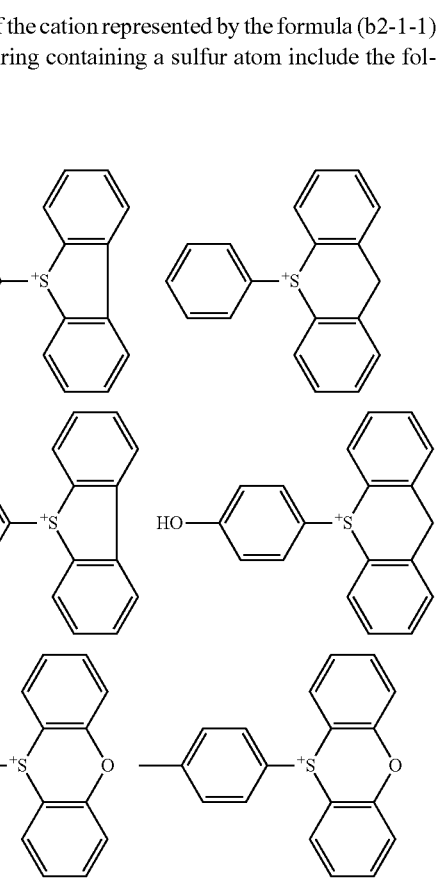

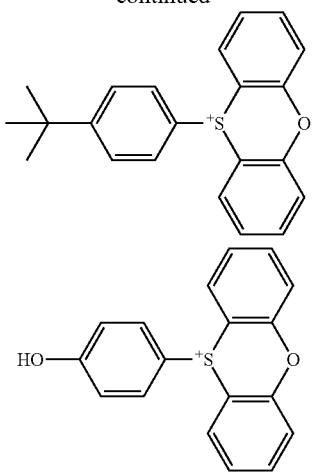

Examples of the cation represented by the formula (b2-1) which has the ring containing a sulfur atom further include the followings.

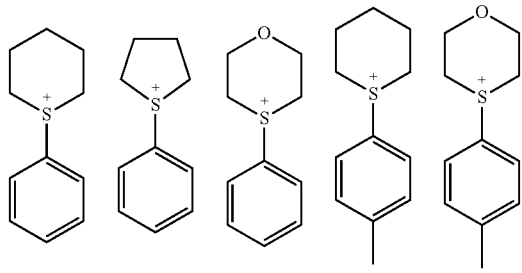

Examples of the cation represented by the formula (b2-2) include the followings.

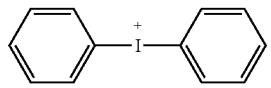

(b2-c-21)

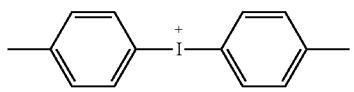

(b2-c-22)

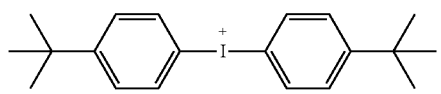

(b2-c-23)

Examples of the cation represented by the formula (b2-3) include the followings.

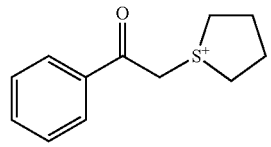

(b2-c-24)

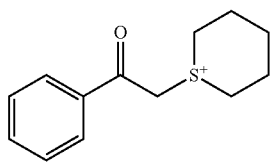

(b2-c-25)

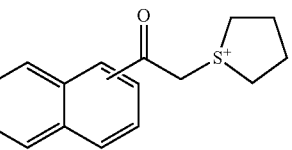

(b2-c-26)

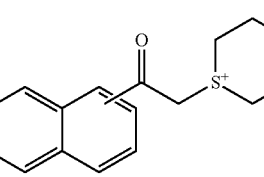

(b2-c-27)

SALT (I) comprises any one of the above-mentioned anions and any one of the above-mentioned organic cations.

Preferable examples of SALT (I) include the salts as shown in the following Tables 1 to 4. In the tables, the symbol of each column refers to that of the formula which represents the corresponding moiety.

TABLE 1

| SALT (I) | anion | cation |
|---|---|---|
| (I-1) | (Ia1-1-1) | (b2-c-1) |
| (I-2) | (Ia1-1-2) | (b2-c-1) |
| (I-3) | (Ia1-1-3) | (b2-c-1) |
| (I-4) | (Ia1-1-4) | (b2-c-1) |
| (I-5) | (Ia1-1-5) | (b2-c-1) |
| (I-6) | (Ia1-1-6) | (b2-c-1) |
| (I-7) | (Ia1-1-7) | (b2-c-1) |
| (I-8) | (Ia1-1-8) | (b2-c-1) |
| (I-9) | (Ia1-1-9) | (b2-c-1) |
| (I-10) | (Ia1-1-10) | (b2-c-1) |
| (I-11) | (Ia1-1-11) | (b2-c-1) |
| (I-12) | (Ia1-1-12) | (b2-c-1) |
| (I-13) | (Ia1-1-13) | (b2-c-1) |
| (I-14) | (Ia1-1-14) | (b2-c-1) |
| (I-15) | (Ia1-1-15) | (b2-c-1) |
| (I-16) | (Ia1-1-16) | (b2-c-1) |
| (I-17) | (Ia1-1-17) | (b2-c-1) |
| (I-18) | (Ia1-1-18) | (b2-c-1) |
| (I-19) | (Ia1-1-19) | (b2-c-1) |
| (I-20) | (Ia1-1-20) | (b2-c-1) |
| (I-21) | (Ia1-2-1) | (b2-c-1) |
| (I-22) | (Ia1-3-1) | (b2-c-1) |
| (I-23) | (Ia1-1-1) | (b2-c-10) |
| (I-24) | (Ia1-1-2) | (b2-c-10) |
| (I-25) | (Ia1-1-3) | (b2-c-10) |
| (I-26) | (Ia1-1-4) | (b2-c-10) |
| (I-27) | (Ia1-1-5) | (b2-c-10) |
| (I-28) | (Ia1-1-6) | (b2-c-10) |
| (I-29) | (Ia1-1-7) | (b2-c-10) |

TABLE 1-continued

| SALT (I) | anion | cation |
|---|---|---|
| (I-30) | (Ia1-1-8) | (b2-c-10) |
| (I-31) | (Ia1-1-9) | (b2-c-10) |
| (I-32) | (Ia1-1-10) | (b2-c-10) |
| (I-33) | (Ia1-1-11) | (b2-c-10) |
| (I-34) | (Ia1-1-12) | (b2-c-10) |
| (I-35) | (Ia1-1-13) | (b2-c-10) |
| (I-36) | (Ia1-1-14) | (b2-c-10) |
| (I-37) | (Ia1-1-15) | (b2-c-10) |
| (I-38) | (Ia1-1-16) | (b2-c-10) |
| (I-39) | (Ia1-1-17) | (b2-c-10) |
| (I-40) | (Ia1-1-18) | (b2-c-10) |
| (I-41) | (Ia1-1-19) | (b2-c-10) |
| (I-42) | (Ia1-1-20) | (b2-c-10) |

TABLE 2

| SALT (I) | anion | cation |
|---|---|---|
| (I-43) | (Ia1-2-1) | (b2-c-10) |
| (I-44) | (Ia1-3-1) | (b2-c-10) |
| (I-45) | (Ia1-1-1) | (b2-c-21) |
| (I-46) | (Ia1-1-2) | (b2-c-21) |
| (I-47) | (Ia1-1-3) | (b2-c-21) |
| (I-48) | (Ia1-1-4) | (b2-c-21) |
| (I-49) | (Ia1-1-5) | (b2-c-21) |
| (I-50) | (Ia1-1-6) | (b2-c-21) |
| (I-51) | (Ia1-1-7) | (b2-c-21) |
| (I-52) | (Ia1-1-8) | (b2-c-21) |
| (I-53) | (Ia1-1-9) | (b2-c-21) |
| (I-54) | (Ia1-1-10) | (b2-c-21) |
| (I-55) | (Ia1-1-11) | (b2-c-21) |
| (I-56) | (Ia1-1-12) | (b2-c-21) |
| (I-57) | (Ia1-1-13) | (b2-c-21) |
| (I-58) | (Ia1-1-14) | (b2-c-21) |
| (I-59) | (Ia1-1-15) | (b2-c-21) |
| (I-60) | (Ia1-1-16) | (b2-c-21) |
| (I-61) | (Ia1-1-17) | (b2-c-21) |
| (I-62) | (Ia1-1-18) | (b2-c-21) |
| (I-63) | (Ia1-1-19) | (b2-c-21) |
| (I-64) | (Ia1-1-20) | (b2-c-21) |
| (I-65) | (Ia1-2-1) | (b2-c-21) |
| (I-66) | (Ia1-3-1) | (b2-c-21) |
| (I-67) | (Ia1-1-1) | (b2-c-24) |
| (I-68) | (Ia1-1-2) | (b2-c-24) |
| (I-69) | (Ia1-1-3) | (b2-c-24) |
| (I-70) | (Ia1-1-4) | (b2-c-24) |
| (I-71) | (Ia1-1-5) | (b2-c-24) |
| (I-72) | (Ia1-1-6) | (b2-c-24) |
| (I-73) | (Ia1-1-7) | (b2-c-24) |
| (I-74) | (Ia1-1-8) | (b2-c-24) |
| (I-75) | (Ia1-1-9) | (b2-c-24) |
| (I-76) | (Ia1-1-10) | (b2-c-24) |
| (I-77) | (Ia1-1-11) | (b2-c-24) |
| (I-78) | (Ia1-1-12) | (b2-c-24) |
| (I-79) | (Ia1-1-13) | (b2-c-24) |
| (I-80) | (Ia1-1-14) | (b2-c-24) |
| (I-81) | (Ia1-1-15) | (b2-c-24) |
| (I-82) | (Ia1-1-16) | (b2-c-24) |
| (I-83) | (Ia1-1-17) | (b2-c-24) |
| (I-84) | (Ia1-1-18) | (b2-c-24) |

TABLE 3

| SALT (I) | anion | cation |
|---|---|---|
| (I-85) | (Ia1-1-19) | (b2-c-24) |
| (I-86) | (Ia1-1-20) | (b2-c-24) |
| (I-87) | (Ia1-2-1) | (b2-c-24) |
| (I-88) | (Ia1-3-1) | (b2-c-24) |
| (I-89) | (Ia1-1-1) | (b2-c-2) |
| (I-90) | (Ia1-1-4) | (b2-c-2) |
| (I-91) | (Ia1-1-6) | (b2-c-2) |
| (I-92) | (Ia1-1-12) | (b2-c-2) |
| (I-93) | (Ia1-1-14) | (b2-c-2) |
| (I-94) | (Ia1-1-15) | (b2-c-2) |
| (I-95) | (Ia1-1-19) | (b2-c-2) |
| (I-96) | (Ia1-1-20) | (b2-c-2) |
| (I-97) | (Ia1-1-1) | (b2-c-6) |
| (I-98) | (Ia1-1-4) | (b2-c-6) |
| (I-99) | (Ia1-1-6) | (b2-c-6) |
| (I-100) | (Ia1-1-12) | (b2-c-6) |
| (I-101) | (Ia1-1-14) | (b2-c-6) |
| (I-102) | (Ia1-1-15) | (b2-c-6) |
| (I-103) | (Ia1-1-19) | (b2-c-6) |
| (I-104) | (Ia1-1-20) | (b2-c-6) |
| (I-105) | (Ia1-1-1) | (b2-c-15) |
| (I-106) | (Ia1-1-4) | (b2-c-15) |
| (I-107) | (Ia1-1-6) | (b2-c-15) |
| (I-108) | (Ia1-1-12) | (b2-c-15) |
| (I-109) | (Ia1-1-14) | (b2-c-15) |
| (I-110) | (Ia1-1-15) | (b2-c-15) |
| (I-111) | (Ia1-1-19) | (b2-c-15) |
| (I-112) | (Ia1-1-20) | (b2-c-15) |
| (I-113) | (Ia1-1-1) | (b2-c-23) |
| (I-114) | (Ia1-1-4) | (b2-c-23) |
| (I-115) | (Ia1-1-6) | (b2-c-23) |
| (I-116) | (Ia1-1-12) | (b2-c-23) |
| (I-117) | (Ia1-1-14) | (b2-c-23) |
| (I-118) | (Ia1-1-15) | (b2-c-23) |
| (I-119) | (Ia1-1-19) | (b2-c-23) |
| (I-120) | (Ia1-1-20) | (b2-c-23) |
| (I-121) | (Ia1-1-1) | (b2-c-26) |
| (I-122) | (Ia1-1-4) | (b2-c-26) |
| (I-123) | (Ia1-1-6) | (b2-c-26) |
| (I-124) | (Ia1-1-12) | (b2-c-26) |
| (I-125) | (Ia1-1-14) | (b2-c-26) |
| (I-126) | (Ia1-1-15) | (b2-c-26) |
| (I-127) | (Ia1-1-19) | (b2-c-26) |
| (I-128) | (Ia1-1-20) | (b2-c-26) |

TABLE 4

| SALT (I) | anion | cation |
|---|---|---|
| (I-129) | (Ia1-1-21) | (b2-c-1) |
| (I-130) | (Ia1-1-22) | (b2-c-1) |
| (I-131) | (Ia1-1-23) | (b2-c-1) |
| (I-132) | (Ia1-1-24) | (b2-c-1) |
| (I-133) | (Ia1-1-21) | (b2-c-10) |
| (I-134) | (Ia1-1-22) | (b2-c-10) |
| (I-135) | (Ia1-1-23) | (b2-c-10) |
| (I-136) | (Ia1-1-24) | (b2-c-10) |
| (I-137) | (Ia1-1-21) | (b2-c-21) |
| (I-138) | (Ia1-1-22) | (b2-c-21) |
| (I-139) | (Ia1-1-23) | (b2-c-21) |
| (I-140) | (Ia1-1-24) | (b2-c-21) |
| (I-141) | (Ia1-1-21) | (b2-c-24) |
| (I-142) | (Ia1-1-22) | (b2-c-24) |
| (I-143) | (Ia1-1-23) | (b2-c-24) |
| (I-144) | (Ia1-1-24) | (b2-c-24) |

Among them, the following salts are preferable.
(I-1)
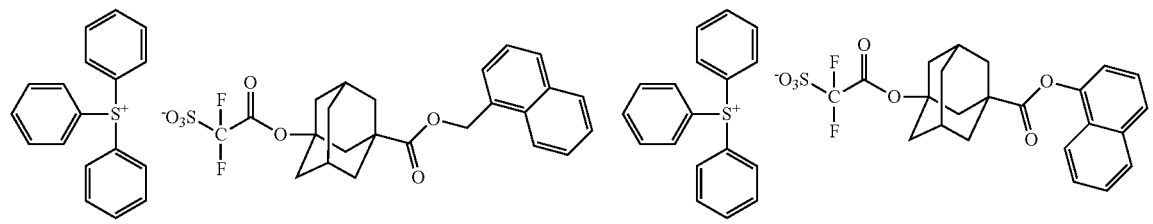
(I-4)
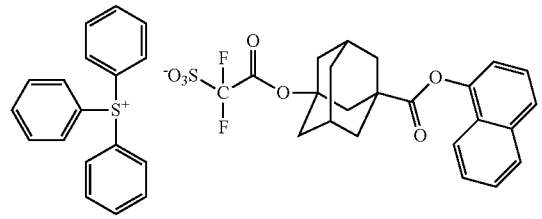
(I-6)
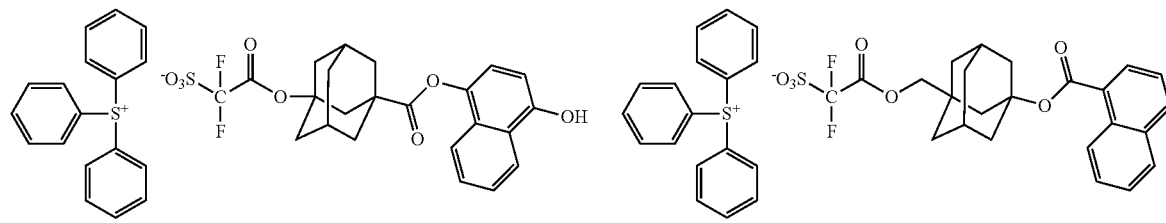
(I-12)
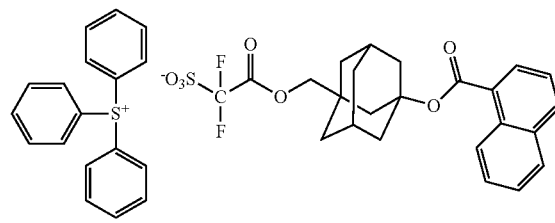
(I-14)
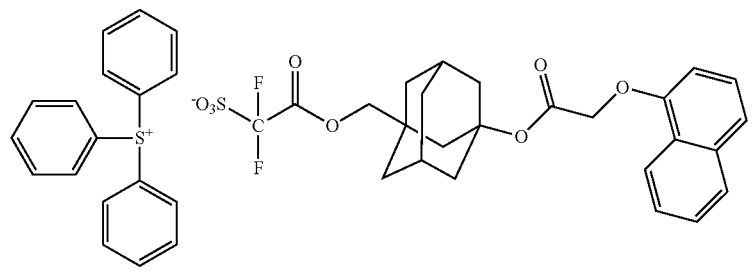
(I-15)
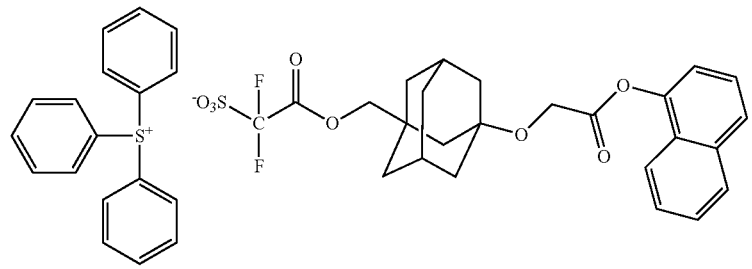
(I-19)
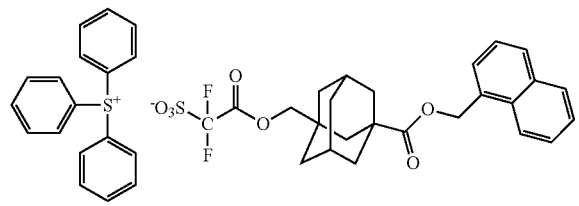
(I-20)
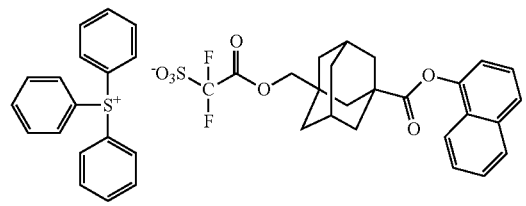
(I-129)
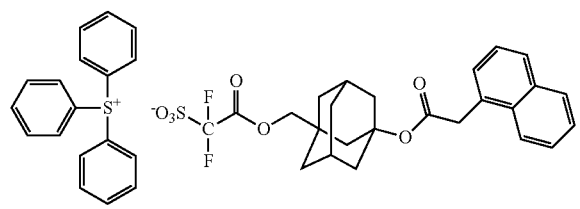
(I-130)
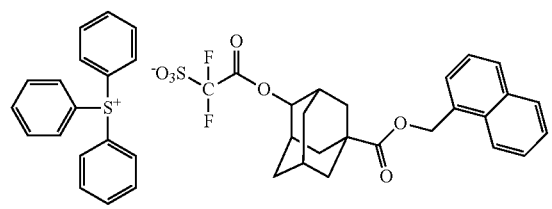

-continued
(I-131)
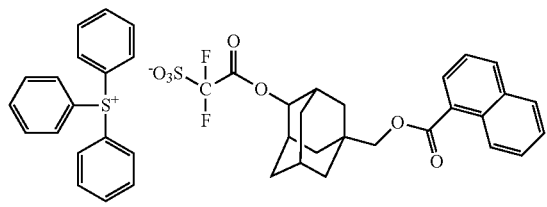
(I-132)
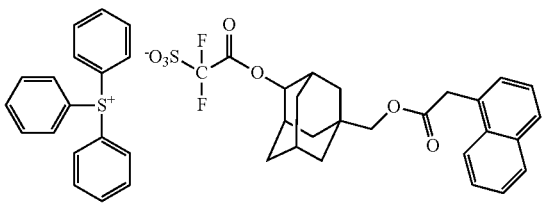
(I-23)
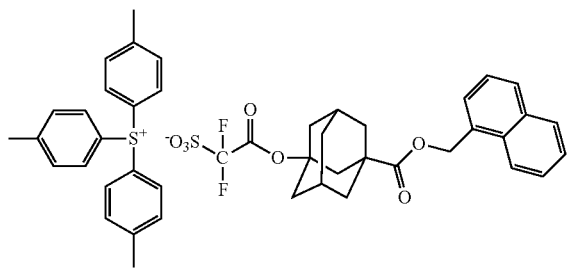
(I-26)
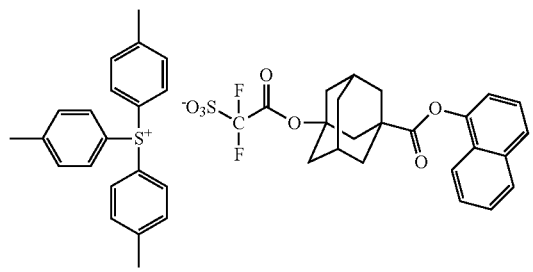
(I-28)
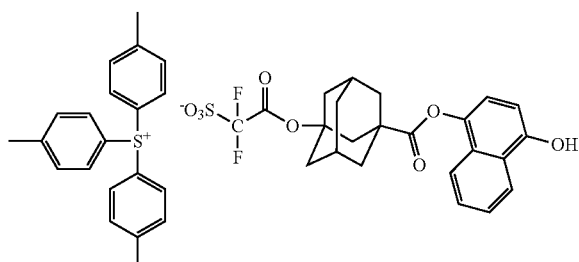
(I-34)
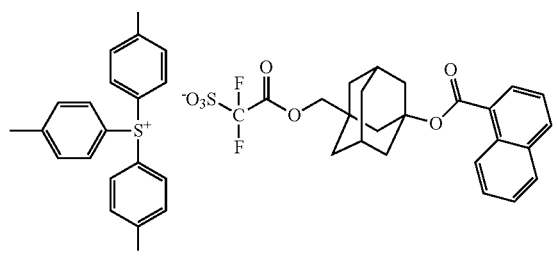
(I-36)
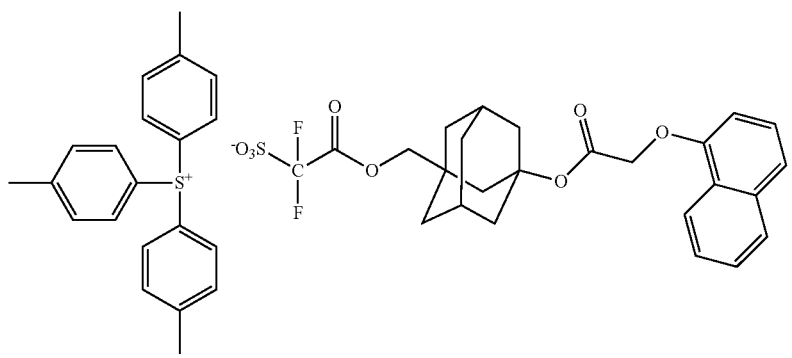
(I-37)
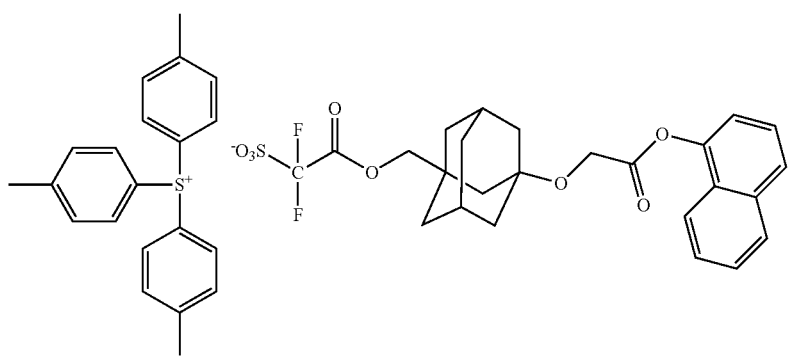

-continued
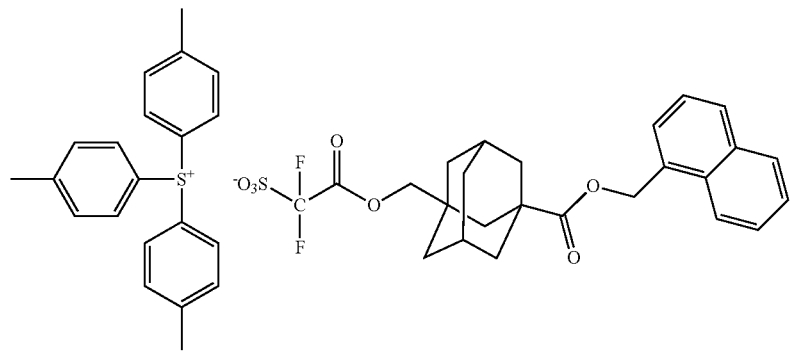
(I-41)
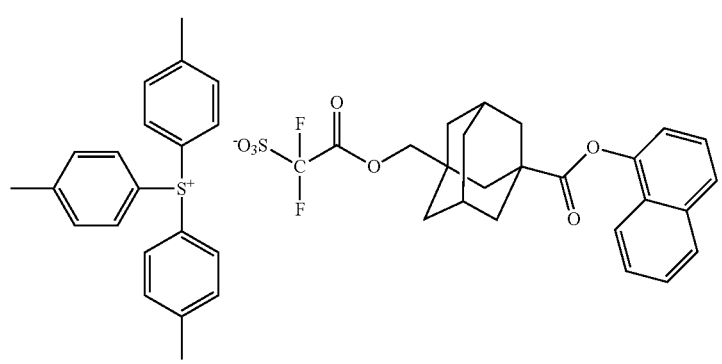
(I-42)
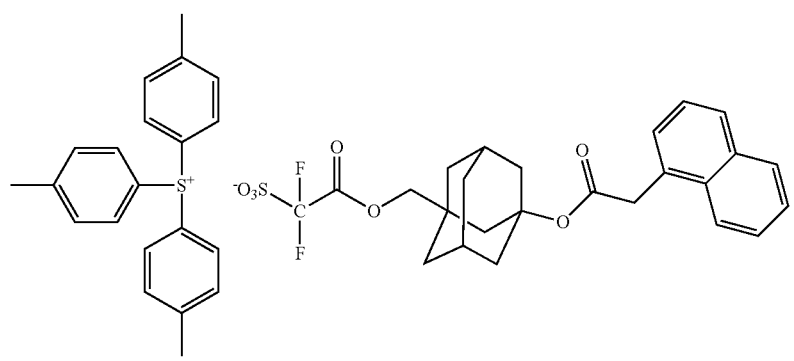
(I-133)
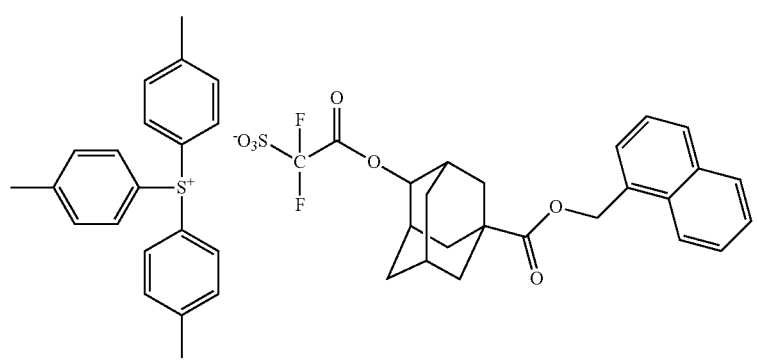
(I-134)

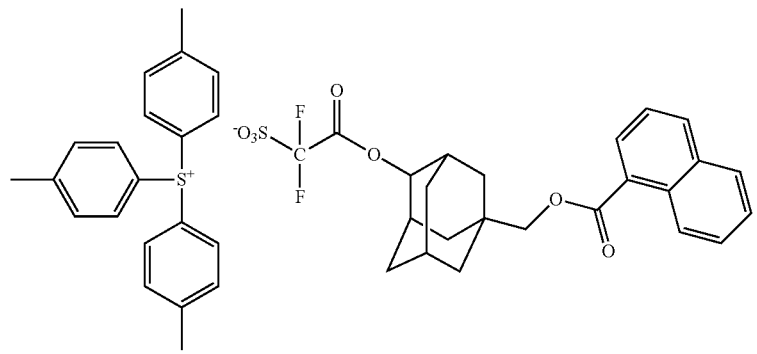
(I-135)
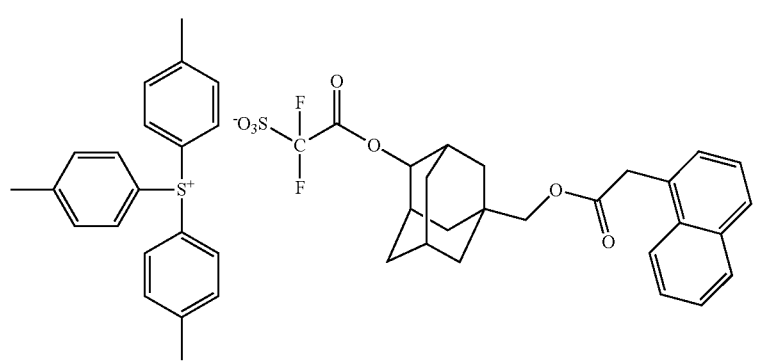
(I-136)
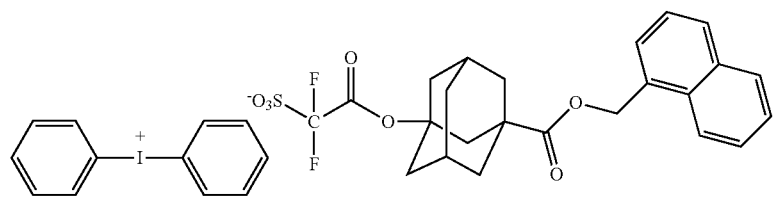
(I-45)
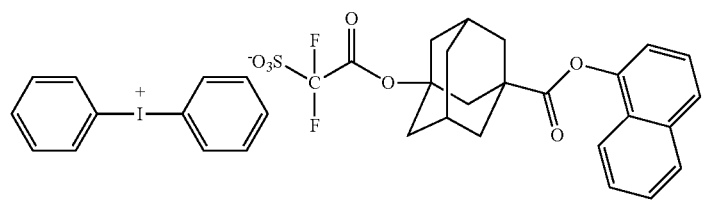
(I-48)
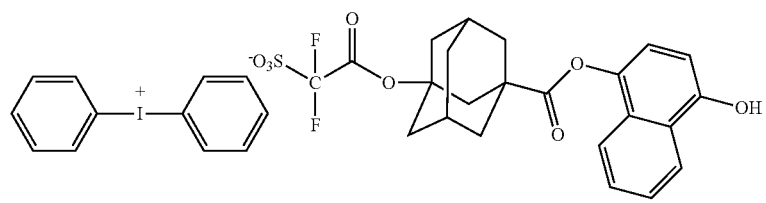
(I-50)
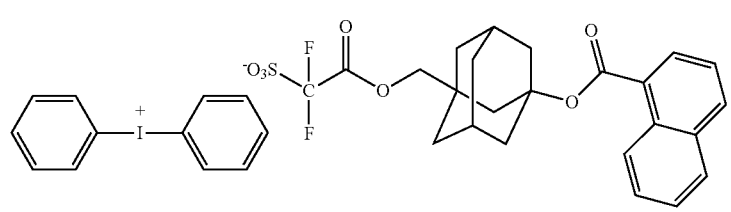
(I-56)

-continued
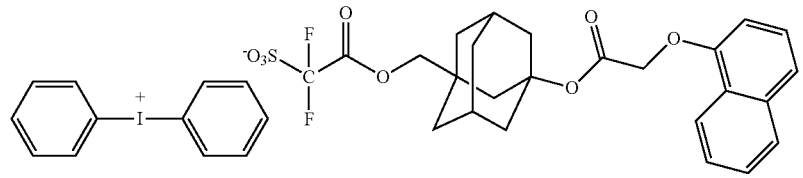
(I-58)
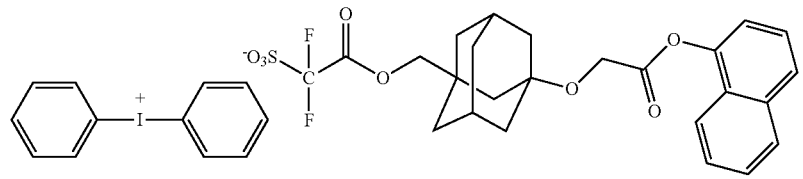
(I-59)
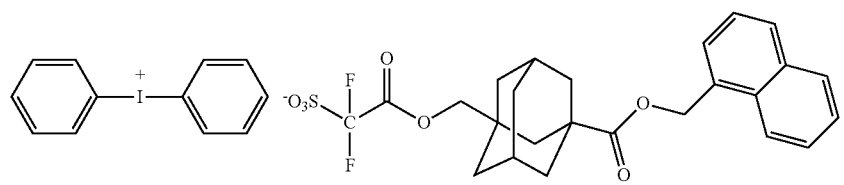
(I-63)
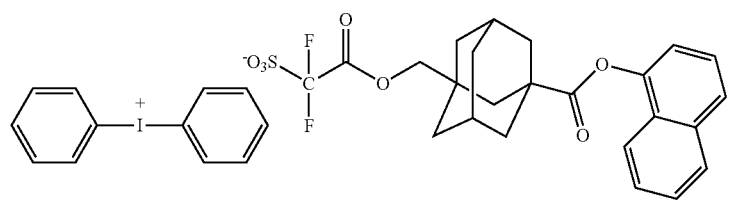
(I-64)
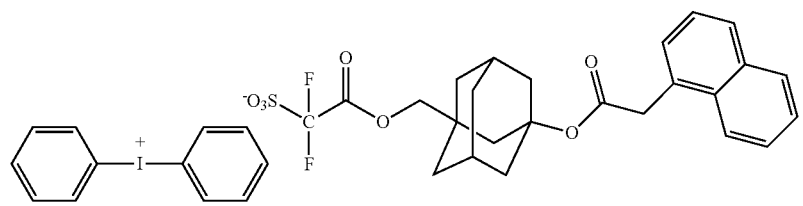
(I-137)
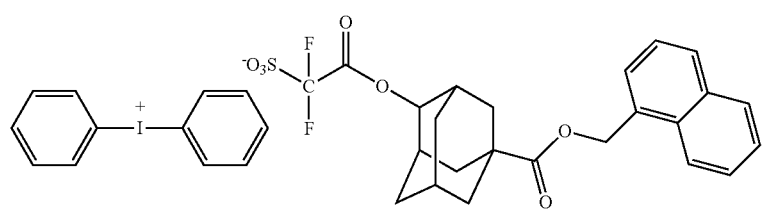
(I-138)
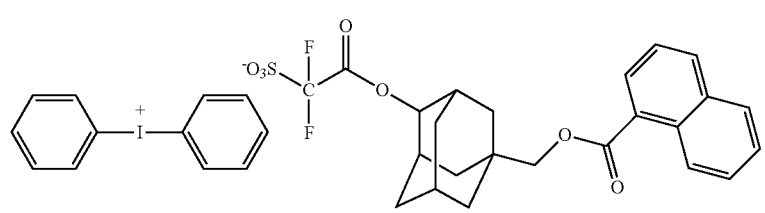
(I-139)

-continued
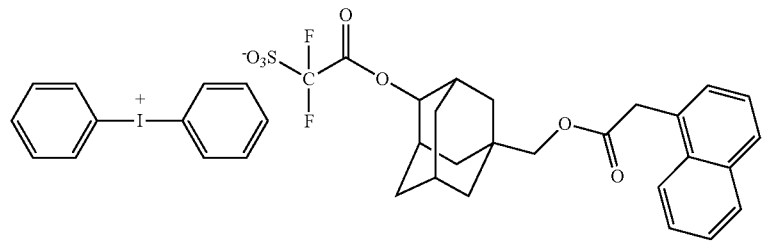
(I-140)
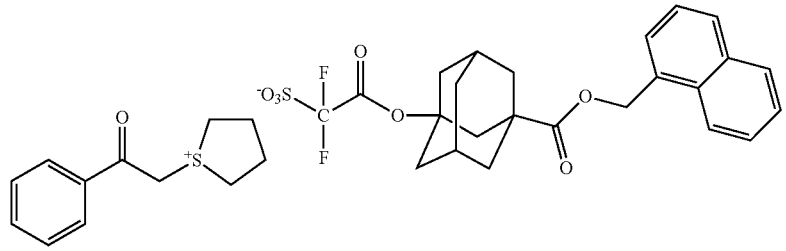
(I-67)
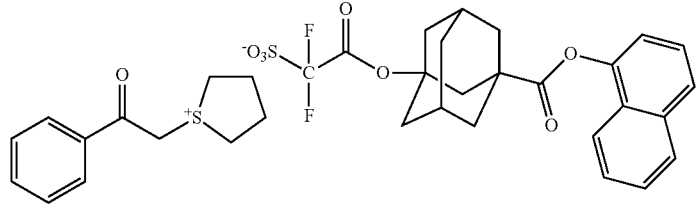
(I-70)
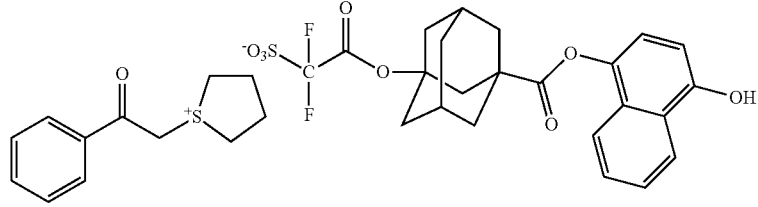
(I-72)
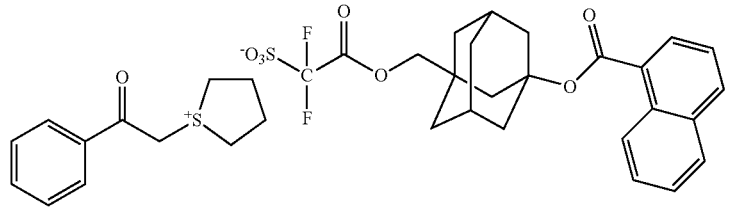
(I-78)
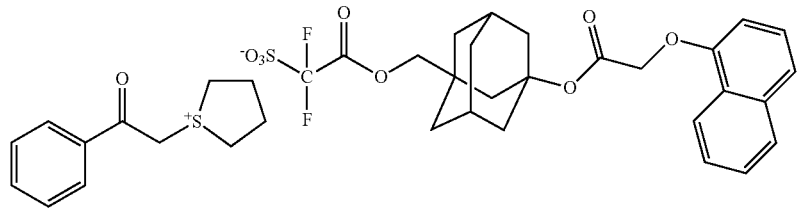
(I-80)
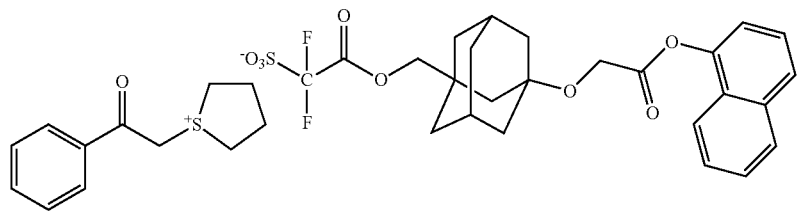
(I-81)

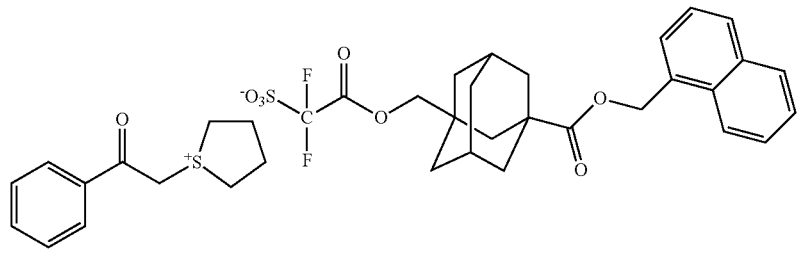
(I-85)
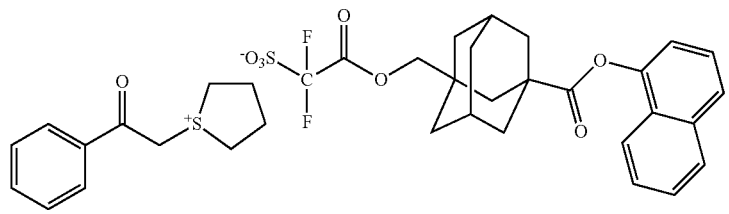
(I-86)
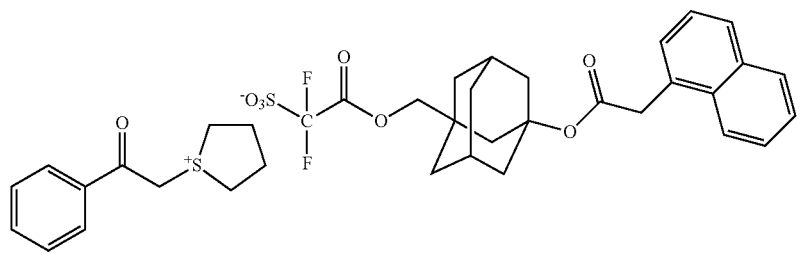
(I-141)
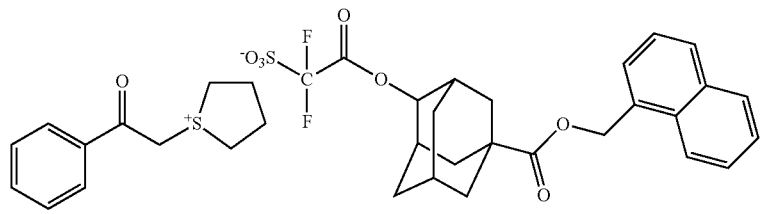
(I-142)
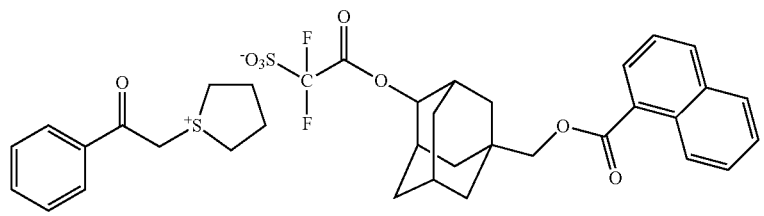
(I-143)
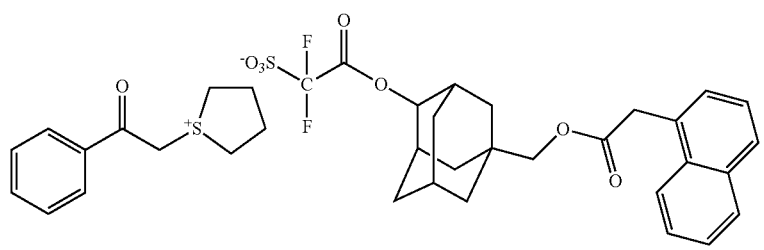
(I-144)

The process for producing SALT (I) will be illustrated.
For example, a salt represented by the formula (b1):

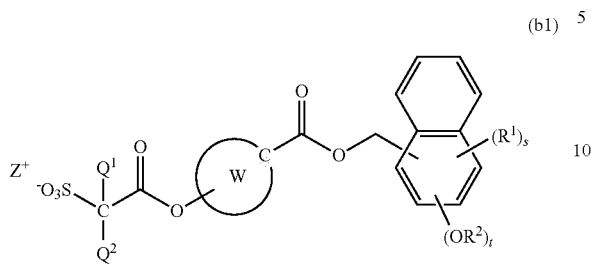
(b1)

wherein $Q^1$, $Q^2$, $R^1$, $R^2$, ring W, $Z^+$, s and t are the same as defined above, can be produced by reacting a salt represented by the formula (b1-a) with a compound represented by the formula (b1-b) in a solvent. Examples of the solvent include acetonitrile.

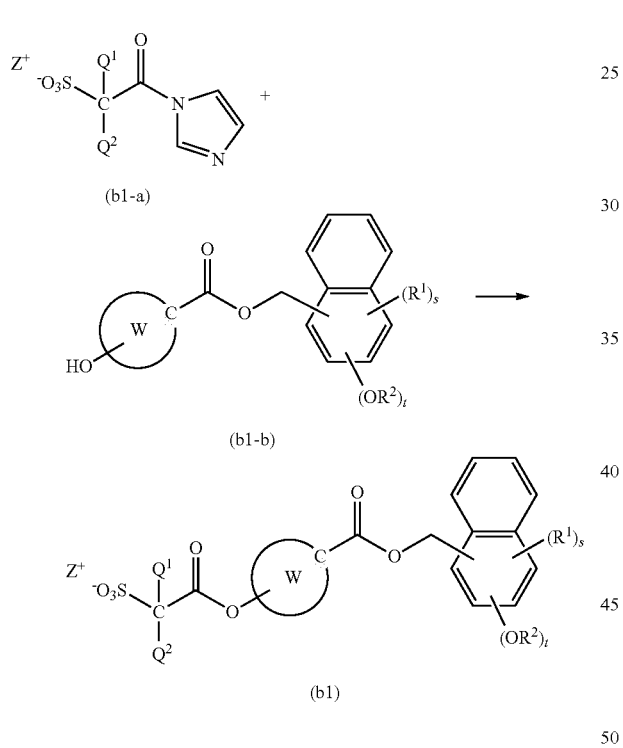

wherein $Q^1$, $Q^2$, $R^2$, ring W, $Z^+$, s and t are the same as defined above.

The salt represented by the formula (b1-a) can be produced by reacting a salt represented by the formula (b1-c) with a compound represented by the formula (b1-d) in a solvent. Examples of the solvent include acetonitrile.

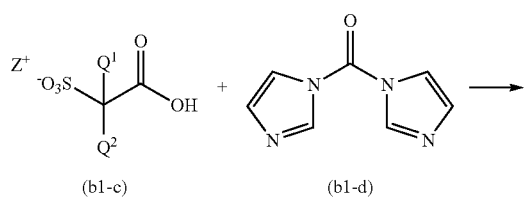

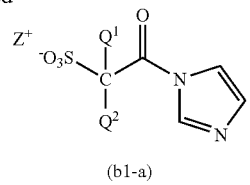
(b1-a)

The salt represented by the formula (b1-c) can be produced, for example, according to the method described in JP 2008-13551 A.

The compound represented by the formula (b1-b) can be produced by reacting a salt represented by the formula (b1-e) with a compound represented by the formula (b1-f) in a solvent. Examples of the solvent include chloroform.

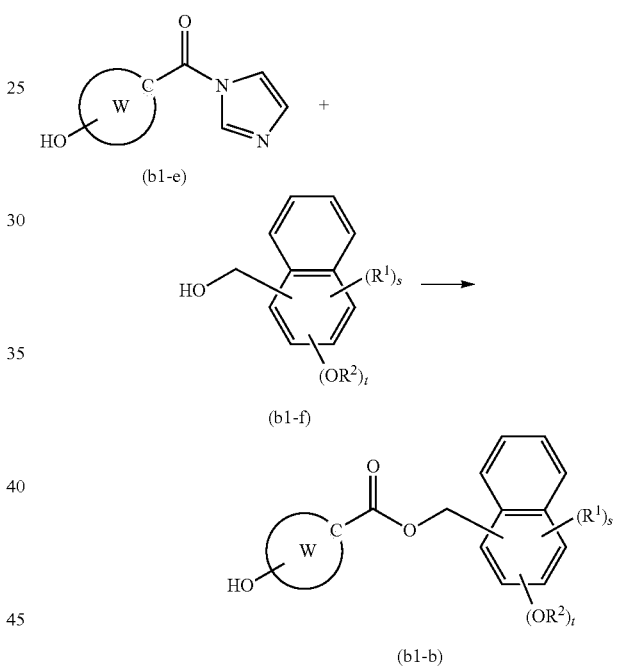

Examples of the compound represented by the formula (b1-f) include 1-naphtalenemethanol.

The compound represented by the formula (b1-e) can be produced by reacting a salt represented by the formula (b1-g) with a compound represented by the formula (b1-d) in a solvent. Examples of the solvent include chloroform.

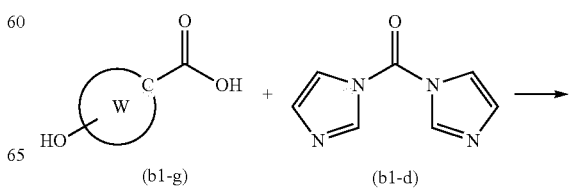

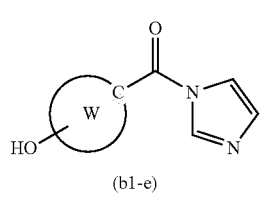
(b1-e)

Examples of the compound represented by the formula (b1-g) include 3-hydroxy-1-adamantane carboxylate.

Next, the acid generator of the present invention will be illustrated.

The acid generator of the present invention comprises SALT (I). The acid generator of the present invention can contain two or more kinds of SALT (I). The acid generator of the present invention may consist of SALT (I). The acid generator of the present invention can contain one or more known acid generators other than SALT (I) in addition to SALT (I). The acid generator of the present invention contains SALT (I) in an effective amount. Hereinafter, known acid generators other than SALT (I), which are used for the present invention, are sometimes referred to as "acid generator (B)".

Preferable examples of the acid generator other than SALT (I) include salts represented by the formulae (B1-1) to (B1-17), the salt containing a triphenylsulfonium cation or a tri-tolylsulfonium cation is more preferable, and the salts represented by the formulae (B1-1), (B1-2), (B1-3), (B1-6), (B1-11), (B1-12), (B1-13) and (B1-14) are especially preferable.

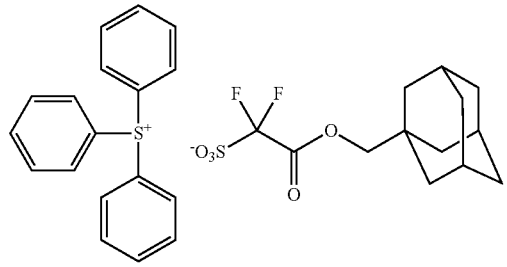
(B1-1)

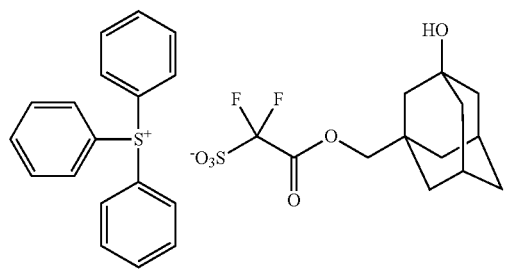
(B1-2)

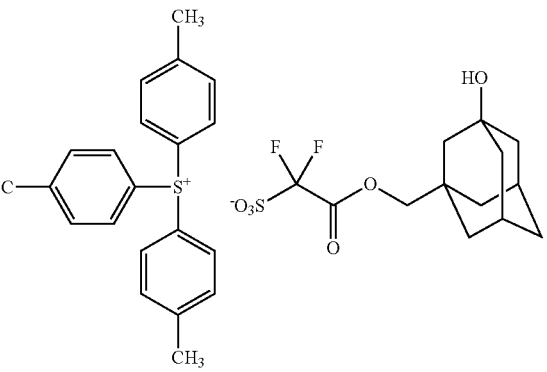
(B1-3)

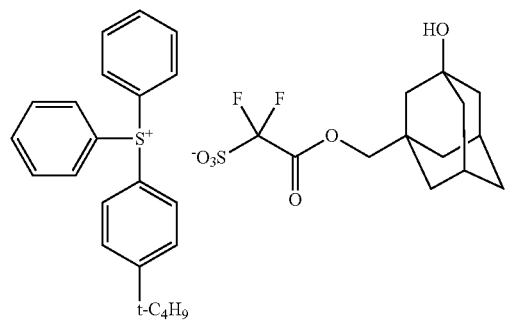
(B1-4)

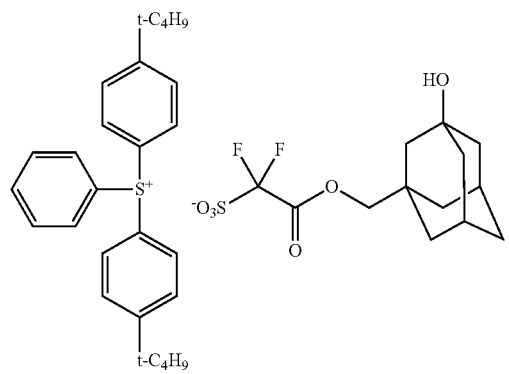
(B1-5)

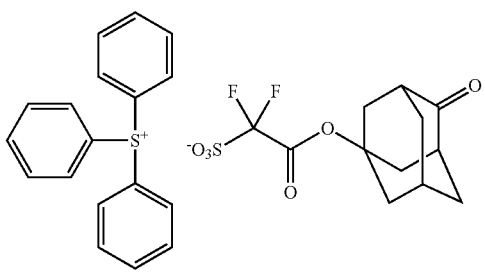
(B1-6)

-continued
(B1-7)
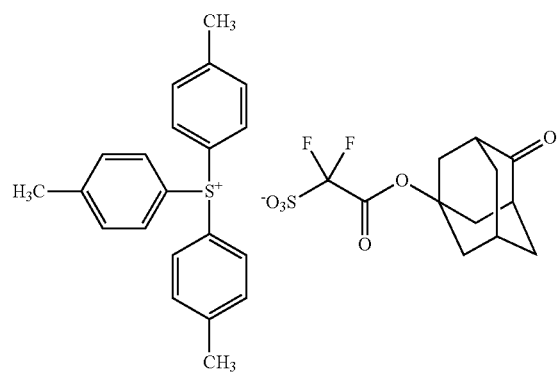
(B1-8)
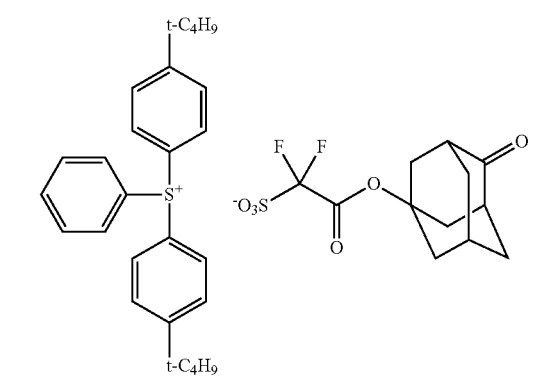
(B1-9)
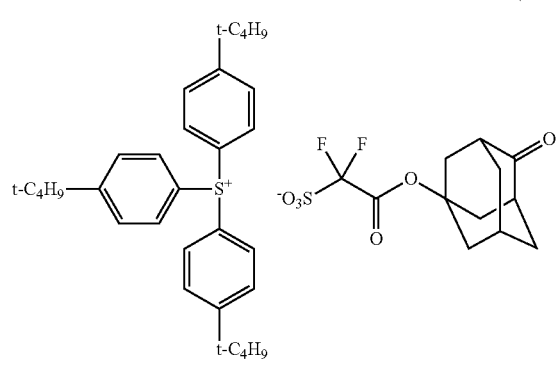
(B1-10)
-continued
(B1-11)
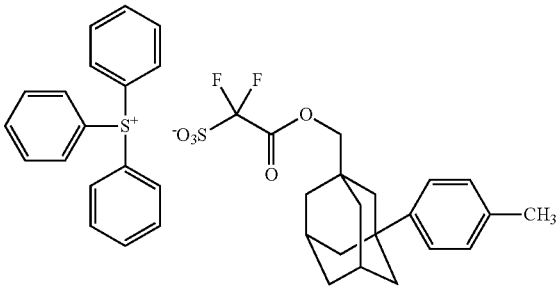
(B1-12)
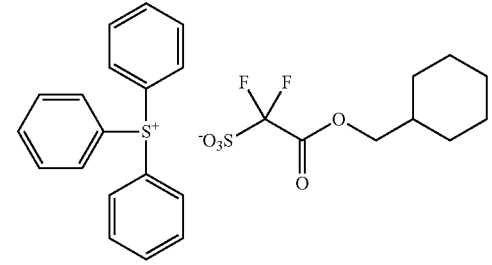
(B1-13)
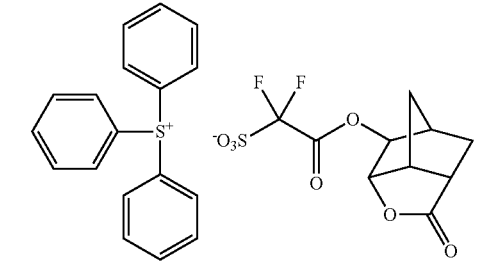
(B1-14)
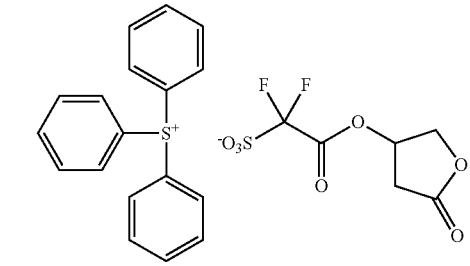
(B1-15)
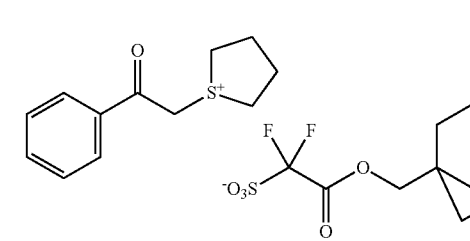
(B1-16)
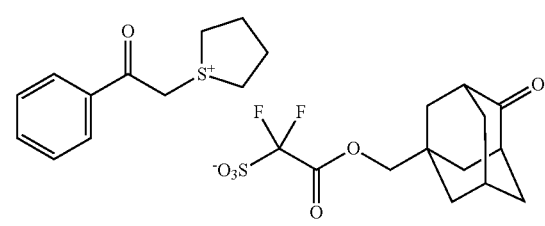

(B1-17)

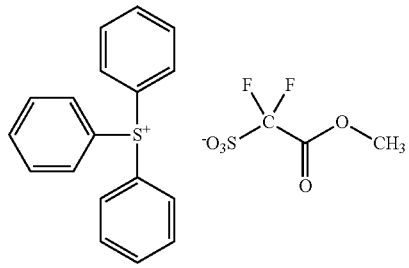

When the acid generator of the present invention contains SALT (I) and the acid generator other than SALT (I), the content of SALT (I) is preferably 10 parts by weight or more and more preferably 30 parts by weight or more per 100 parts by weight of the acid generator of the present invention, and the content of SALT (I) is preferably 90 parts by weight or less and more preferably 70 parts by weight or less per 100 parts by weight of the acid generator of the present invention.

Next, the photoresist composition of the present invention will be illustrated.

The photoresist composition of the present invention comprises the acid generator of the present invention and a resin.

The resin to be used for the present invention has an acid-labile group, which is insoluble or poorly soluble in an aqueous alkali solution but becomes soluble in an aqueous alkali solution by the action of an acid. Hereinafter such resin is sometimes referred to as "resin (A)".

The resin (A) has one or more of moieties in which hydrophilic groups attached to a protective group capable of being removed from the hydrophilic groups by contacting an acid. When the resin (A) contacts an acid, the protective group of the resin (A) is removed from the resin thereby to make hydrophilic groups not protected and then to form a resin capable of being soluble in an aqueous alkali solution. Such moieties in which hydrophilic groups attached to the above-mentioned protective group are sometimes referred to as "acid-labile group". The hydrophilic group includes hydroxyl group or carboxy group, preferably carboxy group.

The resin (A) can be produced by polymerizing a monomer having an acid-labile group. Hereinafter, such monomer is sometimes referred to as "monomer (a1)". One or more kinds of monomer (a1) can be used for the production of resin (A).

An acid-labile group which has a carboxy group as the hydrophilic group includes esters of tertiary alcohols such as a group in which a hydrogen group has been replaced by an organic group, the tertiary carbon atom of organic group binds to an oxy group.

Among such acid-labile groups, examples of the acid-labile group include a group represented by the formula (1):

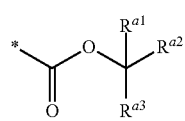

(1)

wherein $R^{a1}$, $R^{a2}$ and $R^{a3}$ independently each represent a C1-C8 alkyl group or a C3-C20 alicyclic hydrocarbon group, $R^{a1}$ and $R^{a2}$ can be bonded each other to form a C3-C20 ring together with a carbon atom to which $R^{a1}$ and $R^{a2}$ are bonded, and one or more —CH$_2$— in the alkyl group, the alicyclic hydrocarbon group and the ring can be replaced by —O—, —S— or —CO—, and * represents a binding position.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

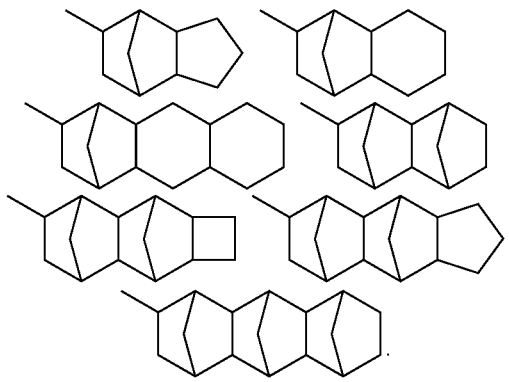

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

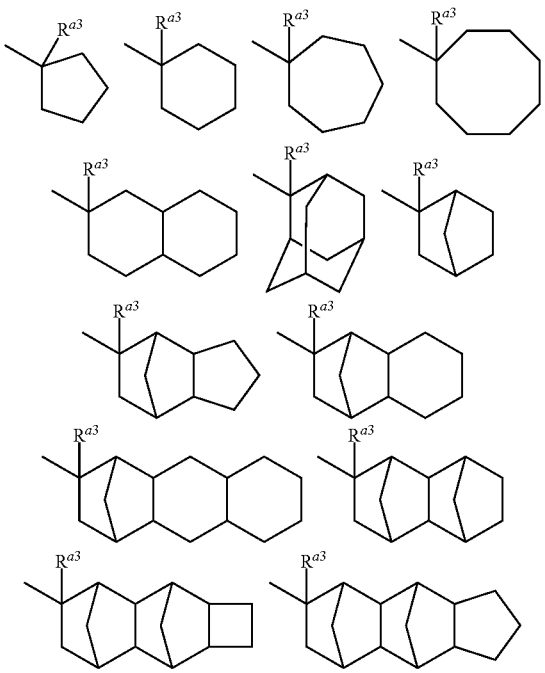

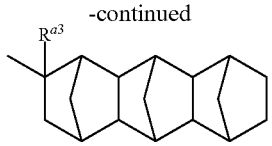

wherein $R^{a3}$ is the same as defined above.

The group represented by the formula (1) specifically includes 1,1-dialkylalkoxycarbonyl group (in the formula, $R^{a1}$, $R^{a2}$ and $R^{a1}$ independently each represent a C1-C8 alkyl group), preferably tert-(butoxy) carbonyl group, 2-(adamantan-2-yl)-1-alkylalkoxycarbonyl group (in the formula, $R^{a1}$ and $R^{a2}$ are bonded each other to form a C3-C20 ring together with a carbon atom to which they are bonded, and $R^{a3}$ is a C1-C8 alkyl group), and 1-(adamantan-1-yl)-1-alkylalkoxycarbonyl group (in the formula, $R^{a1}$ and $R^{a2}$ are C1-C8 alkyl groups, $R^{a3}$ is an adamantyl group).

An acid-labile group which has a hydroxy group as the hydrophilic group includes those in which a hydrogen group of the hydroxy group has been replaced by an organic group to have an acetal or ketal structure.

Among such acid-labile groups, preferred examples of the acid-labile group include a group represented by the formula (2):

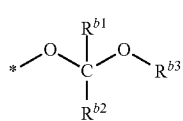

(2)

wherein $R^{b1}$ and $R^{b2}$ independently each represent a hydrogen atom or a C1-C12 hydrocarbon group, and $R^{b3}$ represents a C1-C20 hydrocarbon group, and $R^{b2}$ and $R^{b3}$ can be bonded each other to form a C3-C20 ring together with the carbon atom and the oxygen atom to which they are bonded, and one or more —CH$_2$— in the hydrocarbon group and the ring can be replaced by —O—, —S— or —CO—, and * represents a binding position.

Examples of the hydrocarbon group in the formula (2) include an aliphatic hydrocarbon group, an alicyclic hydrocarbon group and an aromatic hydrocarbon group. Examples of the aliphatic hydrocarbon group and the alicyclic hydrocarbon group include the same as described above. Examples of the aromatic hydrocarbon group include an aryl group such as a phenyl group, a naphthylgroup, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{b1}$ and $R^{b2}$ is a hydrogen atom.

Examples of the group represented by the formula (2) include the following.

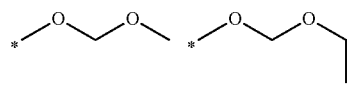

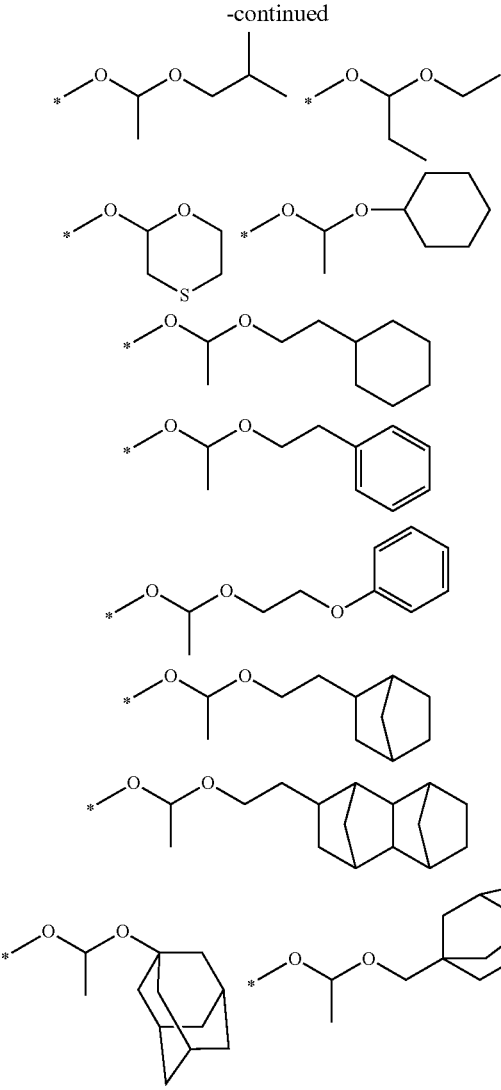

The monomer (a1) is preferably a compound having an acid-labile group and a carbon-carbon double bond, more preferably an acrylate monomer having an acid-labile group or a methacryalte monomer having an acid-labile group.

The monomer (a1) is preferably a compound having the group represented by the formula (1) and/or (2) and a carbon-carbon double bond, and more preferably an acrylate monomer having the group represented by the formula (1) or a methacryalte monomer having the group represented by the formula (1).

Among acrylate monomers having the group represented by the formula (1) and methacryalte monomers having the group represented by the formula (1), preferred are monomers in which the group represented by the formula (1) has a C5-C20 alicycle. When a photoresist composition has a resin (A) obtained by polymerizing a monomer (a1) and the monomer (a1) has such bulky alicycle at a side chain, the photoresist composition with better DOF (forcus margin) can be obtained from the photoresist composition.

Preferable examples of the compound having an acid-labile group include monomers represented by the formulae (a1-1) and (a1-2):

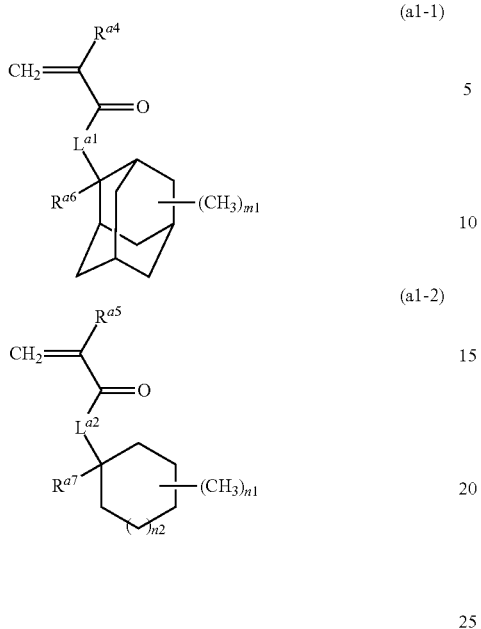

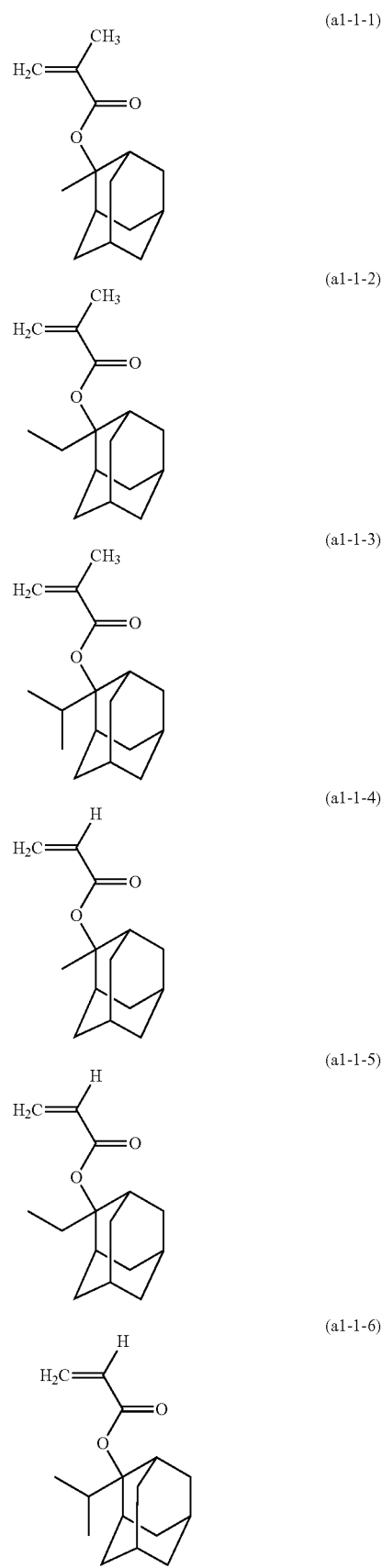

wherein $L^{a1}$ and $L^{a2}$ each independently represents *—O— or *—O—$(CH_2)_{k1}$—CO—O— in which k1 represents an integer of 1 to 7 and represents a binding position to —CO—, $R^{a4}$ and $R^{a5}$ each independently represents a hydrogen atom or a methyl group, $R^{a6}$ and $R^{a7}$ each independently represents a C1-C8 alkyl group or a C3-C10 alicyclic hydrocarbon group, and m1 represents an integer of 0 to 14, n1 represents an integer of 0 to 10, and n2 represents 0 or 1.

In the formulae (a1-1) and (a1-2), —$(CH_2)_{m1}$ represents m1 of methyl groups each binding to carbon atoms of the adamantane ring.

Each of $L^{a1}$ and $L^{a2}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—.

$R^{a4}$ and $R^{a5}$ are preferably methyl groups.

For $R^{a6}$ and $R^{a7}$, the alkyl group preferably includes a methyl group, an ethyl group, a propyl group, a butyl group, a pentyl group, a hexyl group, a heptyl group and an octyl group, more preferably a C1-C6 alkyl group.

Examples of the alicyclic hydrocarbon group include a methylcyclohexyl group, a dimethylcyclohexyl group, a cycloheptyl group, a methylcycloheptyl group and a methylnorbornyl group. The alicyclic hydrocarbon group preferably has 3 to 8 carbon atoms and more preferably 3 to 6 carbon atoms. In the formula (a1-1), m1 is preferably an integer of 0 to 3, and is more preferably 0 or 1. In the formula (a1-2), n1 is preferably an integer of 0 to 3, and is more preferably 0 or 1.

Examples of the monomer represented by the formula (a1-1) include the monomers mentioned in JP2010-A-204646. Among these monomers, preferred are those represented by the formulae (a1-1-1), (a1-1-2), (a1-1-3), (a1-1-4), (a1-1-5) and (a1-1-6), and more preferred are those represented by the formulae (a1-1-1), (a1-1-2) and (a1-1-3).

Examples of the monomer represented by the formula (a1-2) include 1-ethyl-1-cyclopentan-1-yl (meth)acrylate, 1-ethyl-1-cyclohexan-1-yl (meth)acrylate, 1-ethyl-1-cycloheptan-1-yl (meth)acrylate, 1-methyl-1-cyclopentan-1-yl (meth)acrylate and 1-isopropylcyclopentan-1-yl (meth)acrylate. Preferred are those represented by the formulae (a1-2-1), (a1-2-2), (a1-2-3), (a1-2-4), (a1-2-5) and (a1-2-6), more preferred are those represented by the formulae (a1-2-3) and (a1-2-4), and still more preferred are the compound represented by the formula (a1-2-3).

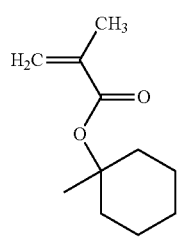
(a1-2-1)

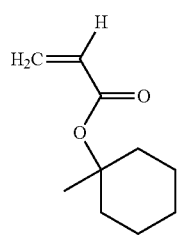
(a1-2-2)

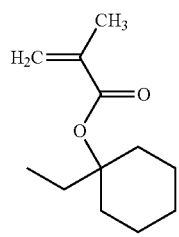
(a1-2-3)

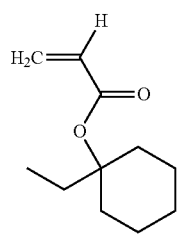
(a1-2-4)

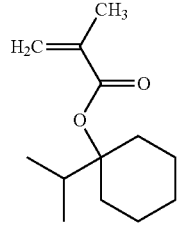
(a1-2-5)

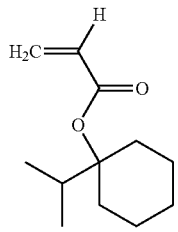
(a1-2-6)

When the resin contains the structural unit derived form the monomer represented by the formula (a1-1) and/or the monomer represented by the formula (a1-2), the content of the structural unit derived from a monomer having an acid-labile group in the resin is usually 10 to 95% by mole, preferably 15 to 90% by mole and more preferably 20 to 85% by mole based on 100% by mole of all the structural units of the resin.

Other examples of the monomer having an acid-labile group and carbon-carbon double bonds include a monomer represented by the formula (a1-3) which has a norbornene ring:

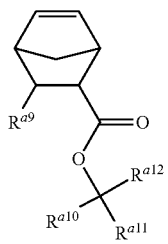
(a1-3)

wherein $R^{a9}$ represents a hydrogen atom, a C1-C3 alkyl group, a carboxyl group, a cyano group or a —COOR$^{a13}$ group in which R$^{an}$ represents a C1-C8 alkyl group, a C3-C20 alicyclic hydrocarbon group, or a group consisting of the C1-C8 alkyl group and the C3-C20 alicyclic hydrocarbon group, and the C1-C8 alkyl group and the C3-C20 alicyclic hydrocarbon group can have one or more hydroxyl groups, and one or more —CH$_2$— in the C1-C8 alkyl group and the C3-C20 alicyclic hydrocarbon group can be replaced by —O— or —CO—, $R^{a10}$, $R^{a11}$ and $R^{a12}$ each independently represent a C1-C12 alkyl group or a C3-C12 alicyclic hydrocarbon group, and $R^{a10}$ and $R^{a11}$ can be bonded each other to form a C3-C20 ring together with the carbon atom to which $R^{a10}$ and $R^{a11}$ are bonded, and the C1-C12 alkyl group and the C3-C12 alicyclic hydrocarbon group can have one or more hydroxyl groups, and one or more —CH$_2$— in the C1-C12 alkyl group and the C3-C12 alicyclic hydrocarbon group can be replaced by —O— or —CO—.

Examples of the C1-C3 alkyl group which can have one or more hydroxyl groups include a methyl group, an ethyl group, a propyl group, a hydroxymethyl group and a 2-hydroxyethyl group.

In the formula (a1-3), $R^{a9}$ preferably represents a hydrogen atom. Examples of the alkyl group and the alicyclic hydrocarbon group for $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group. In the formula (a1-3), the ring formed by binding R$^{a10}$ and R$^{a11}$ each other includes preferably an aliphatic group, more preferably a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin (A) is obtained from the monomer represented by the formula (a1-3), the resin (A) has bulky structural units derived from the monomer. The photoresist composition which contains the resin (A) with such bulky structural unit can provide a photoresist composition with better DOF (forcus margin). Moreover, the resin (A) is obtained from the monomer represented by the formula (a1-3), the resin (A) has a rigid norbornene ring at its main chain so that the photoresist composition containing such resin can provide the photoresist composition higher dry-etching resistance.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin, considering that a photoresist composition with better DOF and higher dry-etching resistance is to be obtained.

Other examples of the compound having an acid-labile group include a monomer represented by the formula (a1-4):

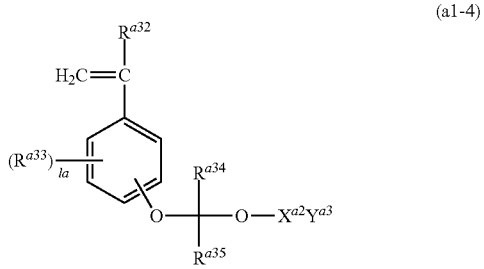

(a1-4)

wherein R$^{a32}$ represents a hydrogen atom, a halogen atom, a C1-C6 alkyl group or a C1-C6 halogenated alkyl group,
R$^{a33}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group,
la represents an integer of 0 to 4,
R$^{a34}$ and R$^{a35}$ each independently represent a hydrogen atom or a C1-C12 hydrocarbon group,
X$^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and
Y$^{a3}$ represents a C1-C12 aliphatic hydrocarbon group, a C3-C18 alicyclic hydrocarbon group or a C6-C18 aromatic hydrocarbon group, and the C1-C17 divalent saturated hydrocarbon group, the C1-C12 aliphatic hydrocarbon group, the C2-C18 alicyclic hydrocarbon group and the C6-C18 aromatic hydrocarbon group can have one or more substituents selected from the group consisting of a halogen atom, a hydroxyl group, a C1-C6 alkyl group, a C1-C6 alkoxy group, a C2-C4 acyl group and a C2-C4 acyloxy group.

The monomer represented by the formula (a1-4) has the acid-labile group (2) and carbon-carbon double bond.

Examples of the halogen atom include a fluorine atom, a chlorine atom, a bromine atom and an iodine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, a C3-C12 alicyclic hydrocarbon group such as a cyclohexyl group, an adamantyl group, a 2-alkyl-2-adamantyl group, a 1-(1-adamantyl)-1-alkyl group and an isobornyl group, an C6-C12 aromatic hydrocarbon group and a group formed by combining one or more above-mentioned groups. Among them, preferred are an isopropyl group, a butyl group, a sec-butyl group, a tert-butyl group, a pentyl group, a hexyl group, an octyl group, a 2-ethylhexyl group, a cyclohexyl group, an adamantyl group, a2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group.

Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

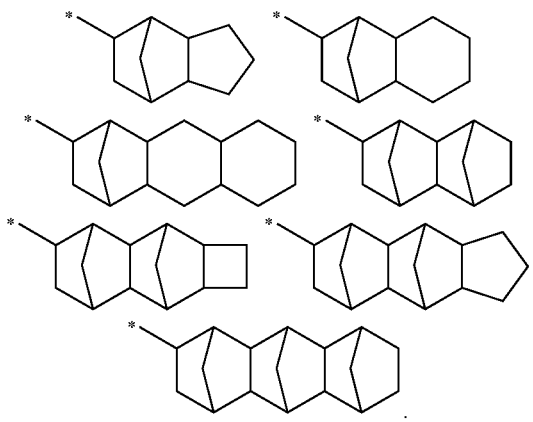

Examples of the C6-C18 aromatic hydrocarbon group include a phenyl group, a naphthyl group, an anthryl group, a p-methylphenyl group, a p-tert-butylphenyl group and a p-adamantylphenyl group.

$R^{a32}$ and $R^{a33}$ each represents preferably C1-C4 alkyl group, more preferably a methyl or ethyl group, and still more preferably a methyl group.

$R^{a33}$ preferably represents a methoxy or ethoxy group, and more preferably a methoxy group.

$R^{a34}$ and $R^{a35}$ each represents preferably isopropyl group, n-butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(1-adamantyl)-1-alkyl group and an isobornyl group.

Preferred substituents of $X^{a2}$ and $Y^{a3}$ are a hydroxyl group.

Examples of the monomer represented by the formula (a1-4) include the followings.

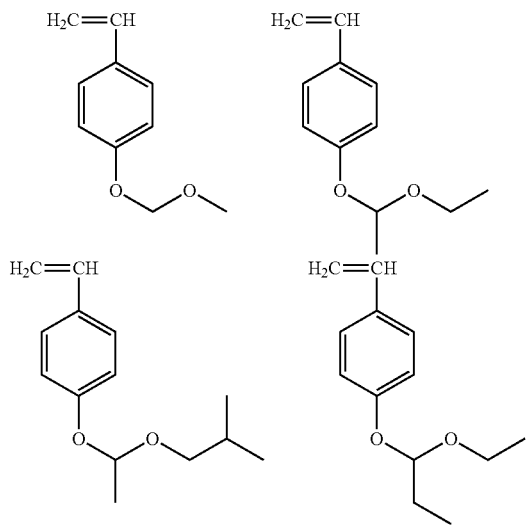

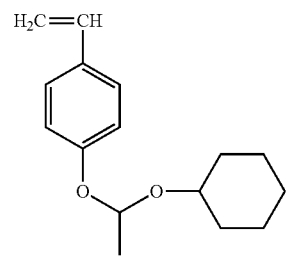

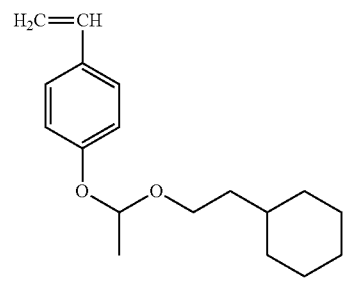

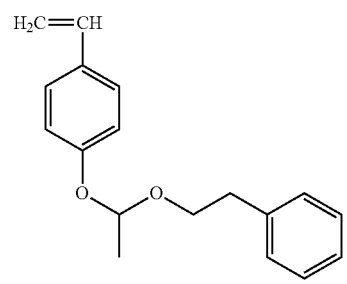

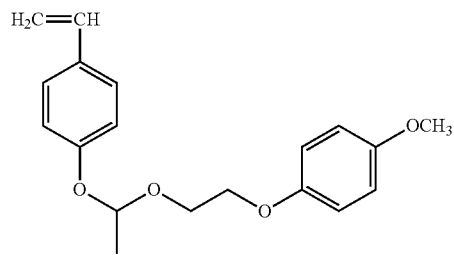

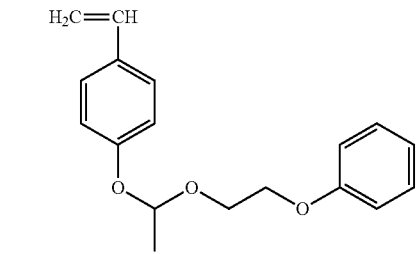

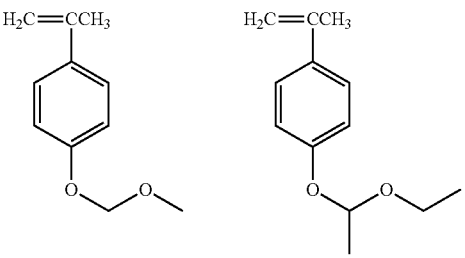

-continued
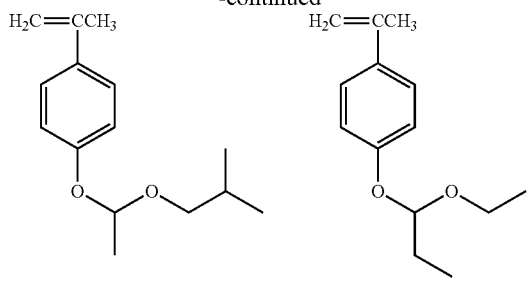
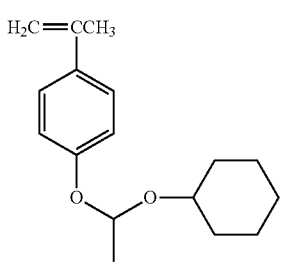
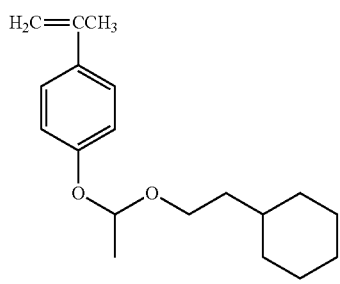
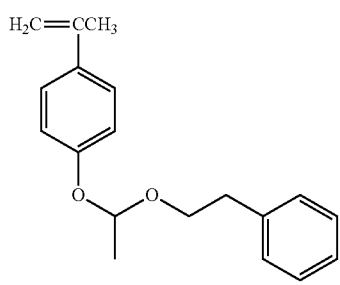
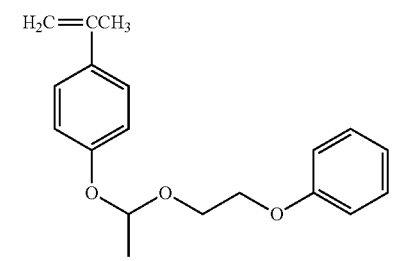
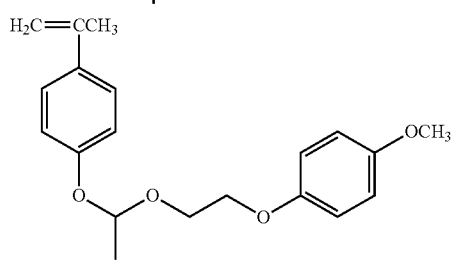
-continued
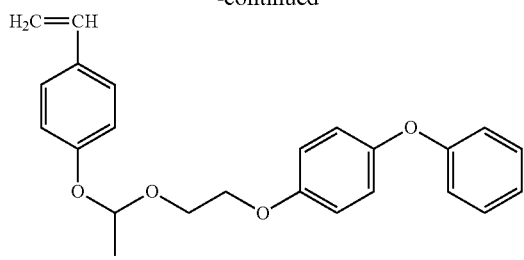
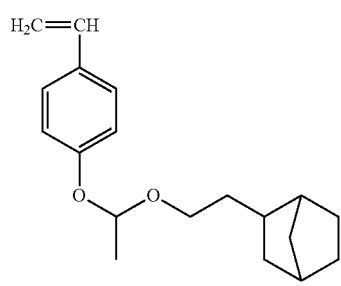
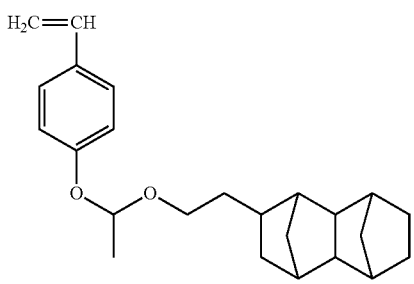
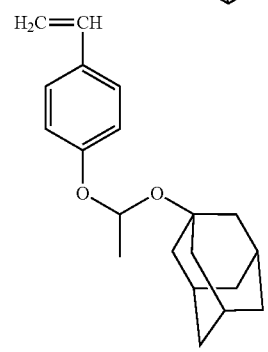
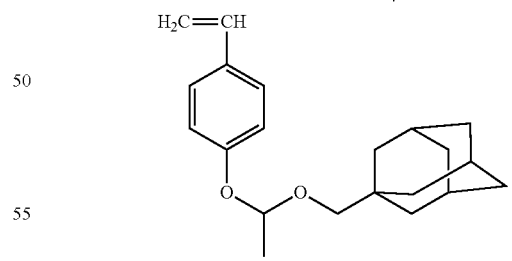
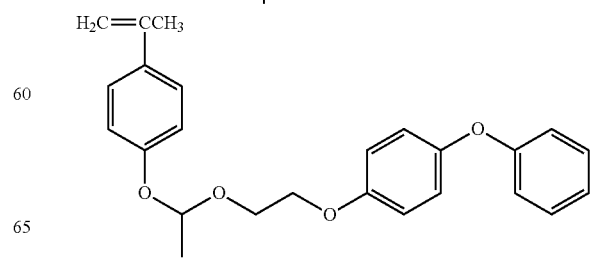

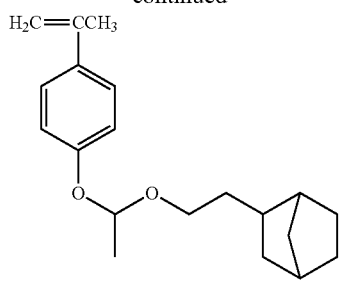
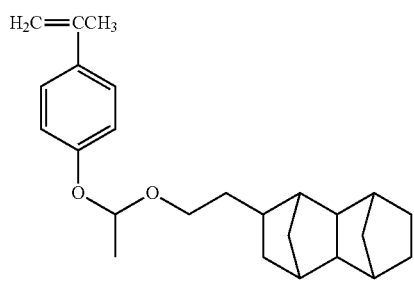
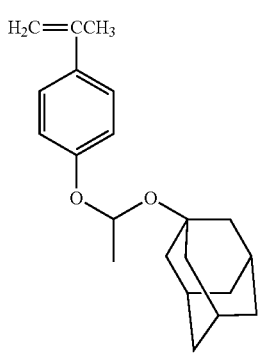
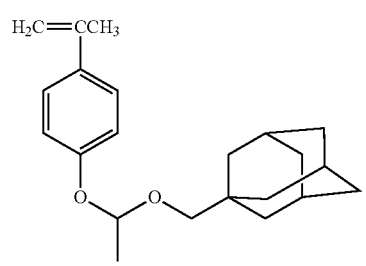
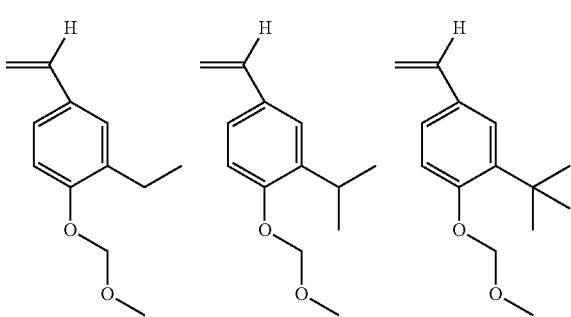
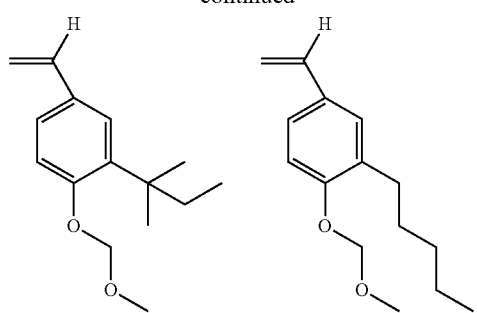
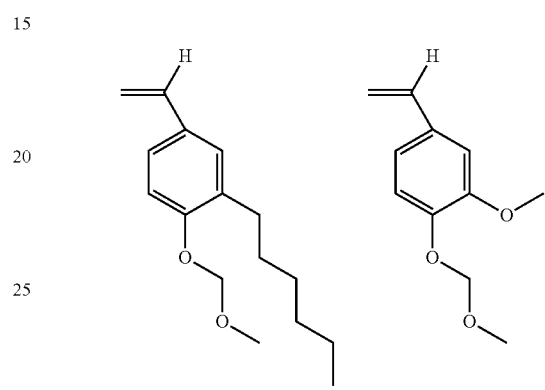
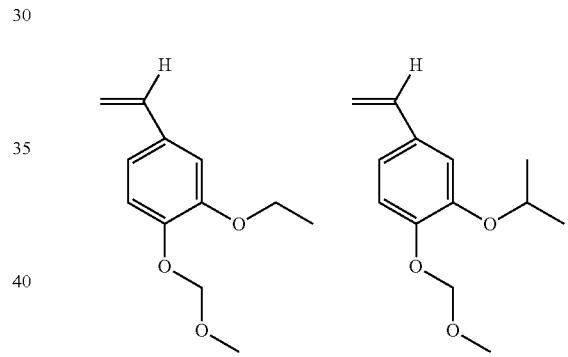
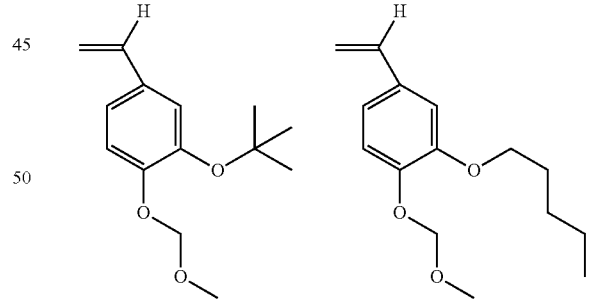
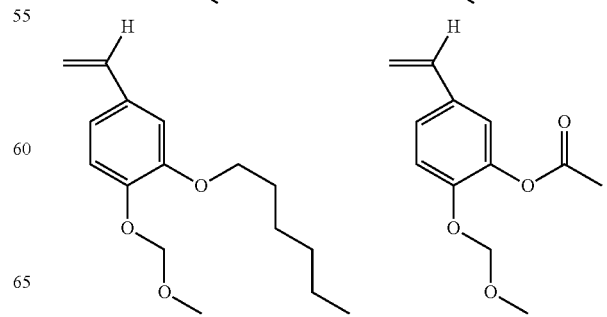

-continued
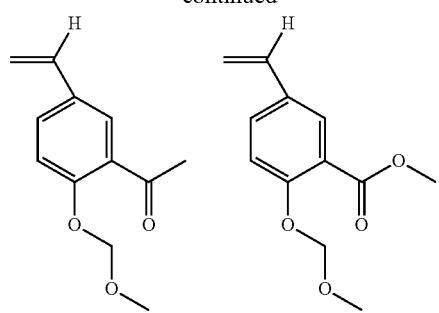
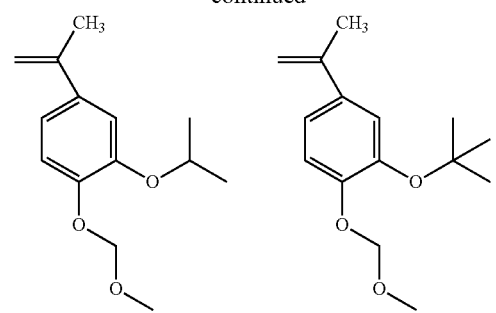
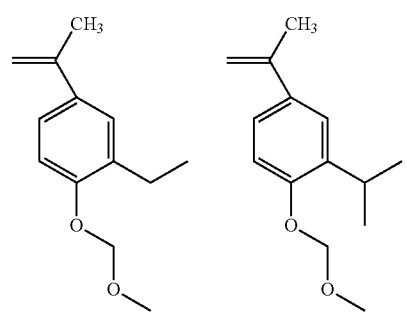
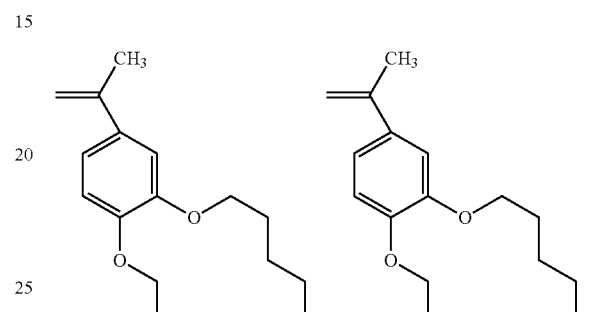
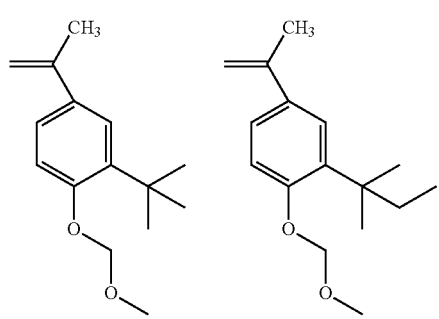 [SMILES: C=C(c1ccc(OCOC)c(C(C)(C)C)c1)C(F)(F)F ; C=C(c1ccc(OCOC)c(C(C)(C)CC)c1)C(F)(F)F]
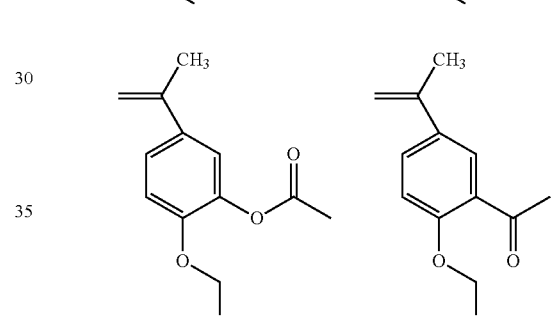
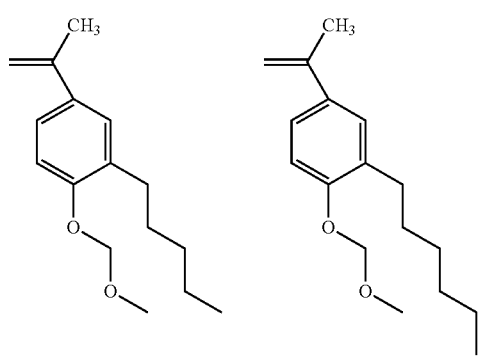
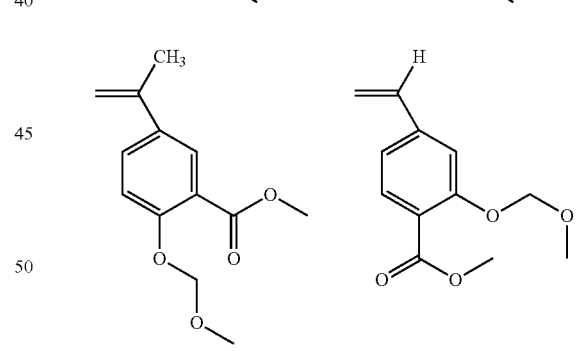
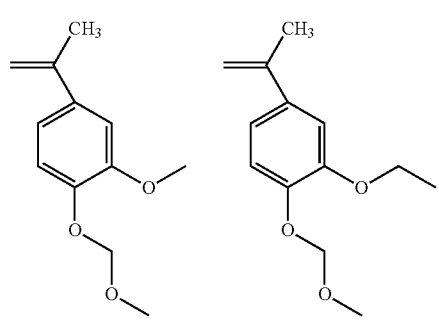
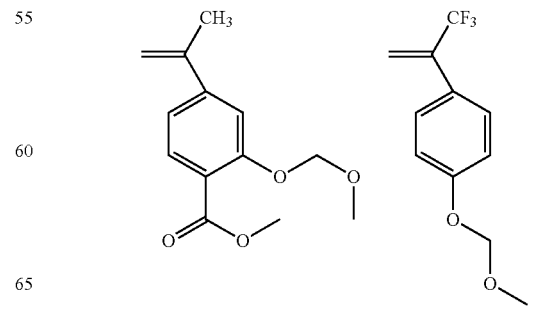

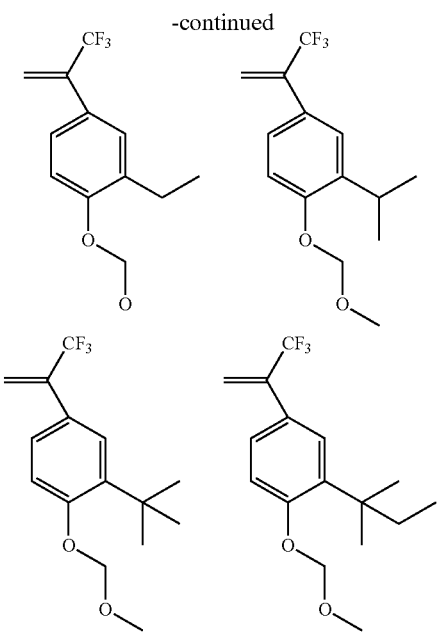

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

Furthermore, another monomer having an acid-liable group (1) and carbon-carbon double bond can be used for the present invention. Examples of such monomer include those represented by the formulae:

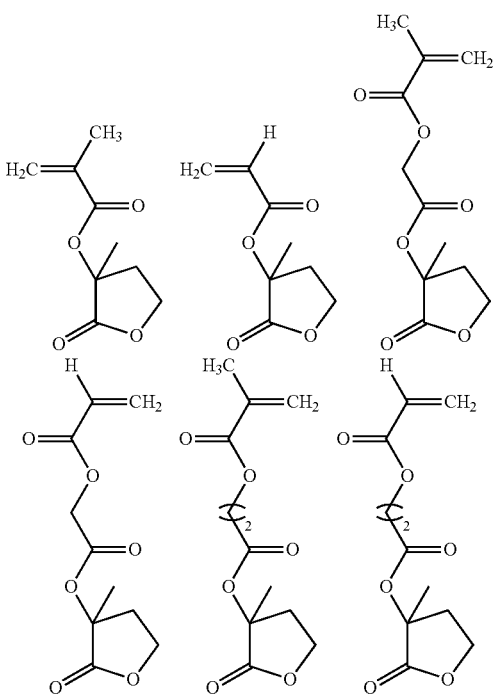

When the resin (A) contains the structural unit derived form such monomers, the content of the structural unit derived from the monomers is usually 10 to 95% by mole and preferably 15 to 90% by mole and more preferably 20 to 85% by mole based on total molar of all the structural units of the resin.

The resin (A) can have two or more kinds of structural units derived from the monomers having an acid-labile group.

The resin (A) preferably contains the structural unit derived from the monomer having an acid-labile group and a structural unit derived from the monomer having no acid-labile group. The resin which contains only the structural units derived from the monomer having no acid-labile group can be used for an additive of the photoresist composition of the present invention.

When the resin contains the structural unit derived from the monomer having an acid-labile group and the structural unit derived from the monomer having no acid-labile group, the content of the structural unit derived from the monomer having an acid-labile group is preferably 10 to 80% by mole and more preferably 20 to 60% by mole based on total molar of all the structural units of the resin and the content of the structural unit derived from the monomer having no acid-labile group is usually 90 to 20% by mole and preferably 80 to 40% by mole based on total molar of all the structural units of the resin.

The content of the structural unit derived from a monomer having an adamantyl group, especially the monomer represented by the formula (a1-1) is preferably 15% by mole or more from the viewpoint of dry-etching resistance of the photoresist composition.

The monomer having no acid-labile group preferably contains one or more hydroxyl groups or one or more lactone ring. When the resin contains the structural unit derived from the monomer having no acid-labile group and having one or more hydroxyl groups or one or more lactone ring, a photoresist composition with excellent adhesiveness of resist to a substrate can be obtained, which the composition can provide a photoresist composition with good DOF.

When the resin (A) is obtained from the monomer having an acid-liable monomer and the monomer having no acid-labile group, two or more of the monomers having no acid-labile group can be used depending on the sources of the exposure for producing a photoresist composition.

When the photoresist composition is to be exposed to KrF excimer laser (wavelength: 248 nm) lithography system, or a high energy laser such as electron beam and extreme ultraviolet, the resin containing the structural unit derived from the monomer having no acid-liable group but phenolic-hydroxy group, e.g., hydroxystylene, can be used as the resin (A) of the photoresist composition. When the photoresist composition is to be exposed to ArF excimer laser (wavelength: 193 nm), the resin containing the structural unit derived from the monomer represented by the formula (a2-1) is preferable.

Examples of the monomer having no acid-labile group and having one or more hydroxyl groups include a monomer represented by the formula (a2-0):

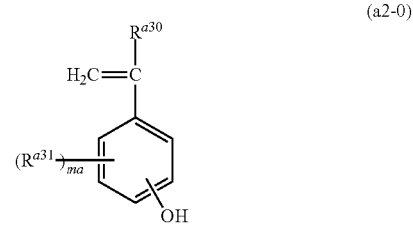

(a2-0)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group.

In the formula (a2-0), ma is preferably 0, 1 or 2, and is more preferably 0 or 1, and especially preferably 0.

The resin containing the structural unit derived from the monomer represented by the formula (a2-0) can be produced, for example, by conducting radical polymerization of a (meth)acarylate monomer and acetoxystylene and optionally other polymerizable monomers, followed by conducting deacetylation of the obtained polymer with an acid or base. In the process, acetoxystylene is a monomer obtained by protecting a hydroxyl group of the monomer represented by the formula (a2-0) with a protecting group such as an acetyl group, and other monomers in which a hydroxyl group of the formula (a2-0) has been protected with a suitable protecting group can be used for the above-mentioned process instead of acetoxystylene.

Examples of the monomer represented by the formula (a2-0) include JP-A-2010-204634, preferably the compounds represented by the formula (a2-0-1) or the formula (a2-0-1). The compounds in which a phenolic-hydroxyl group of the formulae (a2-0-1) and (a2-0-1) has been protected with a suitable protecting group can be used for the production of the resin (A).

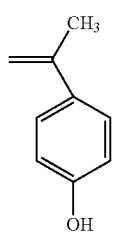

(a2-0-1)

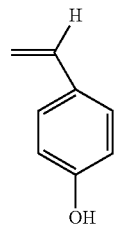

(a2-0-2)

When the resin contains the structural unit derived from the monomer represented by the formula (a2-0), the content of the structural unit derived from the monomer represented by the formula (a2-0) is usually 5 to 95% by mole and preferably 10 to 80% by mole and more preferably 15 to 80% by mole based on total molar of all the structural units of the resin.

Examples of the monomer having no acid-labile group and having one or more hydroxyl groups include a monomer represented by the formula (a2-1):

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O—in which * represents a binding position to —CO—, and f2 represents an integer of 1 to 4, and is more preferably *—O—, and of is preferably 0, 1, 2 or 3 and is more preferably 0 or 1.

Examples of the monomer represented by the formula (a2-1) include JP-A-2010-204646, preferably the compounds represented by the formula (a2-1-1), the formula (a2-1-2), the formula (a2-1-3), the formula (a2-1-4), the formula (a2-1-5) or the formula (a2-1-6), more preferably the compounds represented by the formula (a2-1-1), the formula (a2-1-2), the formula (a2-1-3) or the formula (a2-1-4), and still more preferably the compounds represented by the formula (a2-1-1) or the formula (a2-1-3).

(a2-1-1)
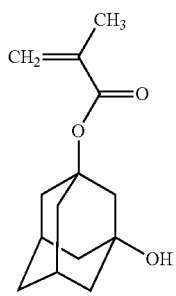

(a2-1-2)
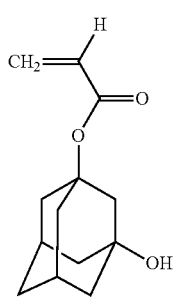

(a2-1-3)
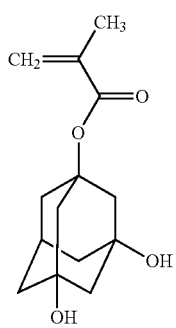

(a2-1-4)
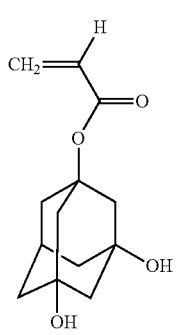

(a2-1-5)
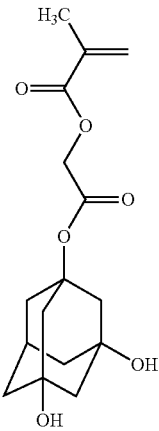

(a2-1-6)
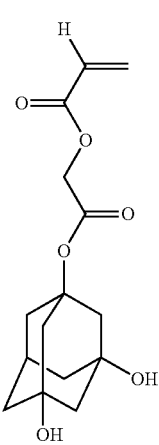

When the resin contains the structural unit derived from the monomer represented by the formula (a2-1), the content of the structural unit derived from the monomer represented by the formula (a2-1) is preferably 3 to 45% by mole, more preferably 5 to 40% by mole, still more preferably 5 to 35% by mole, and in particular preferably 5 to 20% by mole, based on total molar of all the structural units of the resin.

Examples of the lactone ring of the monomer having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formula (a3-1):

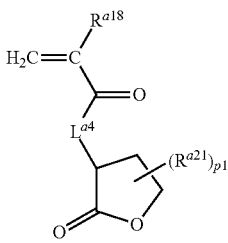
(a3-1)

wherein $L^{a4}$ represents *—O— or *—O— $(CH_2)_{k3}$—CO—O— in which * represents a binding position to —CO— and k3 represents an integer of 1 to 7, $R^{a18}$ represents a hydrogen atom or a methyl group, $R^{a21}$ represents independently in each occurrence a C1-C4 aliphatic hydrocarbon group, and p1 represents an integer of 0 to 5.

It is preferred that $L^{a4}$ represents *—O— or *—O—$(CH_2)_{d1}$—CO—O— in which * represents a binding position to —CO— and d1 represents an integer of 1 to 4, and it is more preferred that $L^{a4}$ is *—O—. $R^{a18}$ and $R^{a21}$ each is preferably a methyl group. It is preferred that p1 is an integer of 0 to 2, and it is more preferred that p1 is 0 or 1.

Examples of the monomer represented by the formula (a3-1) include a monomer mentioned in JP2010-A-204646, preferably the compounds represented by the formula (a3-1-1), the formula (a3-1-2), the formula (a3-1-3) and the formula (a3-1-4), more preferably the compounds represented by the formula (a3-1-1) and the formula (a3-1-2), and still more preferably the compounds represented by the formula (a3-1-1).

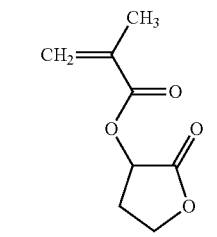
(a3-1-1)

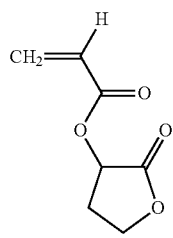
(a3-1-2)

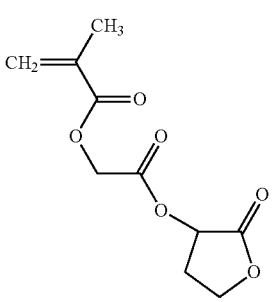
(a3-1-3)

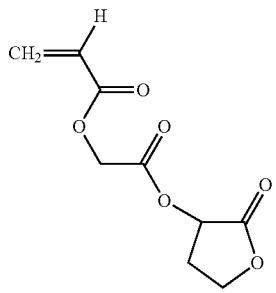
(a3-1-4)

When the resin contains the structural unit derived from the monomer having no acid-labile group and having a lactone ring, the content thereof is preferably 5 to 70% by mole, more preferably 10 to 65% by mole, and still more preferably 10 to 60% by mole, based on total molar of all the structural units of the resin.

Examples of the other monomer having no acid-labile group include the monomers represented by the formulae (a-4-1), (a-4-2) and (a-4-3):

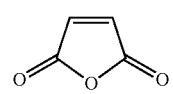
(a4-1)

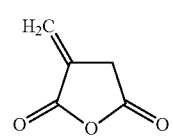
(a4-2)

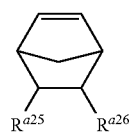
(a4-3)

wherein $R^{a25}$ and $R^{a26}$ each independently represents a hydrogen atom, a C1-C3 alkyl group which can have one or more hydroxyl groups, a cyano group, a carboxyl group or a —$COOR^{a27}$ group in which $R^{a27}$ represents a C1-C18 alkyl group, a C3-C18 alicyclic hydrocarbon group, or group consisting of a C1-C18 alkyl group and a C3-C18 alicyclic hydrocarbon group, and one or more —$CH_2$— in the C1-C18 alkyl group and the C3-C18 alicyclic hydrocarbon group can be replaced by —O— or —CO—, with the proviso that the carbon atom bonded to —O— of —COO— of $R^{a27}$ is not a tertiary carbon atom, or $R^{a25}$ and $R^{a26}$ are bonded together to form a carboxylic anhydride residue represented by —C(=O)—O—C(=O)—.

The C1-C18 alkyl group represented by $R^{a27}$ preferably a C1-C8 alkyl group and is more preferably a C1-C6 alkyl group. The C3-C18 alicyclic hydrocarbon group represented by $R^{a27}$ is preferably a C4-C18 alicyclic hydrocarbon group, and is more preferably C4-C12 alicyclic hydrocarbon group.

Examples of the monomer represented by the formula (a-4-3) include 2-norbornene, 2-hydroxy-5-norbornene, 5-norbornene-2-carboxylic acid, methyl 5-norbornene-2-carboxylate, 2-hydroxy-1-ethyl 5-norbornene-2-carboxylate, 5-norbornene-2-methanol and 5-norbornene-2,3-dicarboxylic anhydride.

When the resin contains a structural unit derived from a monomer represented by the formula (a-4-1), (a-4-2) or (a-4-3), the content thereof is preferably 2 to 40% by mole and more preferably 3 to 30% by mole and still more preferably 5 to 20% by mole based on total molar of all the structural units of the resin.
Examples of the other monomer having no acid-labile group include the fluorine-containing monomers represented by the following formulae.
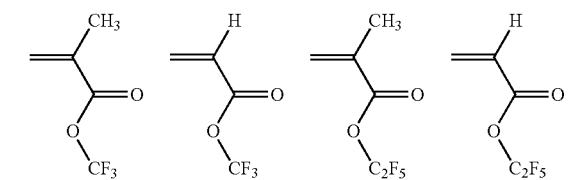
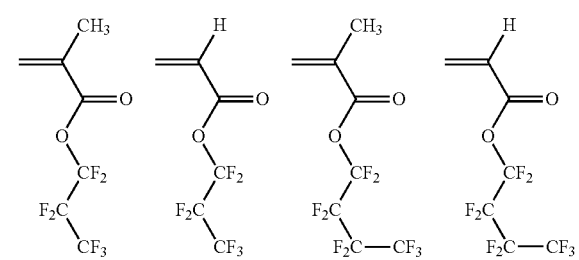
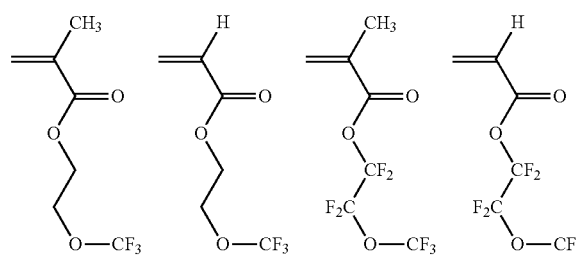
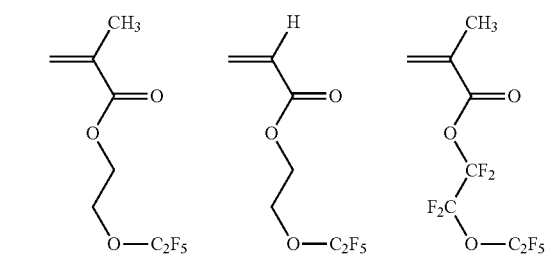
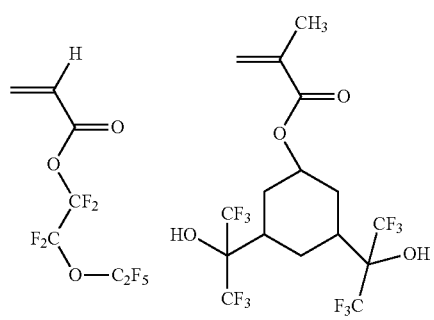
-continued
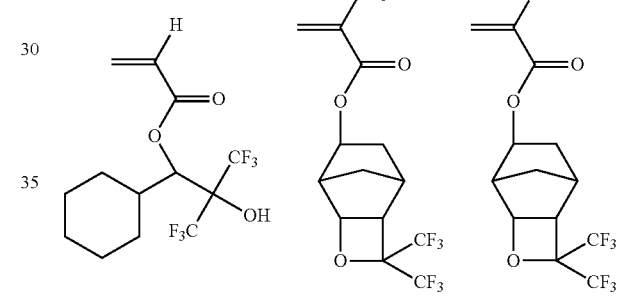
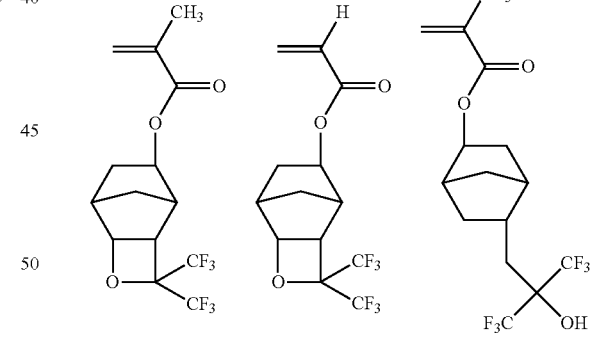
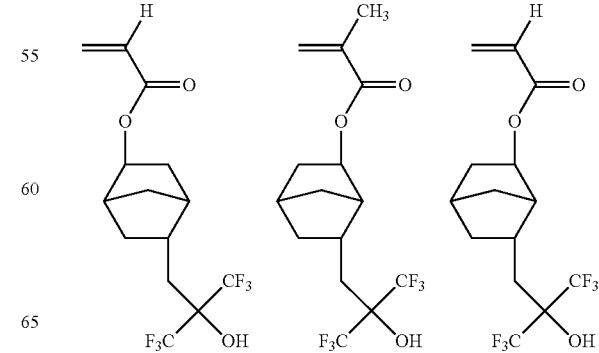

-continued

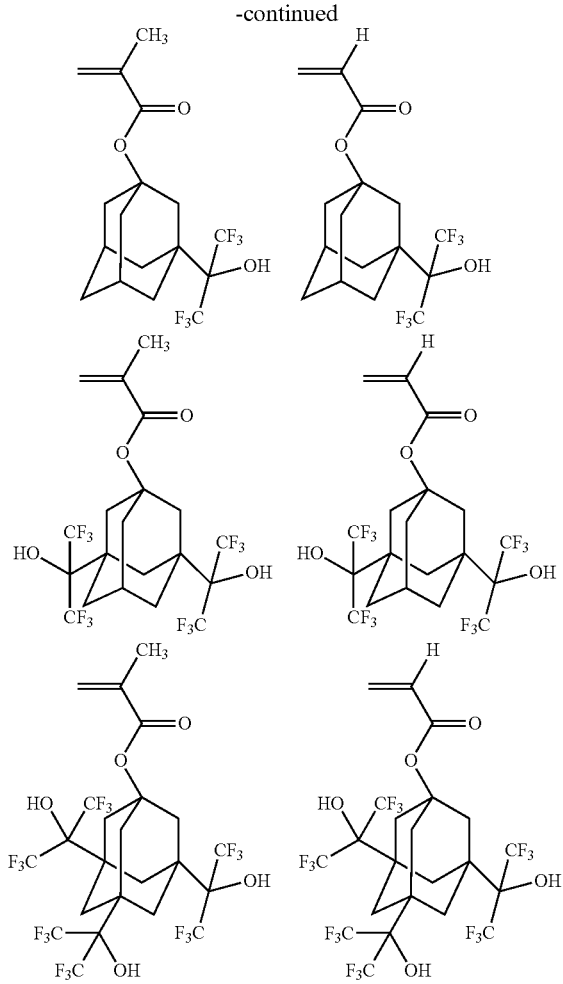

Among them, preferred are
5-(3,3,3-trifluoro-2-hydroxy-2-(trifluoromethyl)propyl)bicyclo[2.2.1]hept-2-yl (meth)acrylate,
6-(3,3,3-trifluoro-2-hydroxy-2-(trifluoromethyl)propyl)bicyclo[2.2.1]hept-2-yl (meth)acrylate, and
4,4-bis(trifluoromethyl)-3-oxatricyclo[4.2.1.0$^{2,5}$]nonyl (meth)acrylate.

When the resin contains a structural unit derived from the above-mentioned fluorine-containing monomer, the content thereof is preferably 1 to 20% by mole, more preferably 2 to 15% by mole and still more preferably 3 to 10% by mole, based on total molar of all the structural units of the resin.

The resin (A) is preferably a copolymer obtained by polymerizing a monomer having an acid-labile group, and as necessary a monomer represented by the formula (a2), the formula (a3) or the formula (a3) in an amount such that each structural unit of these monomers amounts to the suitable content relative to the total structural units, by a known polymerization process (e.g., radical polymerization).

Weight average molecular weight of the resin (A) is preferably 2500 or more, and more preferably 3000 or more. The upper limit of the weight average molecular weight is preferably 50000, and more preferably 30000. Herein, the weight average molecular weight is determined by gel permeation chromatography analysis, which is calculated based on the standard polystyrene. Specific condition of the analysis is described in the examples of the present invention.

Preferable resin is a resin containing the structural units derived from the monomer having an acid-labile group and the structural units derived from the monomer having no acid-labile group, and more preferable resin is a resin containing the structural units derived from the monomer having an acid-labile group and the structural units derived from the monomer having one or more hydroxyl groups and/or the monomer having a lactone ring.

The resin (A) is preferably a copolymer obtained by polymerizing a monomer having an acid-labile group, a monomer represented by the formula (a2) and/or a monomer represented by the formula (a3). As the copolymer, a monomer having an acid-labile group is preferably those represented by the formula (a1-1) and the formula (a1-2), and more preferably those represented by the formula (a1-1),
a monomer represented by the formula (a2) is preferably those represented by the formula (a2-1), and monomer represented by the formula (a3) is preferably those represented by the formula (a3-1).

The resin (A) is preferably a copolymer obtained by polymerizing a monomer having an acid-labile group, a monomer represented by the formula (a2) and/or a monomer represented by the formula (a3).

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound and an ammonium salt.

The amine compound includes an aliphatic amine or an aromatic amine. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine.

Examples thereof include preferably an aromatic amine represented by the formula (C2), and more preferably aniline represented by the formula (c2-1):

(C2)

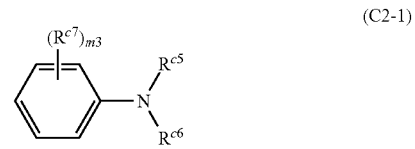

(C2-1)

wherein Ar$^{c1}$ represents an aromatic hydrocarbon group, and R$^{c5}$ and R$^{c6}$ independently represent a hydrogen atom, an alkyl group, an alicyclic hydrocarbon group or an aromatic hydrocarbon group, and R$^{c7}$ is independently in each occurrence an alkyl group, an alkoxy group, an alicyclic hydrocarbon group, an aromatic hydrocarbon group or a nitro group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

In the formulae (C2) and (C2-1), the alkyl group preferably has 1 to 6 carbon atoms. The alkoxy group preferably has 1 to 6 carbon atoms. The alicyclic hydrocarbon group preferably has 5 to 10 carbon atoms, and is more preferably C5-C10 cycloalkyl group. The aromatic hydrocarbon group preferably has 6 to 10 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

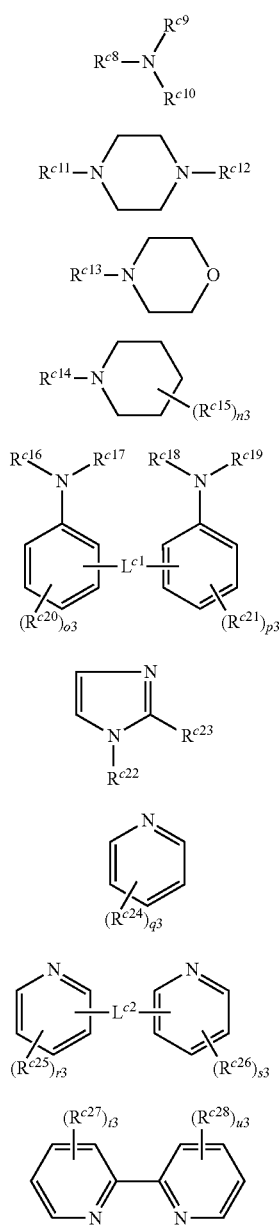

wherein $R^{c8}$, $R^{c20}$, $R^{c21}$, and $R^{c23}$ to $R^{c28}$ independently represent an alkyl group, an alkoxy group, an alicyclic hydrocarbon group, an aromatic hydrocarbon group or a nitro group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$ to $R^{c14}$, $R^{c16}$ to $R^{c19}$, and $R^{c22}$ independently represents a hydrogen atom, an alkyl group, an alicyclic hydrocarbon group or an aromatic hydrocarbon group, and the alkyl group, the alicyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an alkyl group (preferably C1-C6 alkyl group), an alicyclic hydrocarbon group (preferably C3-C6 alkyl group) or an alkanoyl group (preferably C2-C6 alkanoyl group), $L^{c1}$ and $L^{c2}$ independently represents an alkanediyl group, —CO—, —C(=NH)—, —C(=NR$^{c3}$)—, —S—, —S—S— or a combination thereof and $R^{c3}$ represents a C1-C4 alkyl group, O3, p3, q3, r3, s3, t3 and u3 each independently represents an integer of 0 to 3 and n3 represents an integer of 0 to 8.

In the formulae (c3) to (C11), the alkyl group has preferably 1 to 6 carbon atoms, and the alicyclic hydrocarbon group has preferably 3 to 6 carbon atoms, and the alkanoyl group has preferably 2 to 6 carbon atoms. The alkanediyl group is preferably C1-C6 alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the ammonium hydroxide include tetramethylammonium hydroxide, tetrapropylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide, tetra-n-butylammoniumsalicylate and (2-hydroxyethyl)trimethylammonium hydroxide (so-called "choline").

The basic compound is preferably diisopropylaniline, tetrabutylammoniumhydroxideandtetra-n-butylammoniumsalicylate, and 2,6-diisopropylaniline, tetrabutylammonium hydroxide and tetra-n-butylammoniumsalicylate.

When the photoresist compositions contain the basic compound, the content thereof is usually 0.01 to 1% by weight based on sum of solid component. The content of the basic compound is preferably smaller than total content of SALT (I) and the acid generator other than SALT (I). In this specification, "solid component" means components other than solvent in the photoresist composition.

The photoresist compositions of the present invention preferably contain one or more solvents. The solvent can be selected depending on the SALT (I), the resin (A), the acid generator and their amounts as well as the process for producing photoresist compositions, considering application of the photoresist composition on the substrate.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the present invention can contain, if necessary, a small amount of various additives known in the art, such as a sensitizer, a dissolution inhibitor, other polymers, a surfactant, a stabilizer and a dye.

The photoresist composition of the present invention can be produced by mixing the SALT (I) and the resin (A) usually in the above-mentioned solvent. The acid generators, the basic compound and/or additives are mixed therein, as necessary. Preferably the basic compound is mixed therein. Mixing order of the components is not limited to a specific order. The temperature at mixing the components is usually from 10° C. to 40° C., which can be suitably selected depending on the SALT (I) to be used, or the solubility of the SALT (I) in the solvent. The mixing time is usually from 0.5 to 24 hours, which can be suitably selected depending on the mixing temperature. Means for mixing the components is not limited to a specific one, which includes stirring.

Each amount of the components in the photoresist composition of the present invention can be adjusted by selecting the amount of the components to be used for preparing the photoresist composition.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention. The photoresist composition which contains the solvent in such amount can easily provide a layer of the composition with thickness from 30 to 300 nm around.

The amount of the resin (A) is preferably 80% by weight or more, and 99% by weight or less based on total amount of the solid in the photoresist composition of the present invention. Herein, the "solid" refers to the total amount of the components other than the solvent.

The amount of the SALT (I) is preferably 1 part by weight or more and more preferably 3 parts by weight or more per 100 parts of the resin (A). The upper limit of the amount is preferably 30 parts by weight and more preferably 25 parts by weight per 100 parts of the resin (A).

The amount of the basic compound, if used, is preferably from 0.01 to 1% by weight based on the total amount of the solid in the photoresist composition. The amount of the basic compound is less than the total amount of the SALT (I) and the resin (A).

The amount of the additives, if used, can be adjusted to a suitable amount depending on the kind of the additives.

After mixing each component in a suitable amount, the obtained mixture is preferably filtrated through a filter with pore diameter from 0.01 to 0.2 μm.

The photoresist pattern of the present invention can be produced by the following steps (1) to (5):

(1) a step of applying the photoresist composition of the present invention on a substrate,
(2) a step of forming a resist film by conducting drying,
(3) a step of exposing the resist film to radiation,
(4) a step of baking the exposed resist film, and
(5) a step of developing the baked resist film.

In the step (1), the applying of the photoresist composition on a substrate is usually conducted using a conventional apparatus for application of fine-processed resist materials such as spin coater.

By the step, the coat consisting of the photoresist composition is formed on the substrate. The thickness of the coat can be adjusted by controlling the condition of the apparatus for application. The condition of the application for obtaining the coat with a desired thickness can be selected by conducting a suitable preliminary experiment. The substrate can be selected from various one for fine-processing. Examples of the substrate include a silicon wafer or a quartz wafer on which a sensor, a circuit, a transistor or the like is formed. The substrate may be cleaned or coated with an antireflection coat. The antireflection coat can be formed by commercially available compositions for the antireflection coat.

In the step (2), the solvent is removed from the coat, i.e., the photoresist composition having been coated in the substrate by drying it. Drying the coat is conducted, for example by evaporating the solvent from the coat using a heating apparatus such as hot plate, by reducing the pressure using a decompression apparatus, or by combining these meanings. The condition of drying the coat can be selected depending on the solvent of the photoresist composition.

The heating temperature is preferably 50 to 200° C. In case of reducing the pressure, the inner pressure is preferably at 1 to $1.0*10^5$ Pa.

The step (3) comprises exposing the resist film to radiation, preferably using an exposure apparatus.

The exposure is usually conducted through a mask having a pattern corresponding to the desired photoresist composition, i.e., photomask.

Examples of the exposure source, include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser). The exposure apparatus from which electron ray or extreme ultraviolet (EUV) radiates may be used for the step. Herein, exposure to any of the above-mentioned exposure sources is collectively referred to as "exposing to radiation".

Exposure of the resist film to radiation through the mask makes exposed parts and non-exposed parts in the resist film. In the exposed parts, an acid is formed from the SALT (I) and an acid generator by exposure energy, and then the acid causes deprotection reaction of an acid-liable group in the resin (A) to form a hydrophilic group, resulting that the resin of the film becomes soluble in an alkali solution. In the non-exposed parts, the resin of the film remains insoluble or hardly soluble in an alkali solution because of not receiving exposure energy. The exposed parts and the non-exposed parts are much different in the solubility in an alkali solution.

The step (4) comprises baking the exposed resist film, that is post-exposure bake. Baking is preferably conducted using a heating apparatus as mentioned above. The temperature of baking of the exposed resist film is usually 50 to 200° C., and preferably 70 to 150° C. The baking step can drives the deprotection reaction as mentioned above.

The step (5) comprises developing the baked resist film, preferably using a development apparatus. In this step, various alkaline aqueous solutions known in the art may be used for the developing. By contacting the baked resist film to an alkaline aqueous solution, the film of the exposed parts is removed from the substrate while the film of the non-exposed parts is not, resulting that the photoresist pattern is formed in the substrate. Generally, an aqueous solution of tetramethylammonium hydroxide or (2-hydroxyethyl) trimethylammonium hydroxide (commonly known as "choline") is often used.

After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, EUV (extreme ultraviolet) lithography, and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The content of any component of the resin (A), i.e., the ratio of the structural units derived from the monomers used for producing the resin, was determined from the amounts of the used monomers which amounts were calculated from the amounts of not-reacted monomers determined by liquid chromatography of the mixture after polymerization.

The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 μL] using standard polystyrene as a standard reference material.

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). In the following examples, the peaks of the mass Spectrometry are shown as "MASS" values.

Example 1

Synthesis of the Salt Represented by Formula (I1)

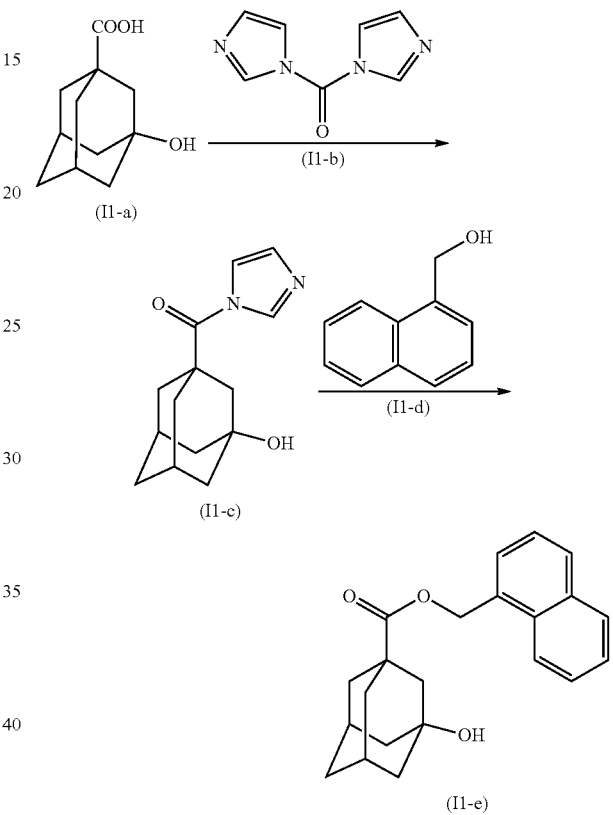

A mixture of 13.65 parts of the compound represented by the formula (I1-a) and 81.87 parts of chloroform was stirred at 23° C. for 30 minutes. To the mixture, 12.4 parts of the compound represented by the formula (I1-b) were added and then stirred at 60° C. for 1 hour to obtain a solution containing the compound represented by the formula (I1-c). To the solution, 10 parts of the compound represented by the formula (I1-d) was fed and then stirred at 23° C. for 17 hours. To the obtained reactant, 40.94 parts of deionized water was poured and then stirred at 23° C. for 30 minutes. Then an organic layer was separated after setting the resulting mixture still. Then, the organic layer was washed with water in the same manner as above 8 times in total. The resulting organic layer was concentrated. By separated from the obtained concentrate with a column (Column: MERCK Silica gel 60-200 mesh, solvent: mixture of n-heptan/ethyl acetate (=1/1)), 20.49 parts of the compound represented by the formula (I1-e) were obtained.

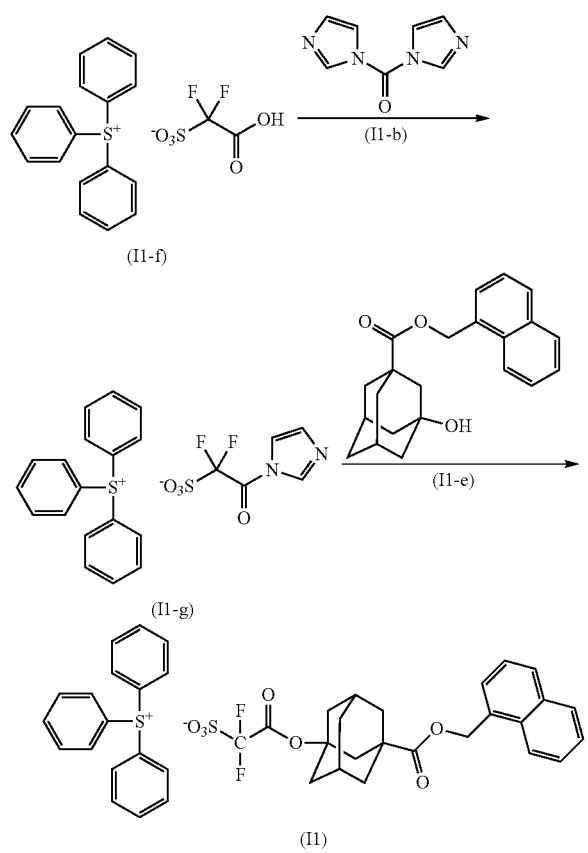

4.98 parts of the compound represented by the formula (I1-f) and 30 parts of acetonitrile were mixed and stirred at 23° C. for 30 minutes. Then 2.66 parts of the compound represented by the formula (I1-b) were added thereto and stirred at 82° C. for 1 hour to obtain a solution containing a compound represented by the formula (I1-g).

Into the solution, 3.44 parts of the compound represented by the formula (I1-e) and 3.44 parts of acetonitrile were fed and stirred at 82° C. for 16 hours. The resultant mixture was concentrated. To the obtained concentrate, 30 parts of chloroform and 15 parts of deionized water were added thereto, followed by stirring at 23° C. for 30 minutes.

Then an organic layer was separated after setting the resulting mixture still. Into the organic layer, 15 parts of deionized water was poured and stirred at 23° C. for 30 minutes to wash the layer. Such washing was conducted further 5 times.

The resulting organic layer was concentrated. To the organic layer, 8.84 parts of active carbon was added and stirred at 23° C. for 30 minutes followed by filtration. The filtrate obtained was concentrated. To the residue obtained, 700.35 parts of tert-buthylmethylether was added and then stirred. After removing supernatant theirfrom, the residue was concentrated. The resultant concentrate was dissolved in chloroform and concentrated. By separated from the obtained concentrate with a column (Column: MERCK Silica gel 60-200 mesh, solvent:mixture of chloroform/methanol (=5/1)), 5.24 parts of the salt represented by the formula (I1) were obtained.

MS (ESI (+) Spectrum): M$^+$ 263.1

MS (ESI (−) Spectrum): M$^-$ 493.1

Example 2

Synthesis of the Salt Represented by Formula (I12)

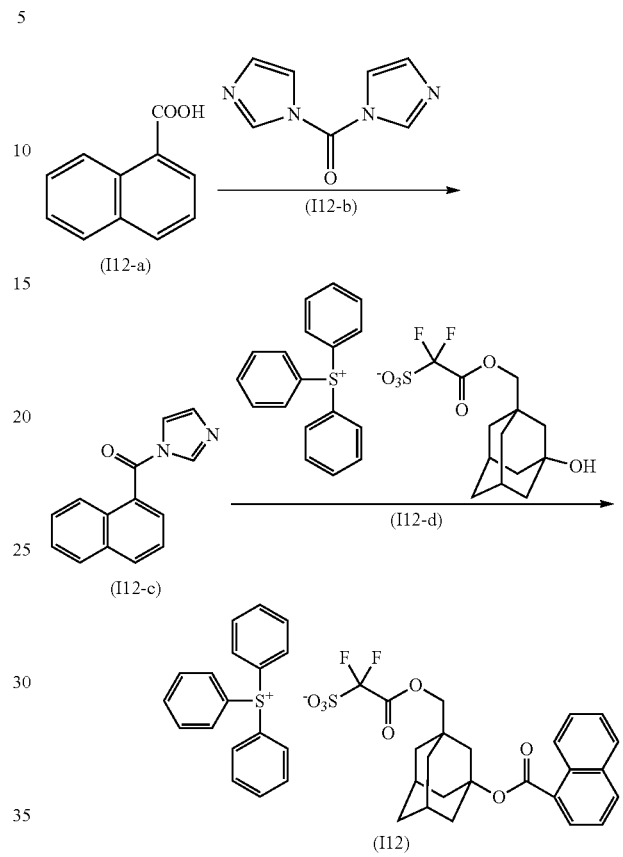

A mixture of 5 parts of the compound represented by the formula (I12-a) and 30 parts of acetonitrile was stirred at 23° C. for 30 minutes. To the mixture, 5.63 parts of the compound represented by the formula (I12-b) were added and then stirred at 82° C. for 1 hour to obtain a solution containing the compound represented by the formula (I12-c). To the solution, 10 parts of the compound represented by the formula (I12-d) was fed and then stirred at 82° C. for 44 hours. Cooling the obtained reactant, 133.86 parts of chloroform and 44.62 parts of deionized water were added thereto and stirred at 23° C. for 30 minutes. Then an organic layer was separated after setting the resulting mixture still. Then, the organic layer was washed with deionized water in the same manner as above 8 times in total. To the organic layer, 1.24 parts of active carbon was added and stirred at 23° C. for 30 minutes followed by filtration. The filtrate obtained was concentrated. To the residue obtained, 61.4 parts of tert-buthylmethylether was added and then stirred. After removing supernatant theirfrom, 5 parts of acetonitrile was added to the residue, dissolving it in the acetonitrile, followed by concentration.

Further, 17.2 parts of ethyl acetate was added to the obtained concentrates, followed by concentration to obtain 1.6 parts of the compound represented by the formula (I12).

MS (ESI(+) Spectrum): M$^+$263.1

MS (ESI(−) Spectrum): M$^-$ 493.1

Example 3

Synthesis of the Salt Represented by Formula (I129)

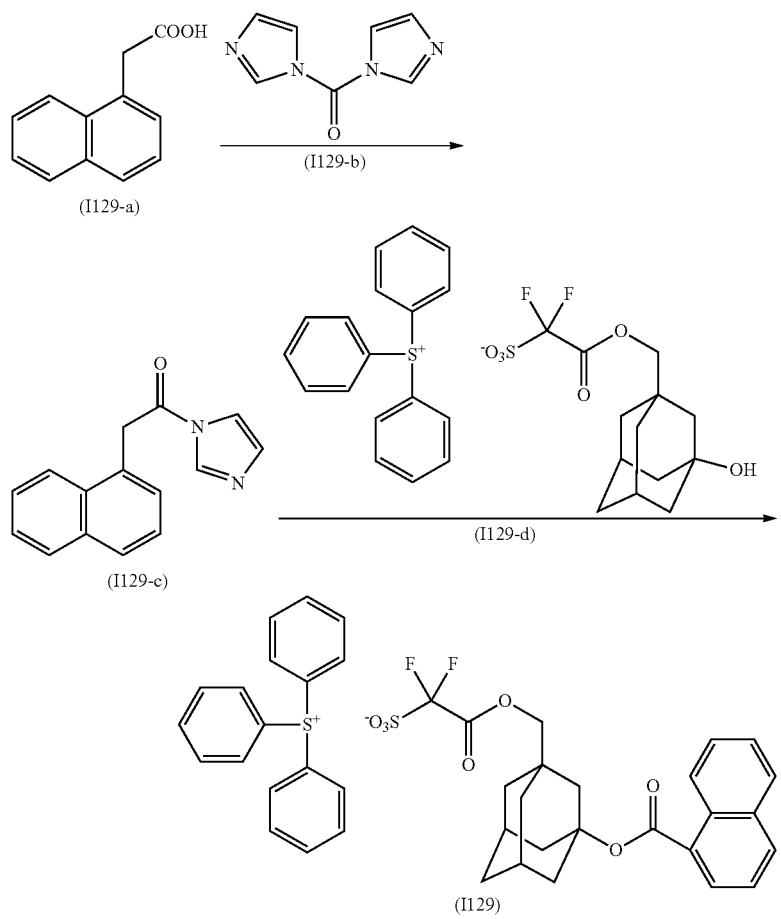

A mixture of 5 parts of the compound represented by the formula (I129-a) and 30 parts of acetonitrile was stirred at 23° C. for 30 minutes. To the mixture, 5.24 parts of the compound represented by the formula (I129-b) was added and stirred at 82° C. for 1 hour to obtain a solution containing the compound represented by the formula (I129-c).

To the solution, 12.95 parts of the compound represented by the formula (I129-d) was fed and then stirred at 82° C. for 44 hours. The obtained reactant was cooled, 159.7 parts of chloroform and 53.23 parts of deionized water were added thereto and stirred at 23° C. for 30 minutes. Then an organic layer was separated after setting the resulting mixture still. Then, the organic layer was washed with 53.23 parts of deionized water in the same manner as above 8 times in total. To the organic layer, 1.76 parts of active carbon was added and stirred at 23° C. for 30 minutes followed by filtration.

The filtrate obtained was concentrated. To the residue obtained, 124 parts of tert-buthylmethylether was added and then stirred. After removing supernatant theirfrom, 20.7 parts of acetonitrile was added to the residue, dissolving it in the acetonitrile, followed by concentration. Then 79.65 parts of tert-buthylmethylether were added to the resultant concentrate and stirred, followed by removing supernatant theirfrom. Then 31.86 parts of acetonitrile was added to the residue, dissolving it in the acetonitrile, followed by concentration.

The resultant concentrate was dissolved in chloroform and concentrated.

By separated from the obtained concentrate with a column (Column: MERCK Silica gel 60-200 mesh, solvent:mixture of chloroform/methanol (=5/1)), 12.46 parts of the salt represented by the formula (I129) were obtained.

MS (ESI(+) Spectrum): $M^+$ 263.1
MS (ESI(−) Spectrum): $M^-$ 507.1

Example 4

Synthesis of the Salt Represented by Formula (I130)

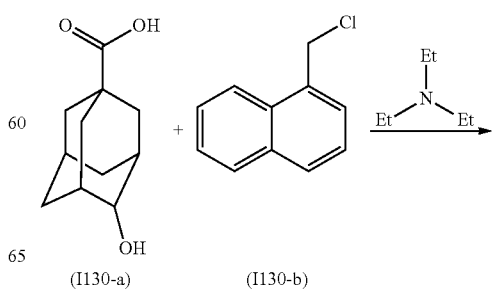

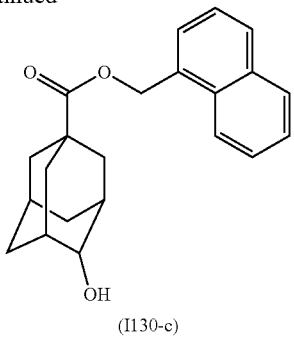

(I130-c)

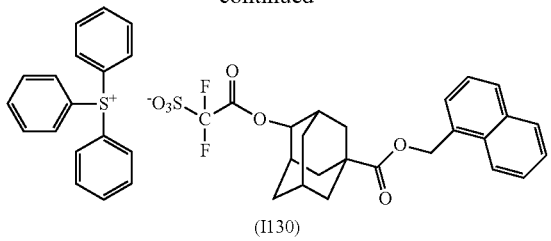

(I130)

A mixture of 28 parts of the compound represented by the formula (I130-a), 140 parts of dimethylformamide and 17.33 parts of triethylamine were stirred at 23° C. for 30 minutes and then heated to 50° C. Then the mixture of 25.2 parts of the compound represented by the formula (I130-b) and 25.2 parts of dimethylformamide was dropped thereinto over 1 hour, followed by stirring them at 50° C. for 24 hours. The mixture was cooled to 23° C., 117.87 parts of deionized water and 942.93 parts of ethyl acetate were added thereto and stirred at 23° C. for 30 minutes. Then an organic layer was separated after setting the resulting mixture still. Then, the organic layer was washed with deionized water in the same manner as above 5 times in total, followed by concentration. To the concentrate, 181.3 parts of ethyl acetate and 2.18 parts of active carbon were added and stirred, followed by filtration. The filtrate obtained was concentrated. To the residue obtained, 188.95 parts of n-heptane was added and then stirred. After removing supernatant theirfrom, 150 parts of ethyl acetate was added to the residue, dissolving it in the ethyl acetate, followed by concentration.

Then 97.41 parts of n-heptane were added to the resultant concentrate and stirred at 23° C. for 24 hours, followed by filtration to obtain 24.99 parts of the compound represented by the formula (I130-c).

A mixture of 19.92 parts of the compound represented by the formula (I130-d) and 100 parts of acetonitrile was stirred at 23° C. for 30 minutes and then heated to 40° C. To the mixture, 8.63 parts of the compound represented by the formula (I130-e) were added and then stirred at 70° C. for 2 hours to obtain a solution containing the compound represented by the formula (I130-f). To the solution, 13.74 parts of the compound represented by the formula (I130-c) and 54.9 parts of chloroform were fed and then stirred at 50° C. for 16 hours, followed by concentration.

To the concentrate, 150 parts of chloroform and 70 parts of 2% oxalic acid solution were added thereto and stirred at 23° C. for 30 minutes. Then an organic layer was separated after setting the resulting mixture still. Then, washing it with an oxalic acid solution was conducted once more. To the resultant organic layer, 75 parts of deionized water were added and stirred at 23° C. for 30 minutes. Then, washing it with the deionized water solution was conducted further 4 times. The resultant organic layer, 1.99 parts of active carbon was added and then stirred at 23° C. for 30 minutes, followed by filtration. To the concentrate, 96.56 parts of tert-buthylmethylether was added, followed by stirring them. The supernatant was removed theirfrom, followed by concentration. Dissolving the concentrate in acetonitrile, followed by concentration. To the concentrate, 89.9 parts of tert-buthylmethylether was added and then stirred at 23° C. for 3 hours, followed by filtration to obtain 15.57 parts of the salt represented by the formula (I130).

MS (ESI(+) Spectrum): M$^+$ 263.1
MS (ESI(−) Spectrum): M$^-$ 493.1

Synthesis Example

Synthesis of the Resin (A)

The compounds (monomers) used for the synthesis of the resins are shown as follow:

Hereinafter, the compounds represented by the formulae (a1-1-2), (a2-1-1) and (a3-1-1) are referred to as "monomer (a1-1-2)", "monomer (a2-1-1)" and "monomer (a3-1-1)".

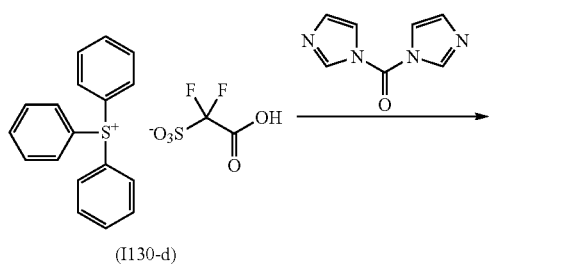

(I130-d)

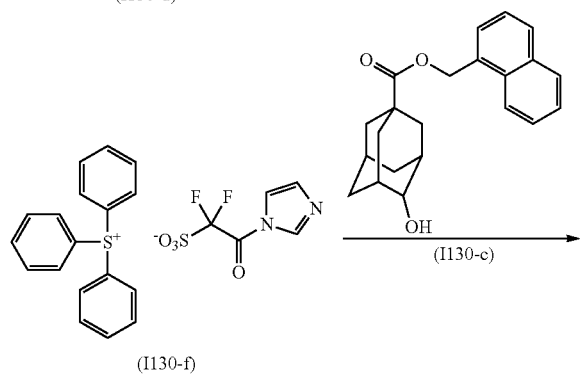

(I130-f)

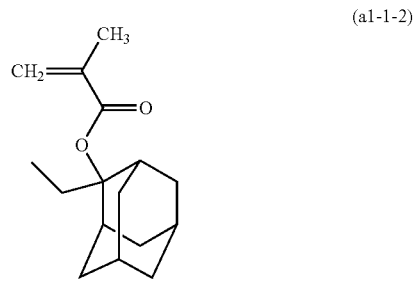

(a1-1-2)

(a2-1-1)

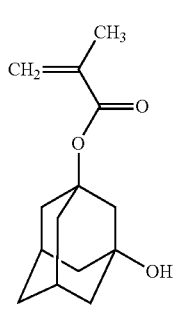

(a3-1-1)

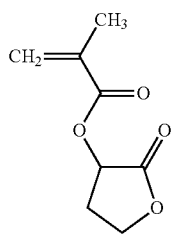

[Synthesis of the Resin (A1)]

Monomer (a1-1-2) (39.7 g, 0.16 moles) and p-acetoxystylene (103.8 g, 0.64 moles) were dissolved in 265 g of isopropanol, and the solution was heated to 75° C. To the mixture, 11.05 g (0.048 moles) of dimethyl 2,2-azobis(2-methylpropyonate) as an initiator was dissolved in 22.11 g of isopropanol, and then the solution the initiator was dropped into the solution of monomer, followed by distilling it by heating for 12 hours. Then the reaction mixture was cooled and then poured into a large amount of methanol to cause precipitation to collect copolymer of monomer (a1-1-2) and p-acetoxystylene. The amount of the copolymer was 250 g, as collected precipitate including a little amount of methanol.

To 202 g of methanol, 250 g of the copolymer and 10.3 g (0.084 moles) of 4-dimethylaminopyridine were added, followed by distilling it by heating for 20 hours to conduct a reaction. The reaction mixture was cooled and then neutralized with 7.6 g (0.126 moles) of glacial acetic acid, followed by pouring it into a large amount of water to cause precipitation. The precipitated polymer was filtrated and dissolved in acetone, followed by pouring it into a large amount of water to cause precipitation, which operation was conducted three times.

The amount of the obtained copolymer of methacrylate 2-ethyl-2-adamantyl and p-hydroxystylene was 95.9 g. The copolymer has a weight-average molecular weight of about 8.6×10³. In the copolymer, the ratio of copolymerization was about 20:80 (=methacrylate 2-ethyl-2-adamantyl: p-hydroxystylene). Such copolymer has the structural units as shown bellow, which is referred to as "Resin (A1)".

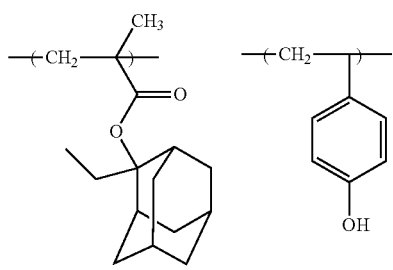

[Synthesis of the Resin (A2)]

Except that the amounts of monomer (a1-1-2) and p-acetoxystylene were respectively 59.6 g (0.24 moles) and 90.8 g (0.56 moles), the operations were conducted in the same manner as synthesis of Resin (A1) to produce 102.8 g of copolymer of monomer (a1-1-2) and p-hydroxystylene. The copolymer has a weight-average molecular weight of about 8.2×10³. The ratio of the copolymezation between methacrylate 2-ethyl-2-adamantyl and p-hydroxystylene was about 30:70 (=methacrylate 2-ethyl-2-adamantyl:p-hydroxystylene). Such copolymer has the structural units as shown bellow, which is referred to as "Resin (A2)".

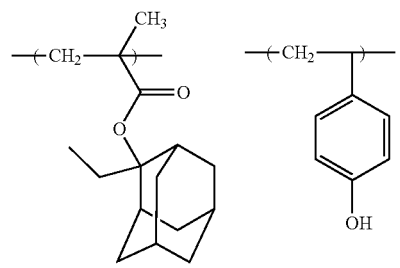

[Synthesis of the Resin (A3)]

The monomers (a1-1-2), (a2-1-1) and (a3-1-1) were mixed in a molar ratio of 50/25/25(monomer(a1-1-2)/monomer(a2-1-1)/monomer (a3-1-1)), and 1,4-dioxane was added to the mixture in the amount by 1.5 times weight of the total monomer weights.

To the mixture, azobisisobutyronitrile as an initiator in a ratio of 1 mol % per all monomer molar amount and azobis(2,4-dimethylvaleronitrile) as an initiator in a ratio of 3 mol % per on all monomer molar amount were added, and the obtained mixture was heated at 80° C. for about 8 hours. The reaction mixture obtained was poured into a large amount of a mixture of methanol and water (weight ratio=4/1) to cause precipitation. The precipitate was collected by filtration and then, was dissolved in 1,4-dioxane followed by pouring the resultant solution into a large amount of a mixture of methanol and water (weight ratio=4/1) to cause precipitation. This operation was repeated twice for purification. As a result, a copolymer having a weight-average molecular weight of about 9.2×10³ was obtained in yield of 60%.

This copolymer is referred to as resin A3. Resin A3 had the following structural units.

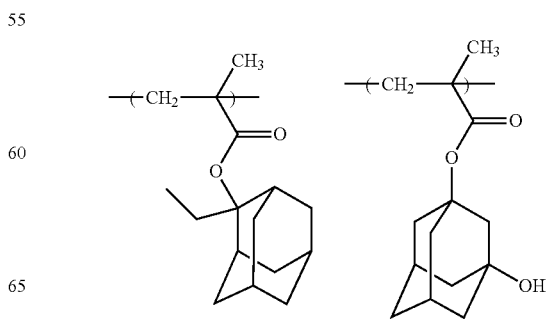

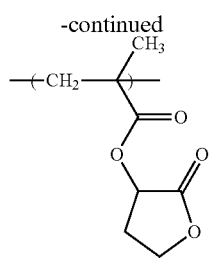

[Synthesis of the resin (A4)]

To 11.18 parts of monomer (a1-1-2), 14.6 parts of p-acetoxystylene and 3.55 parts of monomer (a2-1-1), 29.32 parts of 1,4-dioxane was added, followed by heating to 87° C.

To the obtained solution, 2.96 parts of azobisisobutyronitrile was added and kept at 87° C. for 6 hours. Then the obtained reaction mixture was cooled and then poured into a mixture of 304.97 parts of methanol and 76.24 parts of deionized water to precipitate the polymer, followed by filtrating it.

The obtained filtrates and 2.93 parts of 4-dimethylaminopyridine were added to the same amount of methanol as that of filtrates, followed by distilling it by heating for 20 hours to conduct a reaction.

The reaction mixture was cooled and then neutralized with 2.09 parts of glacial acetic acid, followed by pouring it into a large amount of water to cause precipitation. The precipitated polymer was filtrated and dissolved in acetone, followed by pouring it into a large amount of water to cause precipitation, which operation was conducted three times.

As a result, 27.82 parts of copolymer having a weight-average molecular weight of about $3.5 \times 10^3$ was obtained. This copolymer is referred to as resin A4. Resin A4 had the following structural units derived from monomer (a1-1-2), p-hydroxystylene and monomer (a2-1-1).

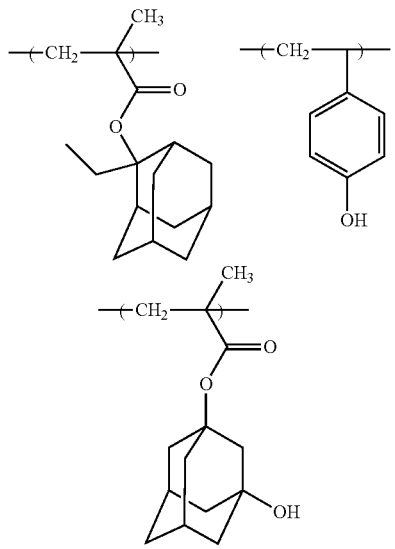

[Synthesis of the resin (A5)]

To 11.8 parts of monomer (a1-1-2), 14.6 parts of p-acetoxystylene, 1.77 parts of monomer (a2-1-1) and 1.28 parts of monomer (a3-1-1), 28.83 parts of 1,4-dioxane was added, followed by heating to 87° C.

To the obtained solution, 2.96 parts of azobisisobutyronitrile was added and kept at 87° C. for 6 hours. Then the obtained reaction mixture was cooled and then poured into a mixture of 299.81 parts of methanol and 74.95 parts of deionized water to precipitate the polymer, followed by filtrating it.

The obtained filtrates and 2.88 parts of 4-dimethylaminopyridine were added to the same amount of methanol as that of filtrates, followed by distilling it by heating for 15 hours to conduct a reaction.

The reaction mixture was cooled and then neutralized with 2.05 parts of glacial acetic acid, followed by pouring it into a large amount of water to cause precipitation. The precipitated polymer was filtrated and dissolved in acetone, followed by pouring it into a large amount of water to cause precipitation, which operation was conducted three times.

As a result, 26.91 parts of copolymer having a weight-average molecular weight of about $3.8 \times 10^3$ was obtained. This copolymer is referred to as resin A5. Resin A5 had the following structural units derived from monomer (a1-1-2), p-hydroxystylene, monomer (a2-1-1) and monomer (a3-1-1).

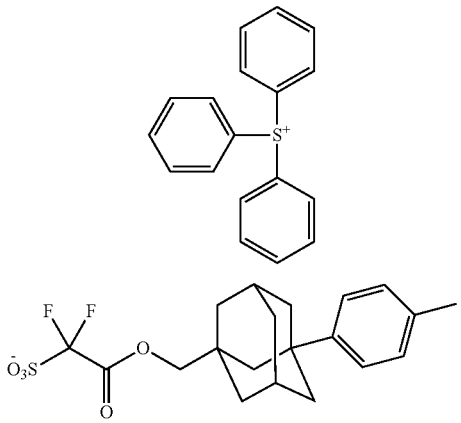

[Production of the Photoresist Compositions]

The following components were mixed and dissolved in the mixture of the following solvents as shown in Tables 5 and 6, further, filtrated through a fluorine resin filter having pore diameter of 0.2 μm to prepare photoresist compositions.

<Acid Generator>

I1: Salt represented by the formula (I1)

I12: Salt represented by the formula (I12)

I129: Salt represented by the formula (I129)

I130: Salt represented by the formula (I130)

B1-11:

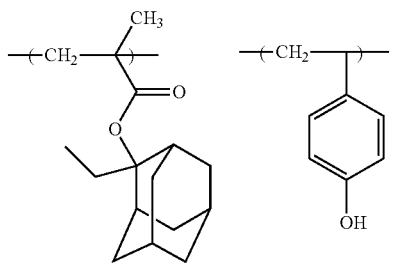

-continued

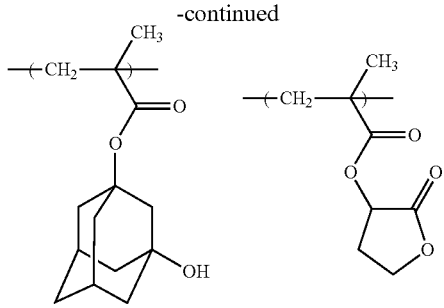

<Resin>
A1: Resin A1
A2: Resin A2
A3: Resin A3
A4: Resin A4
A5: Resin A5
<Basic Compound: Quencher>
C1: 2,6-diisopropylaniline
C2: tetrabutylammonium hydroxide
C3: tetra-n-butylammonium salytylate

TABLE 5

| Ex. No. | Acid generator (kind/amount (part)) | Resin (kind/amount (part)) | Quencher (kind/amount (part)) | PB (° C.) | PEB (° C.) |
|---|---|---|---|---|---|
| Ex. 5 | I1/1.2 | A1/6.75 and A2/6.75 | C1/0.03 and C2/0.03 | 110° C. | 110° C. |
| Ex. 6 | I130/3.0 | A4/10 | C3/0.3 | 120° C. | 120° C. |
| Ex. 7 | I130/3.0 | A5/10 | C3/0.3 | 120° C. | 120° C. |
| Ex. 8 | I130/3.0 | A5/10 | C3/0.3 | 110° C. | 110° C. |
| Comp. Ex. 1 | B1-11/1.2 | A1/6.75 and A2/6.75 | C1/0.03 and C2/0.03 | 110° C. | 110° C. |

<Solvent for Examples 5 to 8 and Comparative Example 1>

| propylene glycol monomethyl ether acetate | 400 parts |
| propylene glycol monomethyl ether | 100 parts |
| γ-butyrolactone | 5 parts |

TABLE 6

| Ex. No. | Acid generator (kind/amount (part)) | Resin (kind/amount (part)) | Quencher (kind/amount (part)) | PB (° C.) | PEB (° C.) |
|---|---|---|---|---|---|
| Ex. 9 | I1/1 | A3/10 | C1/0.07 | 100° C. | 95° C. |
| Ex. 10 | I12/1 | A3/10 | C1/0.07 | 100° C. | 95° C. |
| Ex. 11 | I129/1 | A3/10 | C1/0.07 | 100° C. | 95° C. |
| Ex. 12 | I130/1 | A3/10 | C1/0.07 | 100° C. | 95° C. |
| Comp. Ex. 2 | B1-11/1 | A3/10 | C1/0.07 | 100° C. | 95° C. |

<Solvent for Examples 9 to 12 and Comparative Example 2>

| propylene glycol monomethyl ether acetate | 265 parts |
| propylene glycol monomethyl ether | 20 parts |
| 2-heptane | 20 parts |
| γ-butyrolactone | 5 parts |

(Evaluation of the Photoresist Compositions: Exposure of Electron Beam)

Silicon wafers (12 inches) were each treated with hexamethyldisilazane on the direct hotplate at 90° C. for 60 seconds.

Each of the photoresist compositions prepared as above was spin-coated over the treated wafer so that the thickness of the resulting film became 0.06 μm after drying.

The silicon wafers thus coated with the respective photoresist compositions were each prebaked on a direct hotplate at a temperature shown in the column "PB" in Table 5 for 60 seconds.

Using an Electron-beam direct writing system ("HL-800D 50 keV" manufactured by HITACHI), each wafer coated with the resist film was subjected to line and space pattern exposure with the exposure quantity being varied stepwise.

After the exposure, each wafer was subjected to post-exposure baking on a hotplate at a temperature shown in the column "PEB" in Table for 60 seconds and then to paddle development for 60 seconds with an aqueous solution of 2.38 wt % tetramethylammonium hydroxide. Effective Sensitivity (ES) was expressed as the amount of exposure that the line width of the line and space pattern of 60 nm became 1:1 after development.

Each photoresist composition at effective sensitivity was observed with a scanning electron microscope. Photoresist compositions of Examples 5 to 8 showed a sharp resolution at 50 nm, while the photoresist composition of Comparative Example 1 showed a resolution at 50 nm with a round top.

(Evaluation of the photoresist compositions: Exposure of KrF excimer laser)

Silicon wafers (4 inches) were each coated with "DUV-42", which is an organic anti-reflective coating composition available from Brewer, and then baked at 215° C. for 60 seconds, to form a 600 Å-thick organic anti-reflective coating.

Each of the photoresist compositions prepared as above was spin-coated over the anti-reflective coating so that the thickness of the resulting film became 400 nm after drying.

The silicon wafers thus coated with the respective photoresist compositions were each prebaked on a direct hotplate at a temperature shown in the column "PB" in Table 5 for 60 seconds.

Using an KrF excimer laser exposure ("NSR-2250EX12B" manufactured by NICON, NA=0.55, ⅔ Annular), each wafer thus formed with the respective resist film was subjected to line and space pattern exposure with the exposure quantity being varied stepwise.

After the exposure, each wafer was subjected to post-exposure baking on a hotplate at a temperature shown in the column "PEB" in Table 5 for 60 seconds and then to paddle development for 60 seconds with an aqueous solution of 2.38 wt % tetramethylammonium hydroxide.

Effective Sensitivity (ES) was expressed as the amount of exposure that the line width of the line and space pattern of 200 nm became 1:1 after development.

Focus Margin (DOF):

The photoresist patterns were obtained at the exposure amount of ES, with the focal point distance being varied stepwise. Each of patterns developed on the organic anti-reflective coating substrate after the development were observed and the focal point distances when the patterns of which line width were within 180 nm±5% (between 171 nm and 189 nm) were measured and the difference between the max value of the focal point distance and the minimum value of the focal point distance was calculated. When the difference is more than 0.15 μm, DOF is very good and its evaluation is marked by "○", and when the difference is 0.15 μm or less, DOF is bad and its evaluation is marked by "x". Further, each of the differences is also shown in parentheses in a column of "DOF". The difference is larger, the better focus margin the photoresist composition has. The results are shown in Table 7.

TABLE 7

|  | DOF |
| --- | --- |
| Ex. 5 | ○ (0.18) |
| Ex. 6 | ○ (0.21) |
| Ex. 7 | ○ (0.24) |
| Ex. 8 | ○ (0.21) |
| Compar. Ex. 1 | X (0.12) |

(Evaluation of the Photoresist Compositions: Exposure of EUV)
Silicon wafers (12 inches) were each treated with hexamethyldisilazane on the direct hot plate at 90° C. for 60 seconds.
Each of the photoresist compositions of Examples 5 and 10 was spin-coated over the treated wafer so that the thickness of the resulting film became 0.05 μm after drying.
The silicon wafers thus coated with the respective photoresist compositions were each prebaked on a direct hotplate at a temperature shown in the column "PB" in Table 5 for 60 seconds.
Using an EUV exposure, each wafer coated with the resist film was subjected to line and space pattern exposure with the exposure quantity being varied stepwise.
After the exposure, each wafer was subjected to post-exposure baking on a hotplate at a temperature shown in the column "PEB" in Table 5 for 60 seconds and then to paddle development for 60 seconds with an aqueous solution of 2.38 wt % tetramethylammonium hydroxide.
Focus Margin (DOF):
The photoresist patterns were obtained at the exposure amount of ES, with the focal point distance being varied stepwise. Each of patterns developed on the organic anti-reflective coating substrate after the development were observed and the focal point distances when the patterns of which line width were within 50 nm±5% (between 47.5 nm and 52.5 nm) were measured and the difference between the max value of the focal point distance and the minimum value of the focal point distance was calculated. When the difference is more than 0.15 μm, DOF is very good and its evaluation is marked by "○", and when the difference is 0.15 μm or less, DOF is bad and its evaluation is marked by "x". Further, each of the differences is also shown in parentheses in a column of "DOF". The difference is larger, the better focus margin the photoresist composition has. The results are shown in Table 8.

TABLE 8

|  | DOF |
| --- | --- |
| Ex. 5 | ○ (0.18) |
| Ex. 10 | ○ (0.24) |

(Evaluation of the Photoresist Compositions: Exposure of ArF Excimer Laser)
Silicon wafers (2 inches) were each coated with "ARC-29", which is an organic anti-reflective coating composition available from Nissan Chemical, and then baked at 205° C. for 60 seconds, to form a 78 Å-thick organic anti-reflective coating. Each of the photoresist compositions prepared as above was spin-coated over the anti-reflective coating so that the thickness of the resulting film became 85 nm after drying.
The silicon wafers thus coated with the respective photoresist compositions were each prebaked on a direct hotplate at a temperature shown in the column "PB" in Table 6 for 60 seconds. Using an ArF excimer stepper for immersion exposure ("XT:1900Gi" manufactured by ASML, NA=1.35, ¾ Annular, X-Y polarization), each wafer thus formed with the respective resist film was subjected to line and space pattern exposure with the exposure quantity being varied stepwise. Ultrapure water was used as an immersion medium.
After the exposure, each wafer was subjected to post-exposure baking on a hotplate at a temperature shown in the column "PEB" in Table 6 for 60 seconds and then to paddle development for 60 seconds with an aqueous solution of 2.38 wt % tetramethylammonium hydroxide.
Focus Margin (DOF):
The photoresist patterns were obtained at the exposure amount of ES, with the focal point distance being varied stepwise. Each of patterns developed on the organic anti-reflective coating substrate after the development were observed and the focal point distances when the patterns of which line width were within 50 nm±5% (between 47.5 nm and 52.5 nm) were measured and the difference between the max value of the focal point distance and the minimum value of the focal point distance was calculated. When the difference is more than 0.12 DOF is very good and its evaluation is marked by "○", and when the difference is 0.12 μm or less, DOF is bad and its evaluation is marked by "x". Further, each of the differences is also shown in parentheses in a column of "DOF". The difference is larger, the better focus margin the photoresist composition has. The results are shown in Table 9.

TABLE 9

|  | DOF |
| --- | --- |
| Ex. 9 | ○ (0.15) |
| Ex. 10 | ○ (0.15) |
| Ex. 11 | ○ (0.18) |
| Ex. 12 | ○ (0.18) |
| Compar. Ex. 2 | X (0.03) |

INDUSTRIAL AVAILABILITY

The salt of the present invention is suitable as an acid generator for photoresist composition. The photoresist composition of the present invention, which comprises such salt, can provide photoresist composition with excellent DOF by using lithography with ArF, KrF, EUV or the like.

What is claimed is:
1. A salt represented by the formula (I):

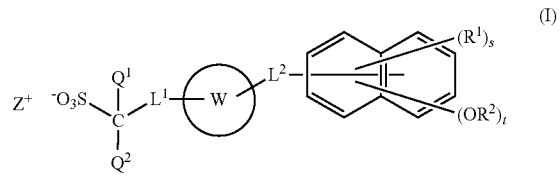

wherein $Q^1$ and $Q^2$ independently each represent a fluorine atom or a C1-C6 perfluoroalkyl group, $L^1$ represents a C1-C17 divalent saturated hydrocarbon group in which one or more —CH$_2$— can be replaced by —O— or —CO—, $L^2$ represents *—CO—O—(CH$_2$)$_v$— in which v represents an integer of 0 to 4 and * represents a binding position to ring W, ring W represents a C3-C36 aliphatic ring in which one or more —CH$_2$— can be replaced by —O—, —S—, —CO— or —SO$_2$— and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group, s represents an integer of 0 to 3, t represents an integer of 0 to 2, $R^1$ independently represents in each occurrence a C1-C18 alicyclic hydrocarbon group in which one or more —CH$_2$— can be replaced by —O— or —CO—, $R^2$ independently represents in each occurrence a hydrogen atom, a C1-C6 alkyl group, a C3-C12 cycloalkyl group, a C2-C7 acyl group, a C2-C7 alkoxycarbonyl group, a C2-C7 alkoxyalkyl group or a glycidyl group, and $Z^+$ represents an organic counter ion.

2. The salt according to claim 1 wherein the formula (I) is represented by the formula:

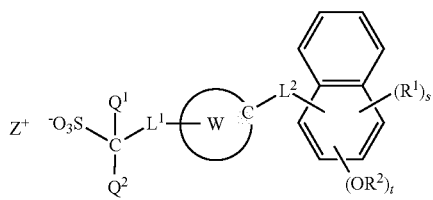

in which $Q^1$, $Q^2$, $L^1$, $L^2$, ring W, s, t, $R^1$, $R^2$, and $Z^+$ are defined as in claim 1.

3. The salt according to claim 1 or 2, wherein ring W is a ring represented by the formula (Ia1-1), (Ia1-2) or (Ia1-3):

(Ia1-1)

(Ia1-2)

(Ia1-3)

wherein one or more —CH$_2$— in the above-mentioned formula can be replaced by —O—, —S—, —CO— or —SO$_2$— and one or more hydrogen atoms in the above-mentioned formula can be replaced by a hydroxyl group, a C1-C12 alkyl group, a C1-C12 alkoxy group, a C3-C12 alicyclic hydrocarbon group or a C6-C10 aromatic hydrocarbon group.

4. The salt according to claim 1 or 2, wherein $L^1$ is *—CO—O—(CH$_2$)$_u$— in which u represents an integer of 0 to 6 and * represents a binding position to —C($Q^1$)($Q^2$)-.

5. The salt according to claim 1 or 2, wherein $Z^+$ is an arylsulfonium cation.

6. An acid generator comprising the salt according to claim 1 or 2.

7. A photoresist composition comprising the acid generator according to claim 6 and a resin having an acid-labile group, being insoluble or poorly soluble in an aqueous alkali solution but becoming soluble in an aqueous alkali solution by the action of an acid.

8. The photoresist composition according to claim 7, which further comprises a basic compound.

9. A process for producing a photoresist pattern comprising the following steps (1) to (5):

(1) a step of applying the photoresist composition according to claim 7 on a substrate, (2) a step of drying the composition on the substrate to form a composition film, (3) a step of exposing the composition film to radiation, (4) a step of baking the exposed film, and (5) a step of developing the baked resist film to thereby form a photoresist pattern.

* * * * *